US010267745B2

United States Patent
Otani et al.

(10) Patent No.: US 10,267,745 B2
(45) Date of Patent: Apr. 23, 2019

(54) DEFECT DETECTION METHOD AND DEFECT DETECTION DEVICE AND DEFECT OBSERVATION DEVICE PROVIDED WITH SAME

(71) Applicant: HITACHI HIGH-TECHNOLOGIES CORPORATION, Tokyo (JP)

(72) Inventors: Yuko Otani, Tokyo (JP); Takehiro Tachizaki, Yokohama (JP); Masahiro Watanabe, Yokohama (JP); Shunichi Matsumoto, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/673,582

(22) Filed: Aug. 10, 2017

(65) Prior Publication Data

US 2017/0363547 A1    Dec. 21, 2017

Related U.S. Application Data

(63) Continuation of application No. 14/942,124, filed on Nov. 16, 2015, now Pat. No. 9,759,666, which is a (Continued)

(30) Foreign Application Priority Data

Nov. 18, 2009    (JP) .................................. 2009-262445

(51) Int. Cl.
   *G01N 21/00*    (2006.01)
   *G01N 21/88*    (2006.01)
   (Continued)

(52) U.S. Cl.
   CPC ......... *G01N 21/8806* (2013.01); *G01N 21/21* (2013.01); *G01N 21/47* (2013.01);
   (Continued)

(58) Field of Classification Search
   CPC .............. G01N 21/9501; G01N 21/21; G01N 21/95607; G01N 21/95623; G01N 2021/8822
   (Continued)

(56) References Cited

U.S. PATENT DOCUMENTS

| 4,922,308 A | 5/1990 | Noguchi et al. |
| 5,046,847 A * | 9/1991 | Nakata .................... G01N 21/94 |
| | | 250/559.41 |

(Continued)

FOREIGN PATENT DOCUMENTS

| JP | 62-163951 A | 7/1987 |
| JP | 6-10656 B2 | 2/1994 |

(Continued)

*Primary Examiner* — Hoa Q Pham
(74) *Attorney, Agent, or Firm* — Baker Botts L.L.P.

(57) ABSTRACT

The disclosed device, which, using an electron microscope or the like, minutely observes defects detected by an optical appearance-inspecting device or an optical defect-inspecting device, can reliably insert a defect to be observed into the field of an electron microscope or the like, and can be a device of smaller scale. The electron microscope, which observes defects detected by an optical appearance-inspecting device or an optical defect-inspecting device, has a configuration incorporating an optimal microscope that re-detects defects, and a spatial filter and a distribution polarization element are inserted at the pupil plane when making dark-field observations using this optical microscope. The electron microscope, which observes defects detected by an optical appearance-inspecting device or an optical defect-inspecting device, has a configuration incorporating an optimal microscope that re-detects defects, and a distribution filter is inserted at the pupil plane when making dark-field observations using this optical microscope.

6 Claims, 37 Drawing Sheets

Related U.S. Application Data continuation of application No. 14/587,271, filed on Dec. 31, 2014, now Pat. No. 9,217,718, which is a continuation of application No. 13/510,300, filed as application No. PCT/JP2010/006653 on Nov. 12, 2010, now Pat. No. 8,953,156.

(51) Int. Cl.
  *G01N 21/21* (2006.01)
  *G01N 21/95* (2006.01)
  *G01N 21/47* (2006.01)
  *G01N 21/94* (2006.01)
  *G01N 21/956* (2006.01)

(52) U.S. Cl.
  CPC ......... *G01N 21/94* (2013.01); *G01N 21/9501* (2013.01); *G01N 21/95607* (2013.01); *G01N 21/95623* (2013.01); *G01N 2021/8822* (2013.01); *G01N 2021/8848* (2013.01); *G01N 2201/063* (2013.01); *G01N 2201/06113* (2013.01)

(58) Field of Classification Search
  USPC .................................. 356/237.1–237.5, 369
  See application file for complete search history.

(56) References Cited

U.S. PATENT DOCUMENTS

| | | | |
|---|---|---|---|
| 5,717,485 A | 2/1998 | Ito et al. | |
| 6,137,570 A | 10/2000 | Chuang et al. | |
| 6,407,373 B1 | 6/2002 | Dotan | |
| 6,798,511 B1* | 9/2004 | Zhan | G01J 4/00 356/369 |
| 7,110,106 B2 | 9/2006 | Xu et al. | |
| 7,728,965 B2 | 6/2010 | Haller et al. | |
| 7,851,753 B2 | 12/2010 | Uto et al. | |
| 8,045,146 B2 | 10/2011 | Saito et al. | |
| 8,169,613 B1 | 5/2012 | Biellak et al. | |
| 9,678,021 B2* | 6/2017 | Urano | G01N 21/95623 |
| 9,773,641 B2* | 9/2017 | Otani | G01N 21/8806 |
| 9,874,526 B2* | 1/2018 | Liu | G01N 21/8806 |
| 2002/0145732 A1 | 10/2002 | Vaez-Iravani et al. | |
| 2003/0087282 A1* | 5/2003 | Oshida | G01J 3/4406 435/6.11 |
| 2004/0124363 A1 | 7/2004 | Yoshida et al. | |
| 2006/0181700 A1* | 8/2006 | Andrews | G01N 21/21 356/237.2 |
| 2006/0256326 A1 | 11/2006 | Bills et al. | |
| 2007/0057184 A1 | 3/2007 | Uto et al. | |
| 2007/0177136 A1 | 8/2007 | Nakano et al. | |
| 2008/0059094 A1 | 3/2008 | Shimura et al. | |
| 2008/0073524 A1 | 3/2008 | Nishiyama et al. | |
| 2008/0253262 A1 | 10/2008 | Andersen et al. | |
| 2008/0297783 A1 | 12/2008 | Urano et al. | |
| 2009/0079973 A1 | 3/2009 | Uto et al. | |
| 2009/0279079 A1 | 11/2009 | Shibata et al. | |
| 2011/0194101 A1 | 8/2011 | Tachizaki et al. | |
| 2012/0262709 A1 | 10/2012 | Uto et al. | |
| 2017/0082425 A1* | 3/2017 | Minekawa | G01B 11/30 |

FOREIGN PATENT DOCUMENTS

| | | |
|---|---|---|
| JP | 7-229845 A | 8/1995 |
| JP | 7-270144 A | 10/1995 |
| JP | 2000-352697 A | 12/2000 |
| JP | 2007-071803 A | 3/2007 |
| JP | 2007-235023 A | 9/2007 |

* cited by examiner (a)

(b)

(a)

(b)

(a) APPLICATION EXAMPLE OF POLARIZATION DIRECTION CONTROL METHOD WITH ELECTRODE APPLICATION FUNCTION USING LIQUID CRYSTAL (b) APPLICATION EXAMPLE OF POLARIZATION DIRECTION CONTROL METHOD WITHOUT ELECTRODE APPLICATION FUNCTION USING LIQUID CRYSTAL

DEFECT DETECTION METHOD AND DEFECT DETECTION DEVICE AND DEFECT OBSERVATION DEVICE PROVIDED WITH SAME

CLAIM OF PRIORITY

This application is a continuation of U.S. patent application Ser. No. 14/942,124, filed on Nov. 16, 2015, which is a continuation of U.S. patent application Ser. No. 14/587,271, filed on Dec. 31, 2014 (now U.S. Pat. No. 9,217,718), which is a continuation of U.S. patent application Ser. No. 13/510,300, filed on Jul. 6, 2012 (now U.S. Pat. No. 8,953,156), which is a U.S. National Phase application under 35 U.S.C. § 371 of International Application No. PCT/JP2010/006653, filed on Nov. 12, 2010, which claims benefit of priority to Japanese Application No. 2009-262445, filed on Nov. 18, 2009, the disclosures of all of which are incorporated herein by reference.

TECHNICAL FIELD

The present invention relates to a defect detection method, a defect detection device, and a defect observation device including the same for inspecting defects and the like on a surface of a bare wafer without semiconductor patterns or a filmed wafer without semiconductor patterns or on a surface of a disk.

BACKGROUND ART

For example, in a production process of semiconductor devices, presence of foreign matter or pattern defects such as a short-circuit and a disconnection (defects described hereinafter include foreign matter and pattern defects) on a semiconductor substrate (wafer) causes failures including an insulation failure and a short-circuit in the wiring. Further, as the circuit pattern formed on a wafer becomes finer, a finer defect also causes an insulation failure in a capacitor and destruction of a gate oxide film or the like. As for defects, matter appearing from a movable unit of a transporting device, matter generating from a human body, matter produced by a reaction of process gas in a process device, and matter beforehand mixed in agents and materials are mixed due to various causes and in various states. Hence, detecting a defect taking place during the production process and determining the source of the defect in a short period of time to thereby prevent defective products are important to mass-product semiconductor devices.

Heretofore, as a method of ascertaining the cause of a defect, there has been a method in which the position of the defect is first identified by a defect inspection device and the defect is precisely observed and/or classified by use of a Scanning Electron Microscope (SEM) or the like and is compared with a database, to thereby estimate the cause of the defect.

Here, the defect inspection device is an optical defect inspection device which emits light onto a surface of a semiconductor substrate using a laser to conduct dark-field observation of scattered light from the defect to thereby identify the position of the defect, or an optical appearance-inspection device or an SEM inspection device in which light of a lamp or a laser or an electron beam is emitted to detect a bright-field optical image of a semiconductor substrate and the image is compared with reference information to thereby identify the position of the defect on the semiconductor substrate. Such observation methods have been disclosed in patent literature 1 or 2.

Additionally, as for the device to precisely observe a defect by an SEM, there have been respectively described in patent literature 3 to 5 a method and a device in which by use of positional information of a defect on a sample detected by a second inspection device, the position on the sample is detected by an optical microscope installed in the SEM defect inspection device to correct the positional information of the defect on the sample detected by the second inspection device and then the defect is precisely observed (reviewed) by the SEM defect inspection device as well as an operation in which when the defect is observed by the SEM defect inspection device, the height of the sample surface is optically detected to be aligned with a focal position of the SEM.

CITATION LIST

Patent Literature

Patent literature 1: JP-A-07-270144
Patent literature 2: JP-A-2000-352697
Patent literature 3: U.S. Pat. No. 6,407,373
Patent literature 4: JP-A-2007-71803
Patent literature 5: JP-A-2007-235023

SUMMARY OF INVENTION

Technical Problem

When detecting a defect on a surface of a semiconductor substrate by use of an optical defect inspection device, in order to raise the throughput of the inspection, the laser beam for the dark-field illumination is emitted onto the surface of the semiconductor substrate with its spot size enlarged to thereby scan the surface of the semiconductor substrate. Hence, the precision of positional coordinates obtained using the position of the laser beam spot to scan the surface of the semiconductor substrate includes a large error component.

When it is desired to precisely observe a defect using an SEM based on the positional information of the defect including such large error component, there may occur a situation in which the defect to be observed is outside the visual field of the SEM which observes it with a magnification factor extremely larger than that of the optical defect inspection device. In such situation, to place the image of the defect to be viewed in the visual field of the SEM, the operator makes a search for the defect by moving the observation point in the visual field of the SEM; this takes a long period of time and causes the reduction in the SEM observation throughput.

Therefore, it is an object of the present invention to provide a defect observation device in which when precisely observing, by use of an SEM, a defect detected by an optical defect inspection device or an optical appearance inspection device, it is possible to detect, with high sensitivity, a fine defect detected by the optical defect inspection device or the optical appearance inspection device and to surely place the defect in the visual field of the SEM, and it is possible to reduce the defect observation device in size.

Further, in the recent LSI production, due to finer circuit patterns corresponding to needs of high integration, the width of the wiring patterns formed on a wafer is reduced. On the other hand, to secure conductivity of the wiring, the height of the wiring pattern is increased.

In association therewith, it is desired in the optical defect inspection device to reduce the size of the defect to be detected. In such situation, for the optical defect inspection device, it has being desired to enlarge the Numerical Aperture (NA) of the objective lens for inspection, and an optical super-resolution technique is under development; however, the NA value thus enlarged of the objective for inspection has arrived at the physical limit and it is hence an authentic approach that the wavelength of the light to be used for the inspection is reduced to short wavelengths in the ranges of the UV light and the Deep UV (DUV) light.

However, the LSI devices include memory products formed primarily using a high-density repetitive pattern and logic products formed primarily using a non-repetitive pattern, and the patterns to be inspected are complicated and diversified in structure. Hence, it is difficult to surely detect a defect (target defect) to be controlled at LSI device production. The target defects desired to be detected include, in addition to foreign matter appearing during the respective production processes and contour failures in circuit patterns after etching, a void and a scratch in the CPM process. Moreover, there also exists a short circuit (to be also called a bridge) between wiring patterns in the gate wiring and the metallic wiring unit of aluminum or the like. Particularly, the short circuit between wiring patterns is lower in the height than the wiring patterns in many cases, which hence leads to a problem of difficulty in the detection.

Also, in LSI devices including multilayer wiring, since the target defects become finer and the underlay patterns in places where defects take place are also diversified, it is more difficult to detect the defects. Particularly, in the process in which the transparent film (indicating here transparent with respect to lighting wavelength) of an insulation film or the like is exposed to the upper-most surface, the non-uniformity in the intensity of interference light due to quite a small difference in thickness of the transparent film becomes optical noise. Hence, there exists a problem in which the target defect is to be revealed while reducing influences from the non-uniformity in the intensity of interference light. In addition, to stably produce LSI, it is required to control the state of failures in LSI devices; for this purpose, it is desirable to inspect all LSI substrates. Consequently, there exists a problem which the target defect is to be detected in a short period of time.

It is therefore another object of the present invention to provide a defect detection device and a defect detection method to detect various defects on a wafer at a high speed and with high sensitivity and a defect observation device on which they are mounted.

Solution to Problem

Description will be given hereinafter of aspects for outlines of representative ones of the inventions disclosed by the present application to achieve either one of the objects above.

(1) A defect detection device, characterized by comprising a illumination optical system for emitting laser onto a surface of an inspection target object in an inclined direction; and a detection optical system for focusing, by an objective lens, scattered light from the inspection target object due to the laser emitted as above, to thereby form an image on a solid-state imaging element, wherein the detection optical system comprises a distribution filter for controlling a polarization direction of scattered light, included in the scattered light, due to roughness of the inspection target surface and a polarization direction of scattered light, included in the scattered light, due to foreign matter or a defect on the inspection target object surface, to thereby select a polarization direction of light to be transmitted.

(2) A defect observation device, characterized by comprising a defect detection device comprising a illumination optical system for emitting laser onto a surface of an inspection target object in an inclined direction and a detection optical system for focusing, by an objective lens, scattered light from the inspection target object due to the laser emitted as above, to thereby form an image on a solid-state imaging element; and an electron microscope for conducting positioning based on positional information, obtained by the defect detection device, of a defect or foreign matter on the inspection target object surface, to thereby observe the defect or the foreign matter, the detection optical system of the defect detection device comprising a distribution filter for controlling a polarization direction of scattered light, included in the scattered light, due to roughness of the inspection target surface and a polarization direction of scattered light, included in the scattered light, due to foreign matter or a defect on the inspection target object surface, to thereby select a polarization direction of light to be transmitted.

(3) A dark-field defect inspection method in which a signal of scattered light appearing, due to illumination light emitted onto a surface of an inspection target object, from the inspection target object surface is obtained by a first sensor of a detection system and foreign matter or a defect on the inspection target object is detected based on the signal obtained by the first sensor, characterized by comprising an illumination light monitoring step of measuring either one or both of an intensity distribution and a polarization state distribution of the illumination light, a detection system monitoring step of detecting, by detecting light inputted to the detection system by a second sensor, a focusing characteristic of a detection lens and an operation state of a stage on which the inspection target object is to be placed; and a feedback control step of comparing a detection result of the illumination light monitoring step and a detection result of the detection system monitoring step with an ideal value and adjusting either one or both of the illumination light and the detection system to make a difference between each of the detection results and the ideal value equal to or less than an allowable value.

Advantageous Effects of Invention

According to the present invention, when precisely observing, by an SEM or the like, the defect detected by an optical defect inspection device, it is possible to surely place the defect as the observation target in the observation visual field of the SEM; hence, it is possible to increase the throughput of the precise inspection of the defect using the SEM and the like. Also, the device can be configured at a low cost and in a small size.

Or, it is possible to detect various defects on a substrate at a high speed and with high sensitivity.

DESCRIPTION OF EMBODIMENTS

Figure 1:
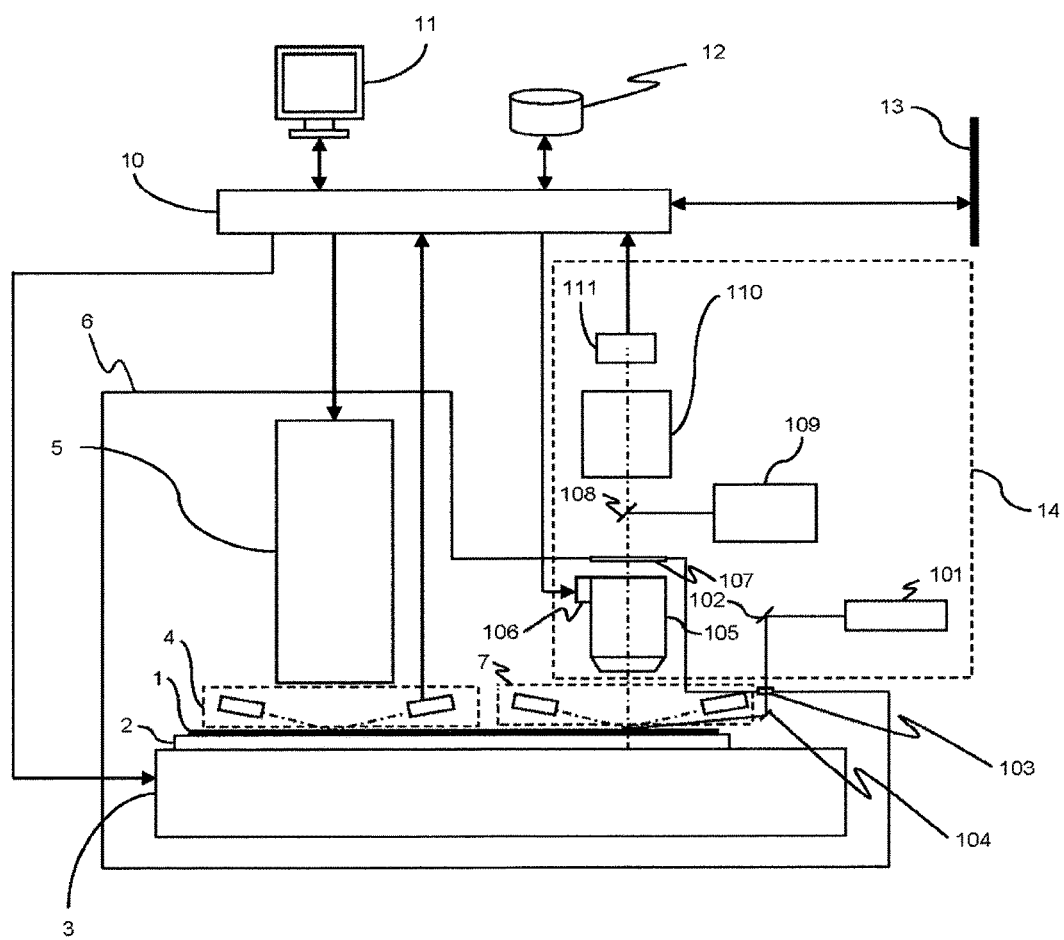
FIG. 1 is a diagram showing an example of a configuration of a defect observation device in a first embodiment of the present invention.

Next, description will be given in detail of embodiments of the present invention by referring to the drawings according to necessity.

FIG. 1 shows an example of a configuration of a defect observation device in an embodiment of the present invention. The defect observation device of this embodiment is a device to observe, in the device production process to form circuit patterns on a substrate (wafer) of a semiconductor device or the like, defects taking place during the production process, and includes a wafer 1 as an inspection target, a sample holder 2 to mount the sample thereon, a stage 3 capable of moving the sample holder 2 to move the overall surface of the sample 1 beneath a microscope, an electron microscope (to be referred to as an SEM hereinafter) 5 to precisely observe the inspection target wafer 1, an optical height detection system (to be referred to as a Z sensor hereinafter) 4 to align the focal point of the electron microscope 5 with the surface of the sample 1, an optical microscope 14 which optically re-detects a defect of the sample 1 to obtain detailed positional information of the defect on the sample 1, a Z sensor 7 to focus the optical microscope 14, a vacuum chamber 6 to accommodate the electron microscope 5 and an objective lens 105 of the optical microscope 14, a controller 10 to control the electron microscope 5, the Z sensor 4, the Z sensor 7, a height control unit 106, and a solid-state imaging element 111; a user interface 11, a database 12, and a network 13 to connect to an upper system such as an optical defect detection device.

Figure 5:
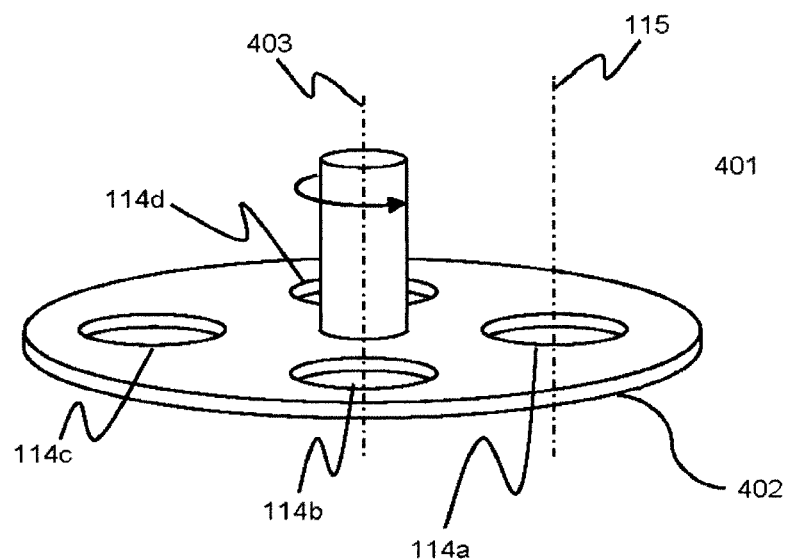
FIG. 5 is a diagram showing in detail a scheme to change over a distribution polarization element in the first embodiment of the present invention.

In addition, the optical microscope 14 includes a dark-field lighting unit 101, a light introduction mirror 102 which introduces laser emitted from the dark-field lighting unit 101 to the vacuum chamber and controls the lighting position on the surface of the sample 1, a vacuum seal window 103, a mirror 104, an objective lens 105 to gather scattered light from the sample 1 or to conduct bright-field observation, an objective height control unit 106, a vacuum seal window 107, a half-silvered mirror 108 to introduce light required for the bright-field observation, a bright-field light source 109, an imaging optical system 110 to form an image of the sample 1 onto a solid-state imaging element, a solid-state imaging element 111, and a distribution polarization element and spatial filter change-over unit 401 (reference is to be made to FIG. 5). Moreover, the stage 3, the Z sensors 4 and 7, the SEM 5, the user interface 11, the database 12, the height control unit 106, and the solid-state imaging element 111 are connected to a control system 10, and the control system 10 is coupled via the network 13 with an upper system (not shown).

In the defect observation device configured as above, particularly, the optical microscope 14 includes a function to re-detect (to be expressed as detect hereinafter) the position of a defect on the sample detected by an optical defect inspection device (not shown), by use of positional information of the defect detected by the optical defect inspection device; the height control unit 106 and the Z sensor 7 have a function as a focusing unit to conduct the sample focusing operation; the control system 10 has a function as a position correction unit to correct the defect positional information based on defect positional information of a defect detected by the microscope 14; and the SEM 5 has a function to observe the defect for which the positional information is corrected by the control system 10. The stage 3 on which an inspection target wafer 1 is mounted moves between the optical microscope 14 and the SEM 5 so that the defect detected by the optical microscope 14 is observed by the SEM 5.

The objective 105 and the height control unit 106 are installed in the vacuum chamber 6. As for the configuration of the height control unit 106, it may be configured to be moved by using, for example, a piezoelectric element; to be moved in the Z direction (the direction along the optical axis 115 of the imaging optical system 110) by use of a stepping motor and a ball screw; or to be moved in the Z direction along the linear guide by use of an ultrasonic motor and a ball screw.

The light introduction mirror 102 is employed to introduce light emitted from the illumination light source 101 into the vacuum chamber 6 as shown in FIG. 1. Incidentally, the light introduction mirror 102 may include, in order to control a lighting position on the surface of the sample 1, a mechanism which rotates about two axes including an axis along the longitudinal direction of the mirror shown and an axis perpendicular to the drawing.

Next, description will be given in detail of the respective components by referring to FIGS. 2 to 20.

Figure 2:
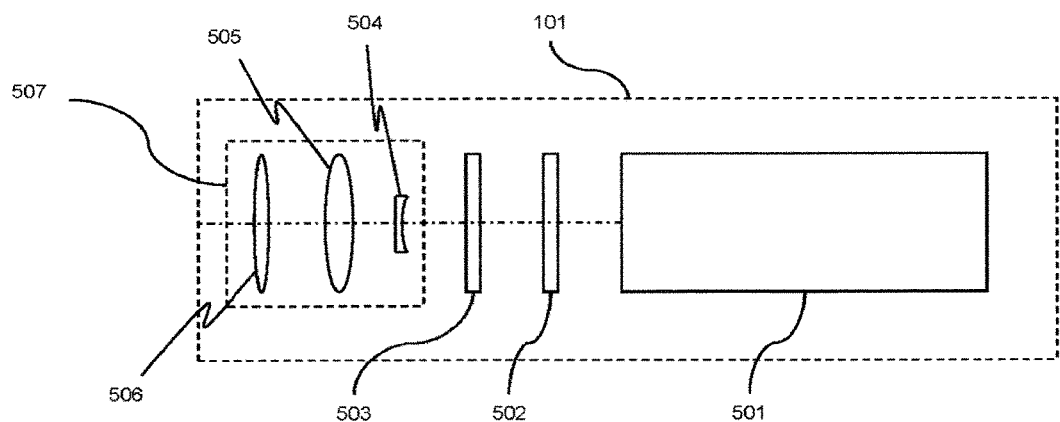
FIG. 2 is a diagram showing in detail a dark-field lighting unit in the first embodiment of the present invention.

FIG. 2 shows the dark-field lighting unit 101 in detail. The dark-field lighting unit 101 includes a illumination light source 501 to emit, for example, visible light laser, ultraviolet light laser, or vacuum ultraviolet light laser; an optical filter 502 to adjust intensity of illumination light, a wave plate 503 to adjust the polarization direction of illumination light, and a lens group 507 to focus the illumination light onto the sample 1. The lens group 507 includes a plano-concave lens 504, an achromat lens 505, and a cylindrical lens 506. In this mechanism, by selecting the lens focal distance and by adjusting the gap between lenses, the lighting area on the surface of the sample 1 may be controlled in a range from the overall visual field to the diffraction limit of the optical microscope 14; although there is employed skewed lighting due to the cylindrical lens, a circular radiation area is feasible.

The illumination light source 501 is a laser oscillator. The laser oscillator oscillates to emit, for example, visible light of 405 nm, 488 nm, and 532 nm (400 nm to 800 nm) or ultraviolet light of 400 nm or less, or vacuum ultraviolet light of 200 nm or less; and both of a continuous wave oscillation laser and a pulse oscillation laser may be employed. As for the selection method thereof, when a continuous wave oscillation laser is employed, it is not expensive and stable, and it is possible to implement a small-sized device. The wavelength of the illumination light source 501 is not restricted by the wavelengths described above. If high sensitivity is required, ultraviolet light is employed; in this situation, the objective 105, the vacuum seal window 107, the half-silvered mirror 108, and the imaging optical system 110 include optical elements or reflection-type optical elements for the ultraviolet zone of synthetic quartz or the like. If higher sensitivity is required, vacuum ultraviolet light is employed; in this situation, the objective 105, the vacuum seal window 107, the half-silvered mirror 108, and the imaging optical system 110 include optical elements or reflection-type optical elements for the vacuum ultraviolet zone of dissolved quartz or the like; further, in order to prevent absorption of the propagating vacuum ultraviolet light, the overall optical path of the microscope 14 is installed in vacuum or in, for example, nitrogen gas atmosphere. Since the object is to propagate the vacuum ultraviolet light, the gas to be filled in is not limited to nitrogen.

To emit light onto the sample 1, p-polarized laser light is employed if the sample 1 is a mirror wafer; and s-polarized laser light is used if the surface of the sample 1 is coated with a metallic thin film. Linearly polarized light of p-polarized or s-polarized light is employed to more efficiently observe scattered light to implement the observation with an appropriate S/N. That is, in the observation of a mirror wafer, if the s-polarized light is employed, the scattering power is deteriorated to reduce the absolute amount of scattered light and the efficiency is lowered; hence, the illumination of p-polarized light is suitable; on the other hand, if illumination of p-polarized light is used to observe a metallic thin film or the like, scattered light from the substrate is strong, and fine defects and fine foreign matter cannot be observed; hence, illumination of s-polarized light is suitable Further, to suppress the scattered light from the substrate, the lighting is conducted with a low elevation angle of about 10° with respect to the substrate surface. The mirror 104 includes a mechanism (not shown) to move, even when the objective 105 goes upward or downward, together with the objective to thereby light the visual field of the objective 105. Or, the mirror 104 may include an independently movable mechanism (not shown) to change the lighting position in the visual field of the objective 105.

Figure 3:
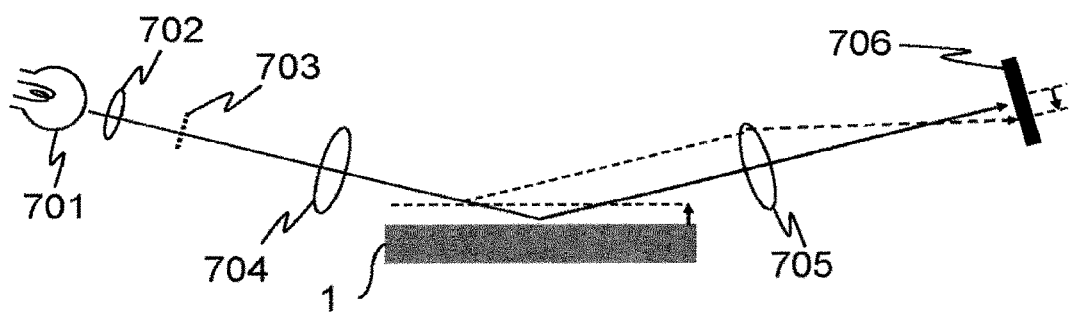
FIG. 3 is a diagram showing in detail an optical height detection device in the first embodiment of the present invention.

FIG. 3 shows the Z sensor 4 or 7. The Z sensor 4 or 7 includes a light source 751 to emit height measuring light, a slit 703, a focusing lens 702 to focus the height measuring light emitted from the lighting unit 751 onto the slit 703, an imaging lens 704 to form an image (an image of the slit 703) of light having passed the slit 703 as the height measuring light, on the surface of the sample 1; a focusing lens 705 to focus the height measuring light reflected by the sample 1, and a detector 706 to detect the height measuring light focused by the focusing lens 705 to convert it into an electric signal. Information of the height measuring light converted by the detector 706 into an electric signal is sent to the control system 10 for the calculation of the height. Incidentally, as the detector 706, there is employed a two-dimensional CCD or line sensor or a 2-division or 4-division position sensor.

Figure 4:
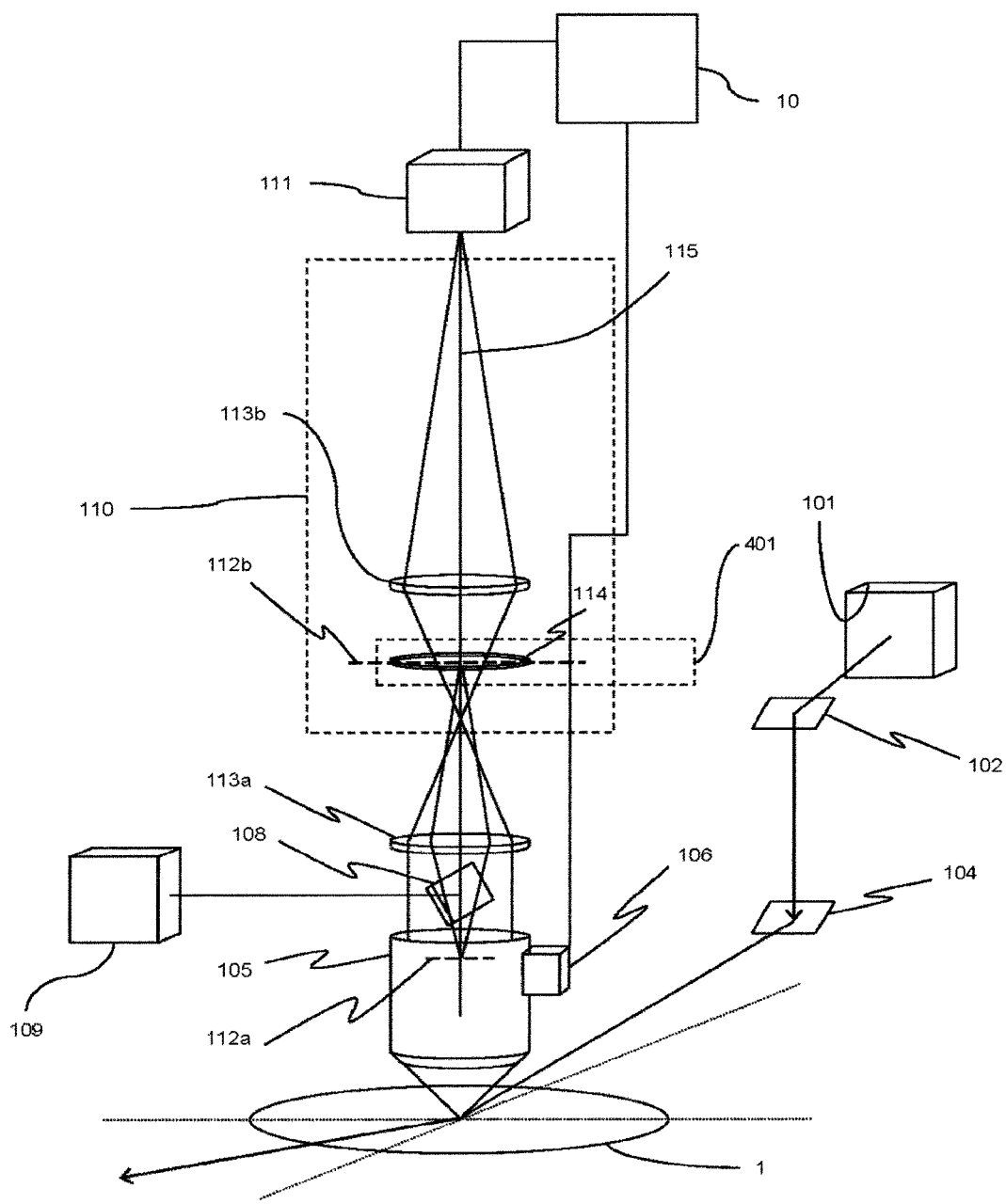
FIG. 4 is a diagram showing in detail an optical microscope in the first embodiment of the present invention.

FIG. 4 shows in detail the configuration of the optical microscope 14. The optical microscope 14 includes a dark-field lighting unit 101, a light introduction mirror 102, a mirror 104, an objective 105, a height control unit 106, a half-silvered mirror 108, a bright-field light source 109, an imaging optical system 110, and a solid-state imaging element 111. The imaging optical system 110 includes a lens 113a to obtain a pupil plane 112a of the objective 105, a lens 113b to focus an image, and a filter unit 114 to be inserted in the obtained pupil plane 112b. An example of the filter unit 114 is a distribution polarization element. According to the present embodiment, the configuration of the filter unit 114 makes it possible that a plurality of distribution polarization elements having different characteristics are held by a holder 401 (four kinds thereof 114a to 114d in the example shown in FIG. 5) in the filter unit 114 and a changeover operation is conducted between the distribution polarization elements 114a to 114d for the insertion thereof in the pupil plane 112b. Further, the height control unit 106 and the solid-state imaging element 111 are connected to the control system 10.

The lens 113a is used to draw the pupil plane 112 of the objective 105 to the outside to form it in the imaging optical system 110; by driving the holder 402, a distribution polarization element selected from the distribution polarization elements 114a to 114d held by the holder 402 is inserted in the pupil plane 112 drawn into the imaging optical system 110. The holder 402 may insert, in place of the distribution polarization elements 114a to 114d, a spatial filter or a distribution polarization element formed on the spatial filter. The lenses 113a and 113b are paired to focus an image of the sample 1 onto the detection surface of the solid-state imaging element 111.

The ratio between reflection and transmission may be arbitrarily set in the half-silvered mirror 108. However, when the light intensity from the bright-field light source 109 is sufficiently secured, it is favorable to configure such that much scattered light from the defect is fed to the imaging optical system 110 and the solid-state imaging element 111.

For the bright-field light source 109, a lamp or a laser may be used. When a laser is used, it is possible, by substituting a dichroic mirror for the half-silvered mirror 108, to make the lighting brighter and to feed much scattered light to the solid-state imaging element 111. Or, in the dark-field observation, there may be disposed a mechanism (not shown) to remove the half-silvered mirror 108 from the optical axis 115 of the imaging optical system 110 and the objective 105. In such situation, much scattered light can be advantageously fed to the solid-state imaging element 111.

FIG. 5 shows a changeover unit 401 to conduct a changeover operation, on the optical axis 115 of the imaging optical system 110, for the distribution polarization elements 114a to 114d inserted in the pupil plane 112b of the objective 105. The unit 401 includes in its configuration a holder 402 to arrange a plurality of distribution polarization elements 114a to 114d having different characteristics and a rotation drive unit 403 for an axis to rotate the holder 402. The holder 402 is a unit to conduct a changeover operation to select either one of the distribution polarization elements 114a to 114d according to the kind of the fine defect to be detected. On the other hand, in the bright-field observation, to avoid disturbance in the obtained image, the holder 402 is placed for the observation at a position other than the places where the distribution polarization elements 114a to 114d are arranged. Or, the position is changed to a place where a sheet of parallel planar glass with thickness equal to that of the distribution polarization elements 114a to 114d is installed. The sheet of parallel planar glass with thickness equal to that of the distribution polarization elements 114a to 114d is installed to avoid an event in which when the distribution polarization elements 114a to 114d are removed, the optical path length changes and the image of the sample 1 is not focused onto the solid-state imaging element 111. Or, without installing the sheet of parallel planar glass, there may be employed a mechanism in which the image is focused onto the solid-state imaging element 111 by adjusting the position of the image focusing lens 113b or the solid-state imaging element 111.

In conjunction with the embodiment shown in FIG. 5, description has been given of a situation in which a plurality of distribution polarization elements 114a to 114d having different characteristics are installed in the holder 402; however, it is also possible that in place of the plural distribution polarization elements 114a to 114d, a plurality of spatial filters having different characteristics are installed in the holder 402 to conduct the changeover operation. In a situation in which the spatial filters are installed in the holder 402 and the bright-field observation is conducted, to avoid disturbance in the obtained image, the position of the holder 402 is set to other than the place where the spatial filters are installed for the observation. Or, the changeover is carried out to a place in the holder 402 where a sheet of parallel planar glass having thickness equal to that of the spatial filters is installed. Or, or, without installing the sheet of parallel planar glass, there may be used a mechanism in which the image is focused onto the solid-state imaging element 111 by adjusting the position of the image focusing lens 113b or the solid-state imaging element 111.

Figure 6:
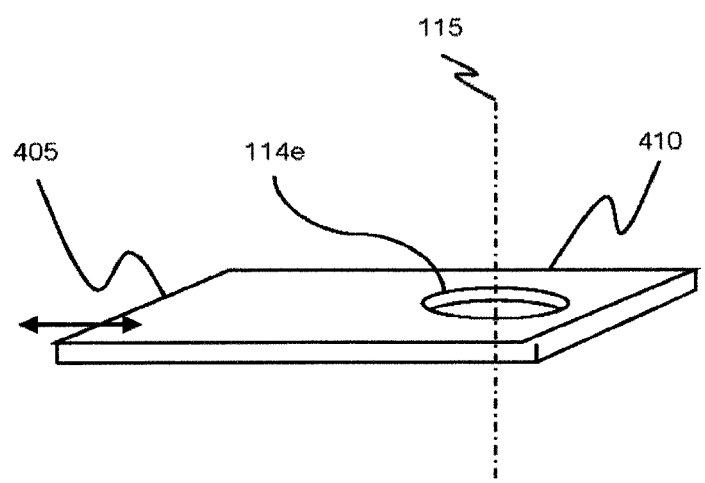
FIG. 6 is a diagram showing in detail another example of the scheme to change over a distribution polarization element in the first embodiment of the present invention.

FIG. 6 shows another embodiment of the mechanism to move the distribution polarization elements 114a to 114d. The mechanism 410 is a mechanism in which the distribution polarization element holder 405 slides to move a distribution polarization element 114e onto and from the optical axis 115 of the imaging optical system 110. Although FIG. 6 shows a situation in which one distribution polarization element 114e is used, there may be included a plurality of distribution polarization elements. Further, also in this embodiment, a spatial filter may be used in place of the distribution polarization element 114e. In addition, it is possible to combine the distribution polarization element 114 with the spatial filter.

Figure 7:
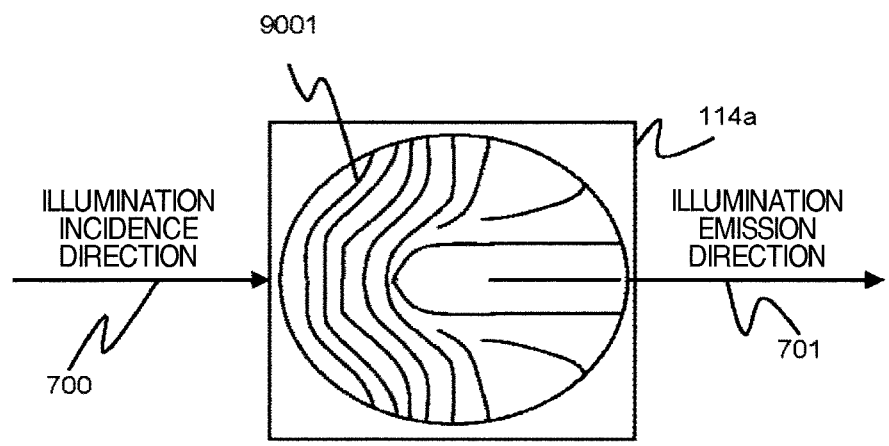
FIG. 7 is a diagram showing an example of the distribution direction of the transmission axis of a distribution polarization element to be inserted in an optical microscope pupil plane 112 in the first embodiment of the present invention.
Figure 7:
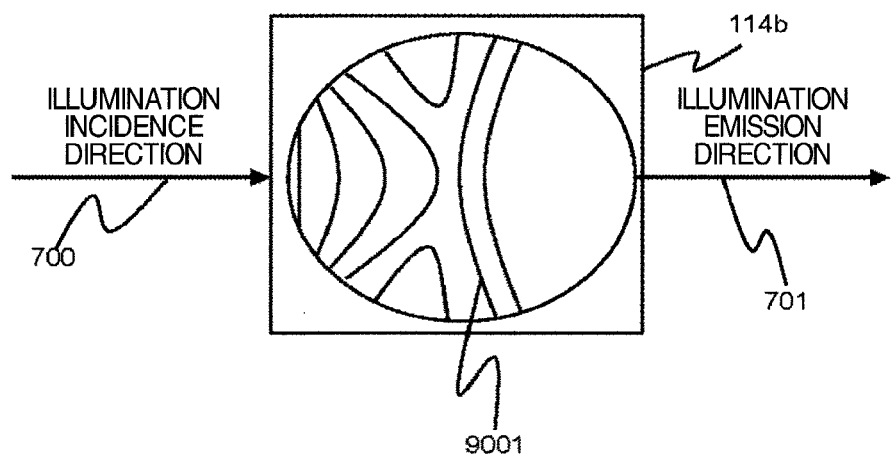

In FIG. 7, (a) and (b) show polarization characteristic examples of the distribution polarization elements 114a and 114b to be inserted in the pupil plane 112b in the imaging optical system 110. 1002 indicates a pupil outer circumference and 9001 indicates a transmission polarization axis direction. The distribution polarization elements 114a and 114b have a diameter of the size at least covering the overall pupil plane 1121002, and the transmission polarization axis direction 9001 varies at respective points of the distribution polarization elements 114a and 114b.

In the plane, the distribution polarization elements 114a and 114b in which the transmission polarization axis direction 9001 is distributed are implemented by linking linear polarization elements together, by using photonic crystal, by using wire grid polarizer, or by combining liquid crystal with a polarization element. Here, the photonic crystal is an optical element including fine structures in which the refractive index varies with a period of a light wavelength or less, and the wire grid polarizer is a polarization element in which electrically conductive fine wires are periodically arranged to provide optical anisotropy.

Figure 8:
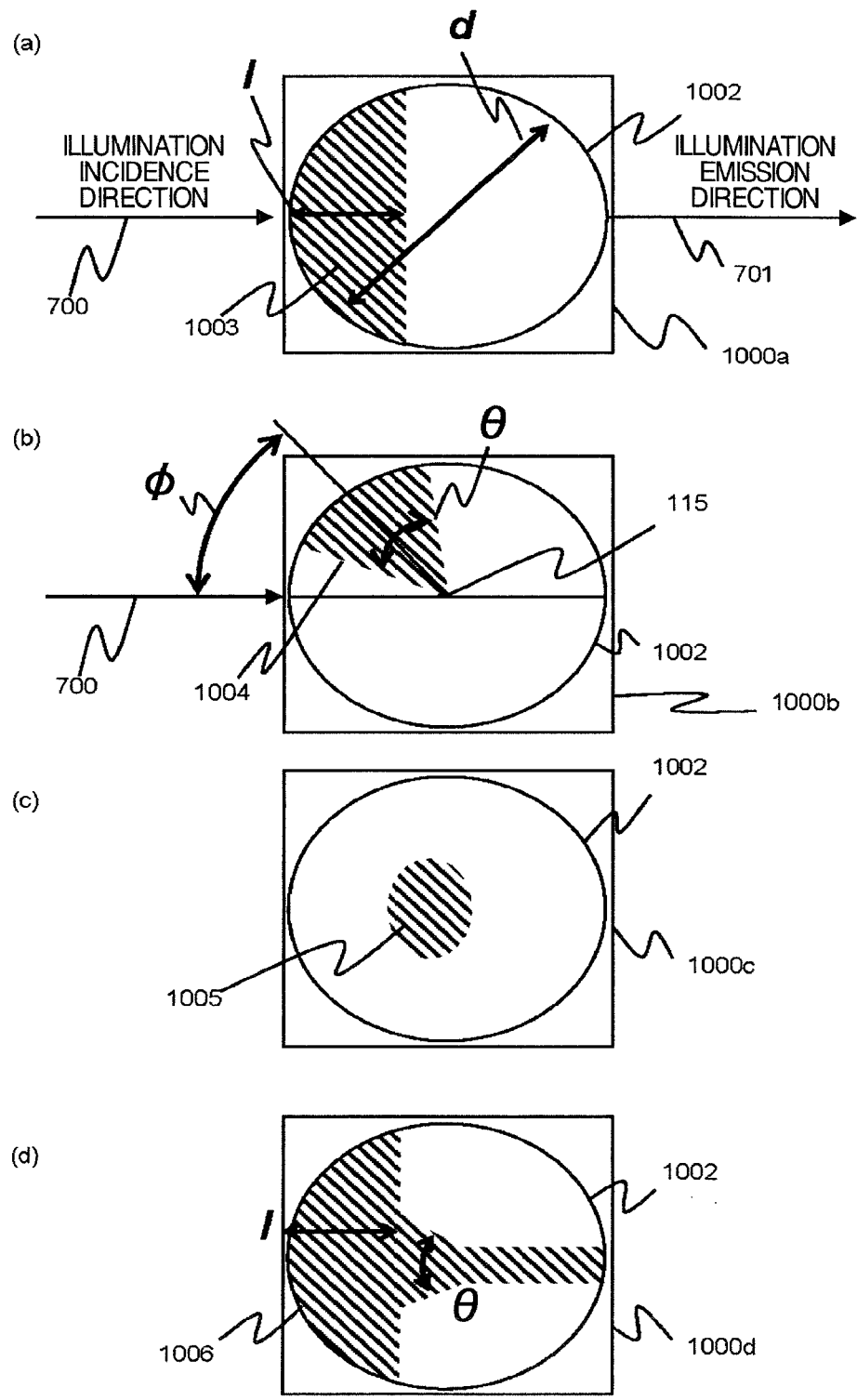
FIG. 8 is a diagram showing an example of the contour of the spatial filter to be inserted in the optical microscope pupil plane 112 in the first embodiment of the present invention.

In FIG. 8, (a) to (d) show an example in which in place of the distribution polarization elements 114a to 114d exemplified as filters 114 in FIG. 5, spatial filters 1000a to 1000d are inserted in the pupil plane 112. In this example, in the changeover mechanism 401 shown in FIG. 5, the spatial filters 1000a to 1000d having different contours are installed in place of the plural distribution polarization elements 114a to 114d. In (a) to (d) of FIG. 8, 1002 indicates a pupil outer circumference and 1003 to 1006 indicate light block zones.

The value of I of the light block zone 1003 in the spatial filter 1000a shown in FIG. 8(a) and the values of θ and φ of the light block zone 1004 in the spatial filter 1000b shown in FIG. 8(b) are determined based on the scattered light intensity distribution obtained through scattered light simulation or actual measurement of scattered light.

Figure 9:
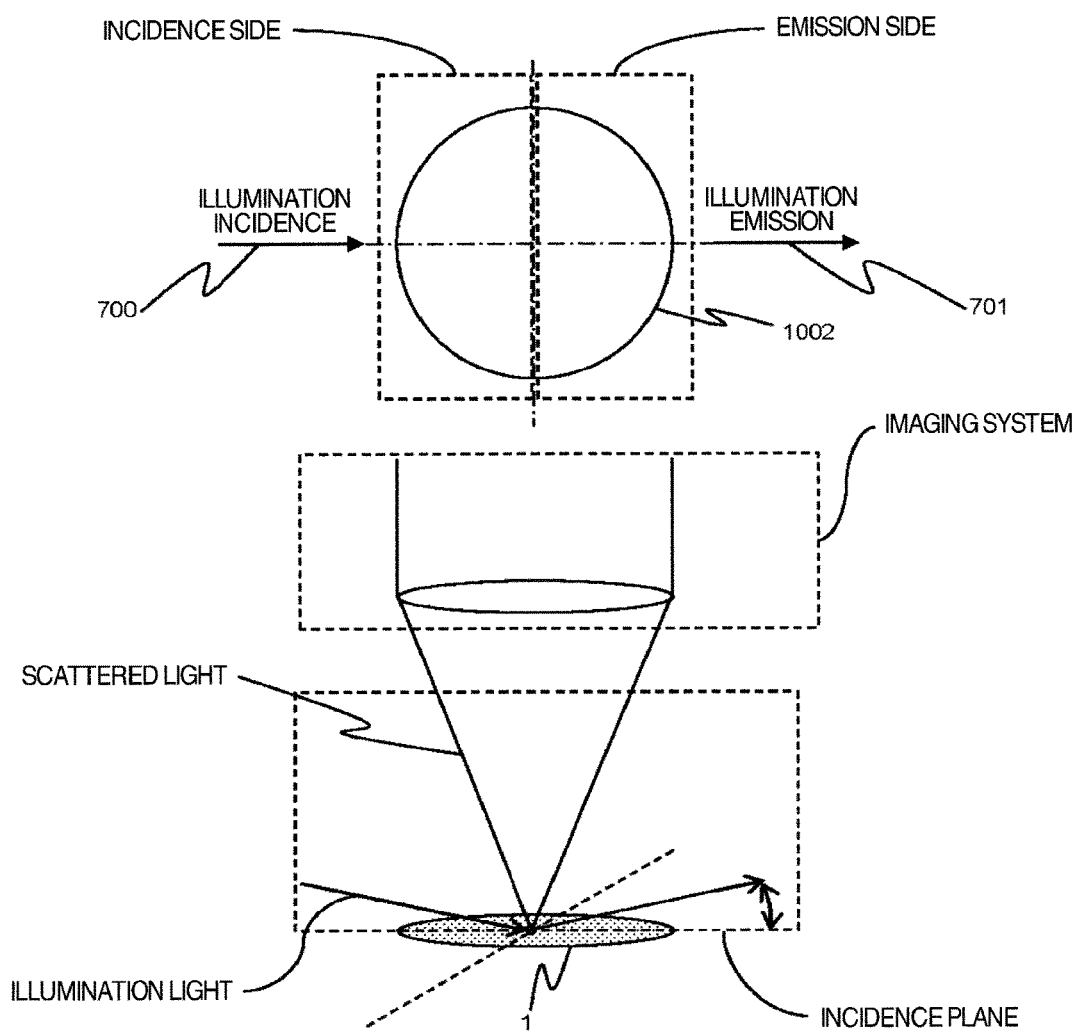
FIG. 9 is a diagram to explain scattered light simulation conducted to determine an optical characteristic of the distribution polarization element and the spatial filter in the first embodiment of the present invention.

Description will be given of an example of the method of determining the transmission polarization axis direction 9001 and the value of I or the values θ and φ of the spatial filter contour by referring to FIGS. 9 and 10.

First, description will be given of the scattered light simulation and terms required to determine the transmission polarization axis direction 9001 of the distribution polarization elements 114a to 114d by referring to FIG. 9. In the scattered light simulation, laser as the illumination light is emitted onto the sample 1 from above in a skewed direction and then light scattered by fine foreign matter or fine defects placed on the sample 1 is used to calculate the intensity distribution and the polarization distribution of scattered light on a surface nearest to the sample 1 of the optical element nearest to the sample 1 of the imaging optical system. As for the polarized light of scattered light, it is assumed that the polarized light parallel to the incidence plane is p-polarized light and the polarized light with polarization perpendicular to that of the p-polarized light is s-polarized light. Additionally, in the plane in which the intensity distribution or the polarization distribution is obtained, the half thereof on the side of the illumination incidence 700 is referred to as an incidence side and the remaining half thereof is referred to as an emission side hereinafter.

Next, description will be given of a method of determining the polarized light transmission axis distribution $h(r,\theta)$ of the distribution polarization elements 114a to 114d and the light block zone $g(r,\theta)$ of the spatial filters 1000a to 1000d.

First, through scattered light simulation, there are obtained the scattered light intensity distribution $fs(r,\theta)$ of scattered light from fine defects or fine foreign matter to be detected with high sensitivity, the p-polarized light distribution $psp(r,\theta)$ and the s-polarized light distribution $pss(r,\theta)$ of the scattered light as well as the scattered light intensity distribution $fN(r,\theta)$ of scattered light from fine concavity and convexity on the substrate surface, and the p-polarized light distribution $pNp(r,\theta)$ and the s-polarized light distribution $pNS(r,\theta)$ of the scattered light.

The polarized light transmission axis direction distribution $h(r,\theta)$ of the distribution polarization element 114 is determined as a polarization axis distribution which most blocks scattered light from fine concavity and convexity on the substrate surface, that is, $h(r,\theta)$ which minimizes Π of (MATH.1); or, a polarization axis distribution which most transmits scattered light from a fine defect or fine foreign matter, that is, $h(r,\theta)$ which maximizes Λ of (MATH.2); or, a polarization axis distribution which blocks the scattered light from fine concavity and convexity on the substrate surface and which transmits scattered light from a fine defect or fine foreign matter, that is, $h(r,\theta)$ which maximizes Ω of (MATH.3).

$$\prod = \int \sqrt{|p_{NP}(r,\theta) \cdot h(r,\theta)|^2 + |p_{NS}(r,\theta) \cdot h(r,\theta)|^2}\, drd\theta \quad \text{[MATH. 1]}$$

$$\Lambda = \int \sqrt{|p_{SP}(r,\theta) \cdot h(r,\theta)|^2 + |p_{SS}(r,\theta) \cdot h(r,\theta)|^2}\, drd\theta \quad \text{[MATH. 2]}$$

$$\Omega = \frac{\int \sqrt{|p_{SP}(r,\theta) \cdot h(r,\theta)|^2 + |p_{SS}(r,\theta) \cdot h(r,\theta)|^2}\, drd\theta}{\int \sqrt{|p_{NP}(r,\theta) \cdot h(r,\theta)|^2 + |p_{NS}(r,\theta) \cdot h(r,\theta)|^2}\, drd\theta} \quad \text{[MATH. 3]}$$

On the other hand, the method to determine the light block zone $g(r,\theta)$ of the spatial filter is, for example, a method in which the light block zone $g(r,\theta)$ is optimized to maximize Ψ represented by (MATH.4).

$$\Psi = \frac{\int f_S(,\theta) \times g(r,\theta) dr d\theta}{\int f_N(,\theta) \times g(r,\theta) dr d\theta} \quad \text{[MATH. 4]}$$

More simply, there may also be used a method wherein the spatial filter has a distribution to block light in the zone in which the scattered light from the fine concavity and convexity on the substrate surface is strong or a method wherein the spatial filter having a distribution to block light in the zone in which the scattered light from the fine concavity and convexity on the substrate surface is strong is combined with the linear polarization element.

Next description will be given of the method of determining the polarized light transmission axis direction distribution of the distribution polarization elements 114a to 114d and the light block characteristic of the spatial filters 1000a to 1000d by specifically using an example of scattered light simulation results.

Figure 10:
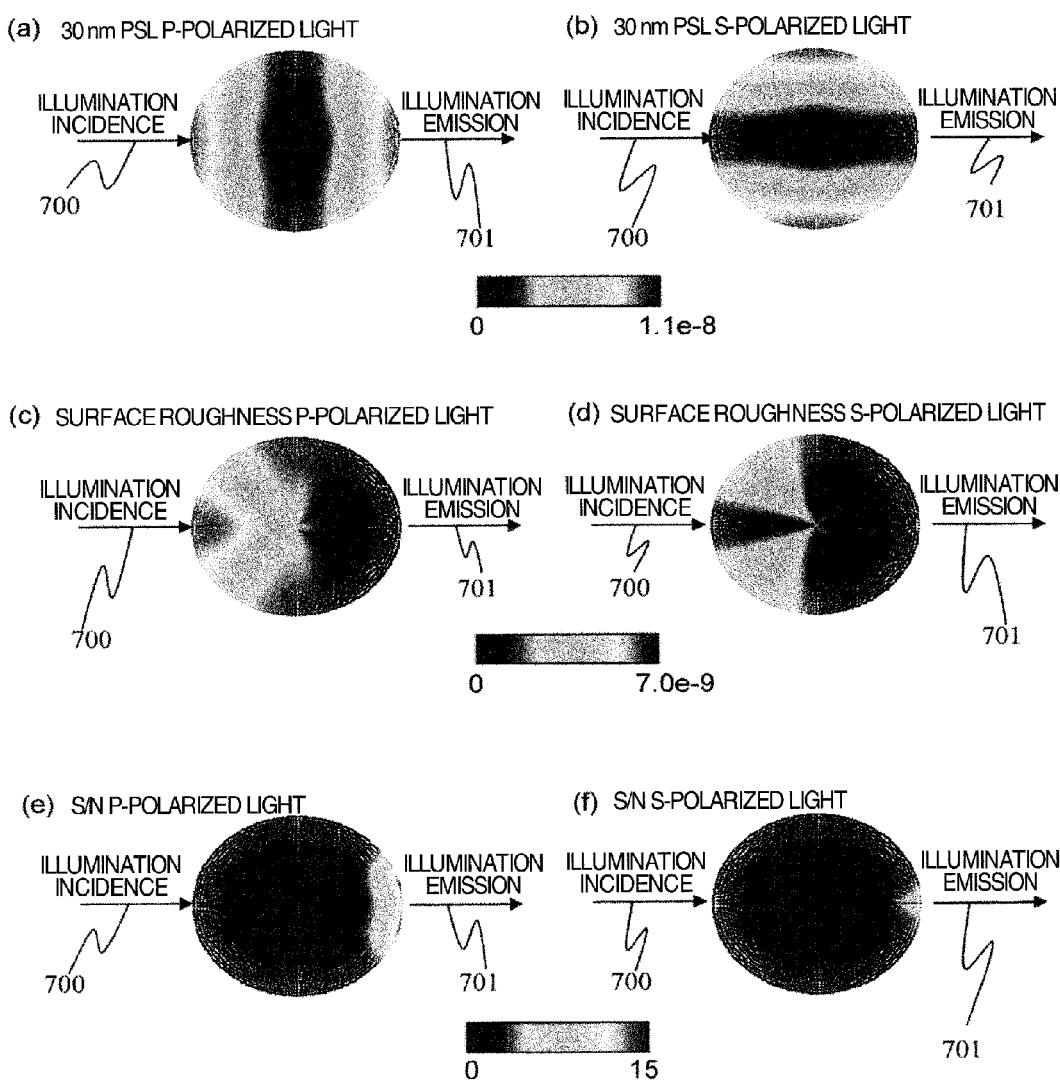
FIG. 10 is a diagram showing an example of results of the scattered light simulation conducted to determine an optical characteristic of the distribution polarization element and the spatial filter in the first embodiment of the present invention.

In FIGS. 10, (a) to (f) show examples of the scattered light polarization distribution, calculated by scattered light simulation, of scattered light from polystyrene latex (to be referred to as PSL hereinafter) as fine depressions, projections, and a fine particle on a surface of the inspection target wafer 1.

FIG. 10(a) shows the distribution of p-polarized light of the scattered light (light wavelength 400 nm) by 30 nm PSL, FIG. 10(b) shows the distribution of s-polarized light of the scattered light by 30 nm PSL, FIG. 10(c) shows the distribution of p-polarized light of the scattered light by the concavity and convexity on a surface of the inspection target wafer 1, FIG. 10(d) shows the distribution of s-polarized light of the scattered light by the fine concavity and convexity on a surface of the inspection target wafer 1, FIG. 10(e) shows the p-polarized light distribution of the ratio (to be indicated as S/N hereinafter) between the scattered light from PSL and that from the concavity and convexity on a surface of the inspection target wafer 1, and FIG. 10(f) shows the s-polarized light distribution of S/N.

From FIG. 10(a) and FIG. 10(b), it can be seen that in the scattered light by PSL, the p-polarized light is strong in the outer circumferential units of the pupil plane 112 on the illumination incidence 700 side and the illumination emission 701 side; and the s-polarized light is strong in the outer circumferential units of the pupil plane 112 in the direction vertical thereto. On the other hand, from FIG. 10(c) and FIG. 10(d), it can be seen that in the scattered light from the concavity and convexity on a surface of the inspection target wafer 1, the p-polarized light is strong on the illumination incidence 700 side; and in the direction of the illumination incidence side 700 direction ±45°, the p-polarized light is equal in strength to the s-polarized light, that is, it is 45°-polarized light. Further, from FIG. 10(c) and FIG. 10(d), it can be seen that on the illumination emission 701 side, the scattered light taking place from the concavity and convexity on a surface of the inspection target wafer 1 is very weak.

FIGS. 10(e) and 10(f) show S/N calculated based on FIGS. 10(a) to 10(d). FIG. 10(e) shows S/N of p-polarized light and FIG. 10(f) show S/N of s-polarized light.

Figure 11:
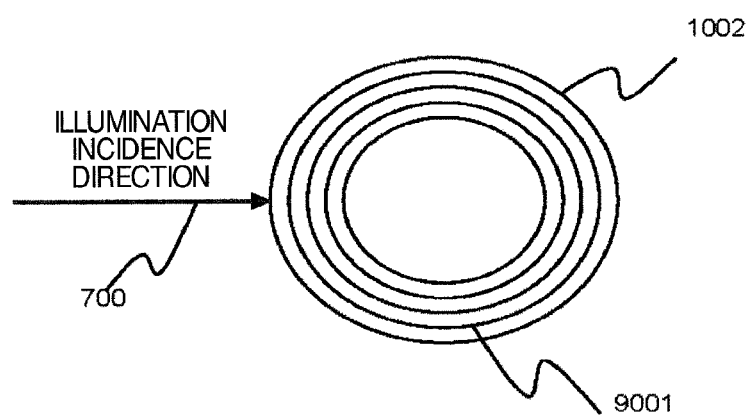
FIG. 11 is a diagram showing an example of the distribution direction of the transmission axis of a distribution polarization element to be inserted in the optical microscope pupil plane 112 in the first embodiment of the present invention.

The distribution polarization element 114 configured to have the distribution of the polarized light transmission axis direction 9001 to block the scattered light from the concavity and convexity on a surface of the inspection target wafer 1 can be determined as exemplified in FIG. 7(a) and FIG. 7(b), according to, for example, FIG. 10(c) and FIG. 10(d). FIG. 7(a) and FIG. 7(b) exemplify the distribution contours of the polarized light transmission axis direction 9001 of the distribution polarization element 114 in which 1002 indicates the edge of the distribution polarization element and 9001 indicates the polarized light transmission axis direction. Over the line of intersection between the incidence plane of the illumination light and the pupil plane 112 and in the neighborhood thereof, the s-polarized light is transmitted; in the direction skewed ±45° with respect to the direction of the illumination incidence 700, the ±45°-polarized light is transmitted; on the side of the illumination emission 701 of the pupil plane 112, the p-polarized light is transmitted; and in the pupil central unit and the pupil periphery in the direction vertical to the illumination incidence, the s-polarized light transmission distribution is obtained. Further, the distribution contour of the polarized light transmission axis direction 9001 to gather the scattered light from PSL to the maximum extent is determined based on the scattered light distribution characteristic shown in FIG. 10(a) and FIG. 10(b); the contour is formed, for example, as the polarized light transmission axis direction 9001 in a concentric shape parallel to the outer circumference of the pupil plane 112 as shown in FIG. 11.

Also, the distribution contour of the polarized light transmission axis direction 9001 to transmit the polarized light in which the ratio of the scattered light from the fine defect or fine foreign matter to the scattered light from the fine concavity and convexity on a surface of the inspection target wafer 1 is high can be determined using FIG. 10(e) and FIG. 10(f); the contour is formed, for example, as the polarized light transmission axis direction 9001 to transmit only the p-polarized light in the pupil outer circumference unit on the side of the illumination emission 701.

Incidentally, the intensity distribution and the polarization distribution of the scattered light vary depending on the contour and the size as well as optical characteristics such as the refractive index of the fine foreign matter or a fine defect to be detected; hence, the polarization distribution of the distribution polarization element to be inserted in the pupil plane 112 of the imaging optical system is not limited to the distribution contours of the polarized light transmission axis direction 9001 shown in FIG. 7(a) and FIG. 7(b).

In FIG. 8, (a) to (d) show examples of the contour of the spatial filters 1000a to 1000d. It is only required that the diameter d of the spatial filters 1000a to 1000d is equal to or more than the pupil diameter, and the centers of the spatial filters 1000a to 1000d are arranged to match the optical axis 115 of the imaging optical system 110, and there are included light block zones 1003 to 1006. FIG. 8(a) is the spatial filter 1000a in which the edge of the light block zone 1003 is appropriately vertical to the incidence direction 700 of the dark-field lighting; in the example of FIG. 8(a), I<d/2 and the light is blocked in a part of the incidence side of the pupil in this configuration. The spatial filter 1000a shown in FIG. 8(a) may be used to block p-polarized light of scattered light taking place due to fine concavity and convexity on a surface of the inspection target wafer 1 shown in FIG. 10(c), and it functions, by setting substantially I=d/2, as a spatial filter to block both of the p-polarized light and the s-polarized light of the scattered light taking place due to the fine concavity and convexity on a surface of the inspection target wafer 1. However, depending on the contour and the size of the fine defects or the fine foreign matter as the observation target or the sensitivity required for the measurement, it is also possible to use a spatial filter set as I>d/2. For example, when it is desired to selectively detect an area having a high N/S as shown in FIG. 10(e), I is substantially 0.8d.

FIG. 8(*b*) shows an example of the spatial filter 1000*b* including a light block zone 1004 to block light in an area having the shape of a sector with an azimuth of φ and a vertex angle of θ in the pupil. In the spatial filter 1000*b* of FIG. 8(*b*), the vertex of the sector of the light block zone 1004 is aligned with the center (the optical axis 115 of the imaging optical system 110) of the pupil plane 112; however, it is not necessarily required that the vertex of the light block zone 1004 matches the optical axis 115 of the imaging optical system 110. The spatial filter 1000*b* shown in FIG. 8(*b*) is an example of the spatial filter to block only the p-polarized light of the scattered light due to the fine concavity and convexity on a surface of the inspection target wafer shown in FIG. 10(*c*). Incidentally, depending on the contour and the size of the fine defects or the fine foreign matter as the observation target or the sensitivity required for the measurement, the angle θ is determined and is freely selectable in the range of 0°<θ<360°.

Additionally, as shown in FIG. 8(*c*), there may be used a spatial filter 1000*c* including a light block zone 1005 in the form of an island in the pupil. Or, there may be used a spatial filter 1000*d* including a light block zone 1006 in the form of a combination of the spatial filters 1000*a* to 1000*c* shown in (a) to (c) of FIG. 8.

The light block zones 1003 to 1006 of the spatial filters 1000*a* to 1000*d* to be inserted in the pupil plane 112*b* are configured by using, for example, a light block plate of a metallic plate or the like processed to have a black frosted surface or a combination of a polarization element and liquid crystal or a digital mirror array.

Figure 12:
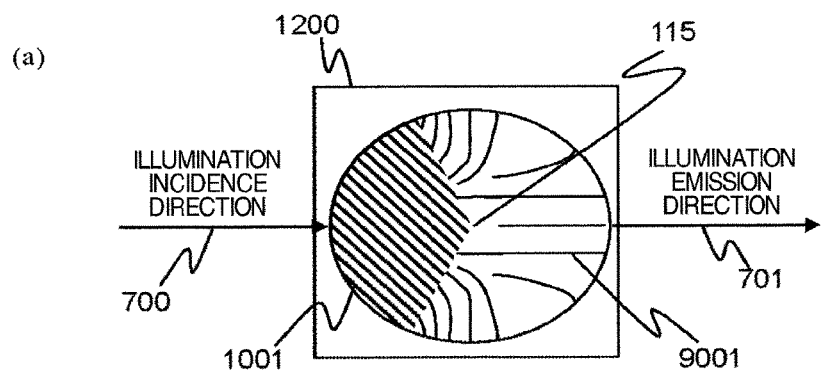
FIG. 12 is a diagram showing an example in which the distribution polarization element and the spatial filter to be inserted in the optical microscope pupil plane 112 are formed on one substrate in the first embodiment of the present invention.
Figure 12:
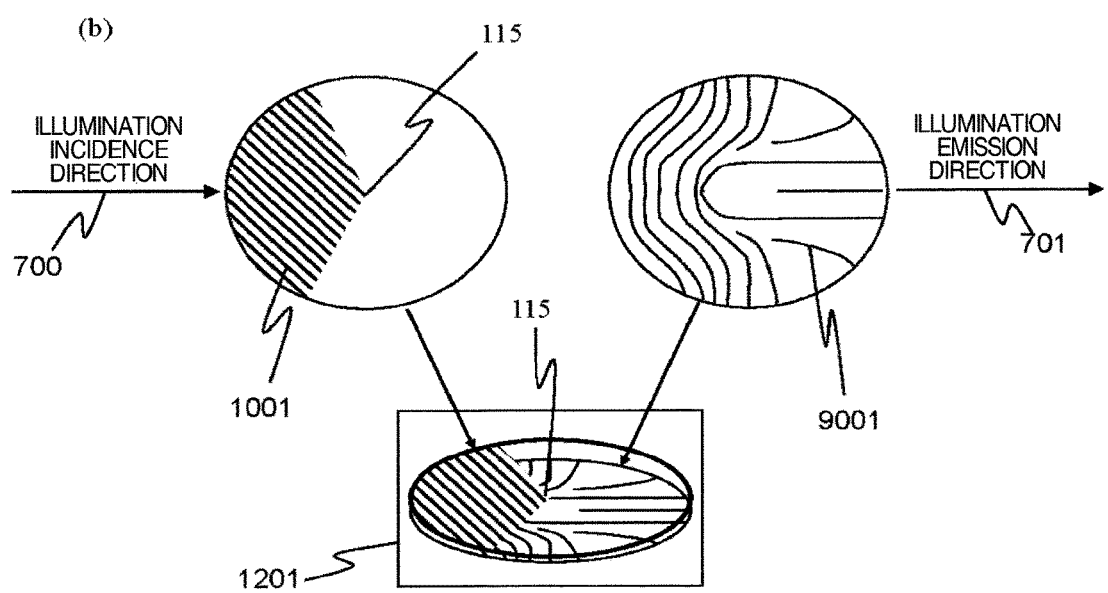

Either one of the distribution polarization elements 114*a* to 114*d* and either one of the spatial filters 1000*a* to 1000*d* to be inserted in the pupil plane 112*b* may be formed on one substrate; FIG. 12(*a*) shows such an example as a composite filter 1200. In the composite filter 1200 shown in FIG. 12(*a*), 115 indicates an optical axis of an imaging optical system 110, 1001 is a light block zone, and 9001 is a transmission polarization axis direction. The composite filter 1200 which is exemplified in FIG. 12(*a*) and in which spatial filters and distribution polarization elements are formed on one substrate is a combination of distribution polarization elements having a polarization distribution to block p-polarized light of the scattered light from the fine concavity and convexity on a surface of the inspection target wafer 1 and to selectively obtain the scattered light from PSL. This is a combination of the polarized light transmission axis distribution h(r,θ) of the distribution polarization elements and the light block zone g(r,θ) of the spatial filters to maximize both of Ω of (MATH.3) and Ψ of (MATH.4). As for a method of forming, on one substrate, either one of the distribution polarization elements 114*a* to 114*d* and either one of the spatial filters 1000*a* to 1000*d*, there may be considered photonic crystal, a combination of a polarization element and liquid crystal, a combination of a light block plate and a wire grid polarizer, and the like.

Either one of the distribution polarization elements 114*a* to 114*d* and either one of the spatial filters 1000*a* to 1000*d* to be inserted in the pupil plane 112*b* may be combined with each other at the same time; FIG. 12(*b*) shows an example as a composite filter 1201. In the composite filter 1201 shown in FIG. 12(*b*), 115 indicates an optical axis of the imaging optical system 110, 1001 is a light block zone, and 9001 is a transmission polarization axis direction.

Incidentally, the intensity distribution of the scattered light varies depending on the contour and the size as well as optical characteristics such as the refractive index of the fine foreign matter or fine defects to be detected; hence, the light block characteristic of the spatial filter to be inserted in the pupil plane 112*b* of the imaging optical system is not limited to the contours shown in (a) and (b) of FIG. 8. It is only necessary that the spatial filter has a contour to block the scattered light component in association with the distribution characteristic of the scattered light due to the fine concavity and convexity on a surface of the inspection target wafer 1.

Description will be given of operation in the configuration of the defect observation device shown in FIG. 1. First, the sample 1 is transported via a load lock chamber, not shown, onto the sample holder 2 in the vacuum chamber 6. And the sample 1 is moved, under control of the stage 3, into the visual field of the optical microscope 14. At this point, it is likely that the sample 1 is apart from the position of the focus of the optical microscope. If the height of the sample 1 is apart from the position of the focus, the objective 105 and the mirror 104 are moved in the Z direction by use of the height control unit 106 such that the sample 1 is set to the position of the focus of the optical microscope 14. The method of determining the quantity of movement in the Z direction will be described later.

To observe defects on the wafer 1 mounted on the stage 3 of the defect observation device shown in FIG. 1 by use of positional information of defects on the wafer 1 detected by another defect inspection device (not shown), it is required to conduct wafer alignment to match the reference position of the wafer 1 with the reference of the stage 3. The wafer alignment is conducted by using bright-field observation images. At bright-field detection, illumination light is emitted from the bright-field lighting unit 109, and the light is reflected by the half-silvered mirror 108 to be radiated through the objective 105 onto the sample 1. Reflected light from the sample 1 passes the imaging optical system 110 to form an image on the solid-state imaging element 111. Here, the bright-field lighting unit 109 is, for example, a lamp. In the bright-field observation of the present embodiment, the filter 114 to be inserted in the imaging optical system 110 is replaced by a sheet of parallel planar glass having the same thickness. If the alignment is conducted using the outer contour of the sample 1 (for example, an orientation flat or notch if the sample 1 is a wafer), it is only required to carry out the process by obtaining images at the positioning point and several points of the outer contour of the sample 1.

After the wafer alignment, according to the positional information of the defects detected by the defect inspection device, the defect is moved into the visual field of the optical microscope 14 to obtain a defect image in the dark-field observation method of the optical microscope 14. In the operation, for each defect position, if the height of the sample 1 is apart at each defect position from the position of the focus of the optical microscope 14, the focusing is carried out in a method, which will be described later.

Next, the dark-field observation method will be described. In the dark-field observation method, illumination light is emitted from the lighting unit 101. Although the illumination light may be laser light or lamp light, the laser light is desirably employed since higher illuminance is obtained by the laser light.

The light emitted from the lighting unit 101 is reflected by the light introduction mirror 102 and its direction is changed to the Z direction and the light is fed through the vacuum seal window 103 into the vacuum chamber 6, and its direction is changed by the mirror 104, and the light is emitted onto a surface of the sample 1 existing at the position of the focus of the optical microscope 14. The light scattered by the sample 1 is gathered by the objective 105 and is fed to the imaging optical system 110 to form an image on the imaging position of the solid-state imaging element 111, and the image is converted into an electric signal by the solid-state imaging element 111 to be sent to the control system 10.

Figure 13:
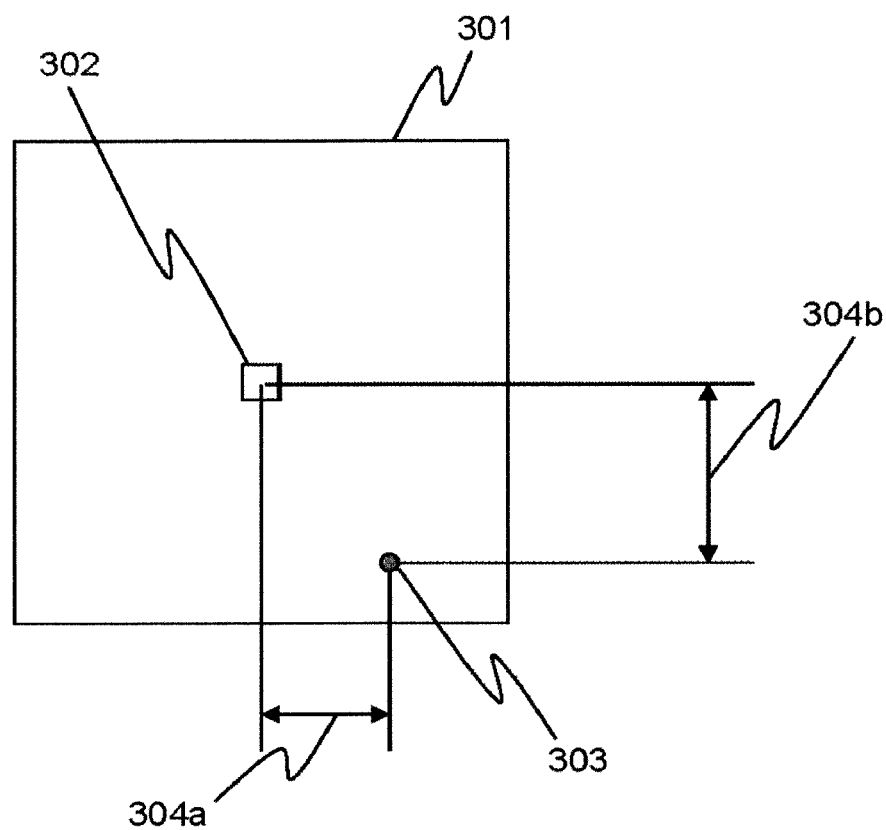
FIG. 13 is a diagram showing a positional shift quantity calculation image of a defect obtained through dark-field observation by the optical microscope in the first embodiment of the present invention.

The image obtained in the dark-field observation method of the optical microscope 14 is stored as a gray-scale image or a color image in the control system 10. In the control system, as shown in FIG. 13, positional shift quantities 304*a* and 304*b* of the defect 302 relative to the center position of the visual range 302 of the SEM 5 are calculated, and the shift quantities are registered as coordinate correction values. Thereafter, by using the coordinate correction values, the sample 1 is moved by the stage 3 such that the defect 303 is in the visual field 302 of the SEM 5, to thereby observe the defect. The image of the observed defect is transmitted to the control system 10 to execute processing such as display of the image on the user interface 11, registration thereof to the database, and automatic defect classification.

Figure 14:
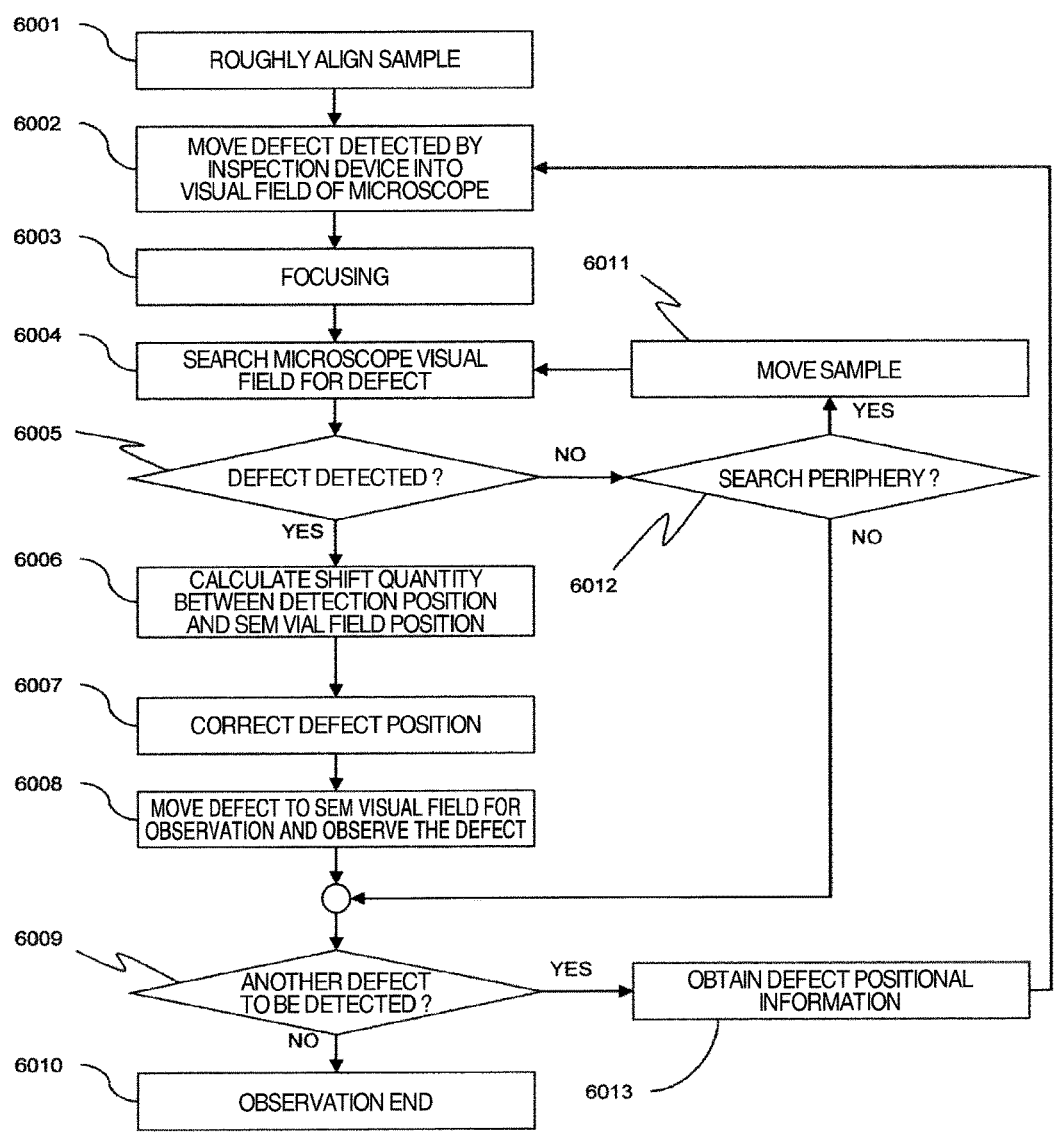
FIG. 14 is a diagram showing a procedure of defect observation in the first embodiment of the present invention.

Description will be given of a flow of the defect observation by referring to FIG. 14.

First, the sample 1 is aligned (6001). This is conducted in the method described for the bright-field observation by the optical microscope 14. Next, by use of positional information of defects beforehand detected by another defect inspection device, the stage 3 is moved such that the defect on the sample 1 to be observed is in the visual filed of the optical microscope 14 (6002). Next, the objective 105 is moved by the height control unit 106 to conduct the focusing (6003).

A search is made for a defect in the image obtained by the optical microscope 14 and the solid-state imaging element 111 (6004); if a defect is detected (6005—yes), based on the difference between the defect detection position by the optical microscope 14 and the positional information of defects beforehand detected by another defect inspection device, the shift quantity of the visual field of the SEM 5 for the defect in the observation of the defect by the SEM is calculated by using the positional information of the defects beforehand detected by another defect inspection device (6006). Based on the calculated shift quantity, the positional information of defects beforehand detected by another defect inspection device is corrected (6007), and the defect for which the positional information is corrected is moved into the visual field of the SEM 5 for the observation thereof (6008). In the operation, the observed information is sent to the control system 10 and is registered to the database 11. Incidentally, if there exist a large number of defects to be observed, several representative defects are extracted therefrom; based on the positional information beforehand detected for the extracted defects by another defect inspection device and the positional information of the respective defects obtained through the detection by the optical microscope 14, there is obtained the shift quantity between the position of the defect beforehand detected by another defect inspection device and the visual position of the SEM 6. By use of the obtained information of the shift quantity, also for defects which are other than the several representative defects and which are not detected by the optical microscope 14, the positional information of defects beforehand detected by another defect inspection device is corrected.

Next, if defect information is not required (6009—no), the end of observation is assumed (60010); if defect information is required (6009—yes), defect positional information of a defect to be observed is obtained, and control returns to the procedure to move the defect to the optical microscope 14 as described above, to execute processing. Incidentally, if no defect is detected in the defect detection procedure described above (6005—no), it is likely that the defect is outside the visual field of the optical microscope 14; hence, a search may be made through the periphery of the visual field of the optical microscope 14. If the search through the periphery is to be conducted (6012—yes), the sample 1 is moved by the distance corresponding to the visual field (6011) to execute the processing beginning at the defect detection procedure described above. Further, if the search through the periphery is not to be conducted (6012—yes), the processing is executed according to the procedure.

There also exists a method in which for each defect, the correction quantity of the defect position is beforehand calculated to be registered to a database such that after the position correction quantity calculation is finished for a plurality of defects or all defects, the observation is conducted by the SEM 5.

Next, the method of calculating the Z position will be described by referring to FIG. 3. FIG. 3 shows a configuration of the Z sensors 4 and 6, and the configuration includes a light source 751, a focusing lens 702, a slit 703, a projection lens 704, a light reception lens 705, and a detector 706. The illumination light source is, for example, a laser oscillator or a lamp, and the detector 706 is, for example, a CCD camera or a CCD linear sensor.

Operation of the Z sensors 4 and 6 will be described. Light emitted from the illumination light source 751 is radiated through the light focusing lens 702 onto the slit 703 and is then focused through the projection lens 704 onto a surface of the sample 1. Light reflected by the sample 1 is gathered via the light reception lens 705 onto the detector 706. In the Z position calculation method, the light detection position of the detector 706 when the sample 1 is at the reference height is first stored. Next, when the height changes, the position of the light detection in the detector 706 changes; hence, by beforehand measuring the relationship between the quantity of movement of the light detection position and the change in the height of the sample 1, it is possible to calculate the height of the sample 1 according to the change in the light detection position.

In conjunction with the present embodiment, description has been given of an example in which the observation is conducted by use of an SEM; however, the present embodiment is applicable to methods and devices which enable more precise observation as compared with the optical observation method, that is, to other electron microscopes including an STEM, fine machining devices employing a focused ion beam, and analysis devices using an X-ray analyzer.

Figure 15:
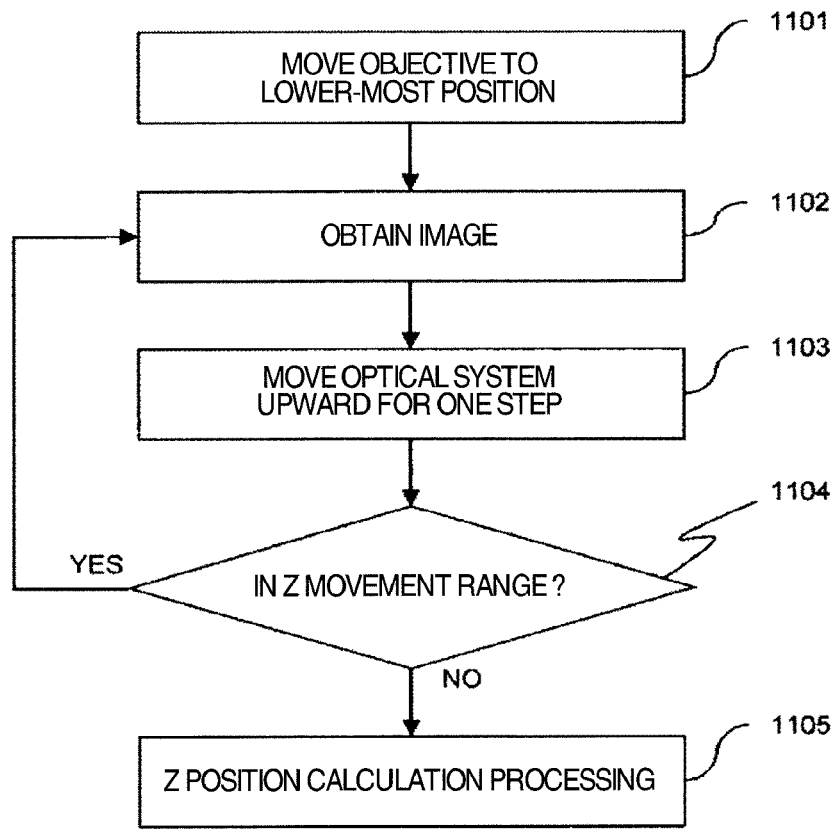
FIG. 15 is a diagram showing a procedure of Z position calculation in third and fourth embodiments of the present invention.
Figure 15:
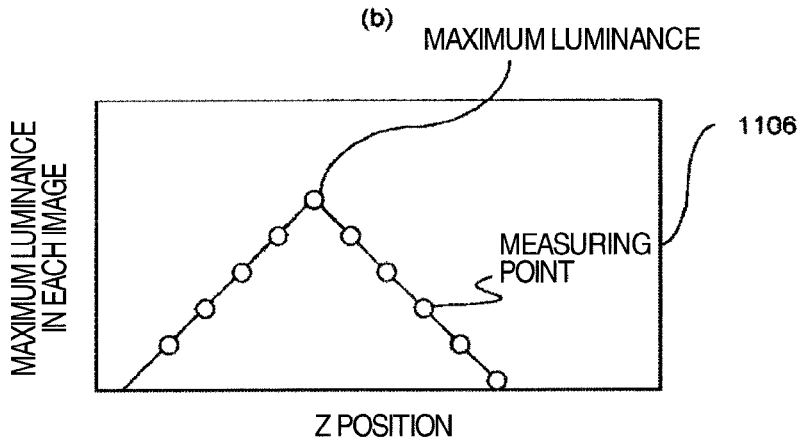

Description will be given of another method of calculating the Z position by referring to FIG. 15. FIG. 15 shows the Z position calculating procedure. This method is a method in which images obtained by an optical microscope are used. First, by use of the Z control unit 105, the objective is moved to the lower-most point (a point where the objective is nearest to the sample; 1101). Next, an image is obtained by the detector 108 to be transmitted to the control system 10 (1102). In this operation, if an edge or a circuit pattern of the sample is in the visual field, it is favorable to use an image obtained through the bright-field observation; if such pattern is not present and the edge is not present, it is favorable to use an image obtained through the dark-field observation. After the image is obtained, the objective 104 is moved upward for one step by the Z control unit 105 (1103). In this connection, the one step is associated with resolution of the Z position detection and is favorably equal to or less than half the depth of focus of the objective 104. After the objective 104 is moved, an image is again obtained. The Z movement and the obtaining of the image are carried out in a range beforehand set; if the range thus set is exceeded, the obtaining of the image is terminated (1104) and control goes to the Z position calculation (1105).

Description will be given of an example of the Z position calculation processing. First, a search is made for the maximum luminance point of each obtained image, and the luminance and the Z position at which the maximum luminance point is obtained are used to plot a graph (1106). Next, the maximum luminance in the graph 1106 is calculated. In the operation, it is desirable that the respective measuring points are approximated to a curved line to calculate the maximum luminance point. The Z point of the calculated maximum luminance point is the position for the best focus of the objective 105.

If the Z position calculation described above is employed, the Z sensor 7 may be dispensed with; hence, the configuration is simplified.

By referring to FIG. 16, description will be given of a second configuration example of the optical microscope 14 in the present embodiment. The optical microscope 14 includes a dark-field lighting unit 101, a light introduction mirror 102, a mirror 104, an objective 105, a height control unit 106, an imaging optical system 110, a solid-state imaging element 111, an objective rotation unit 117, and a liquid-crystal controller 118. The imaging optical system 110 includes only an imaging lens 116, and a distribution polarization element 114 is fixed onto a pupil plane 112a of the objective 105 in the configuration.

In this case, the lens system to move the pupil plane 112a of the objective 105 to the outside of the objective, the half-silvered mirror 108, and the bright-field lighting unit 109 are dispensed with, leading to an advantage of a simple configuration.

In this situation, to adjust the angle of the distribution polarization element 114, there may be disposed a unit 117 which rotates the objective 105 about the central axis of the objective 105. In the configuration, the rotation unit 117 is coupled with the control system 10.

Figure 17:
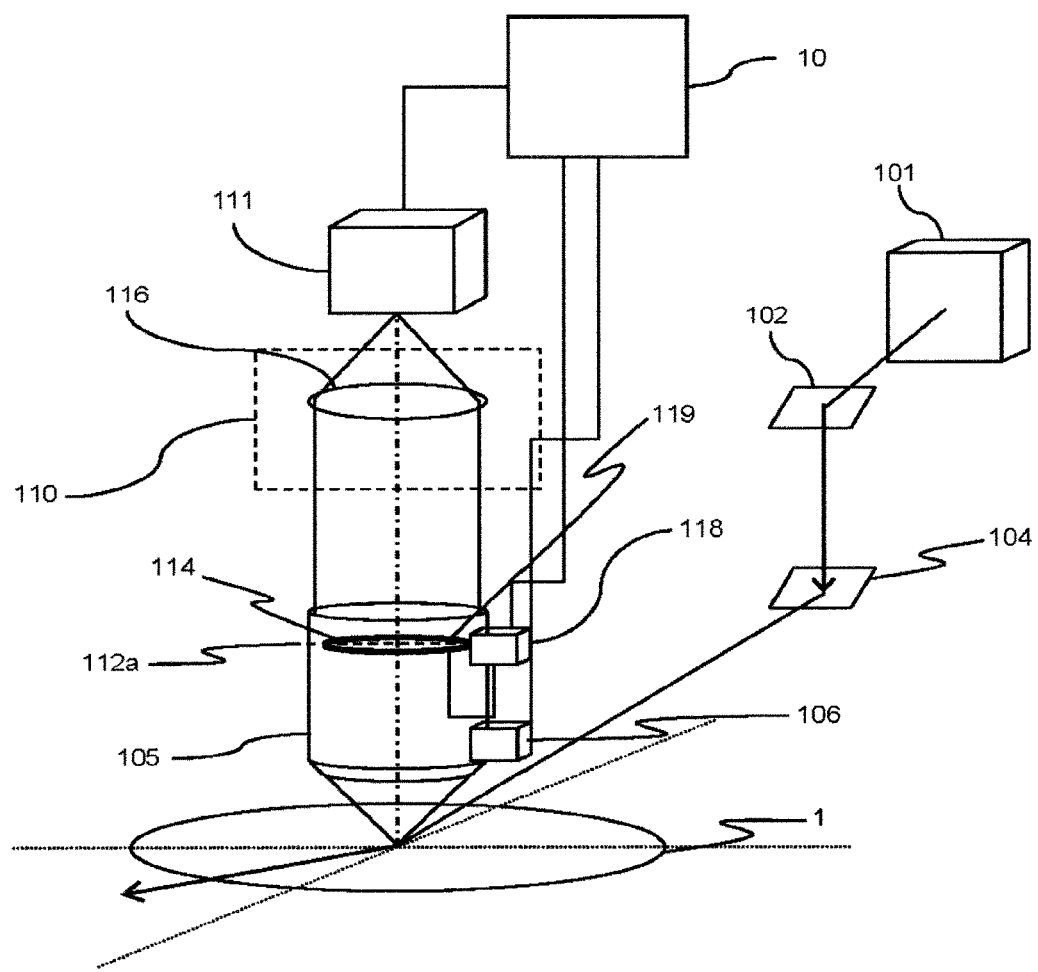
FIG. 17 is a diagram showing in detail a third configuration example of the optical microscope in the first embodiment of the present invention.

By referring to FIG. 17, description will be given of a third configuration example of the optical microscope 14 in the present embodiment. The optical microscope 14 includes a dark-field lighting unit 101, a light introduction mirror 102, a mirror 104, an objective 105, a height control unit 106, an imaging optical system 110, a solid-state imaging element 111, a liquid-crystal controller 118, and a polarization plate 119. The imaging optical system 110 includes an imaging lens 116, and as the distribution polarization element 114, a liquid-crystal element is fixed onto a pupil plane 112a of the objective 105 in the configuration. In this configuration, as shown in FIG. 17, the transmission polarization axis of the distribution polarization element is controllable by a combination of the liquid-crystal controller 118 and a polarization plate 119 which are disposed outside the objective; this leads to an advantage that by setting the polarization characteristic of the liquid crystal to non-polarization, the bright-field observation is enabled, and by providing the polarization characteristic, highly-sensitive dark-filed observation is possible. The liquid-crystal controller 118 is coupled with the controller 10. In this configuration, the objective rotation unit 117 may be advantageously dispensed with. In the configuration, a half-silvered mirror 108 and a bright-field lighting unit 109 are employed to conduct the bright-field observation.

Second Embodiment

Figure 18:
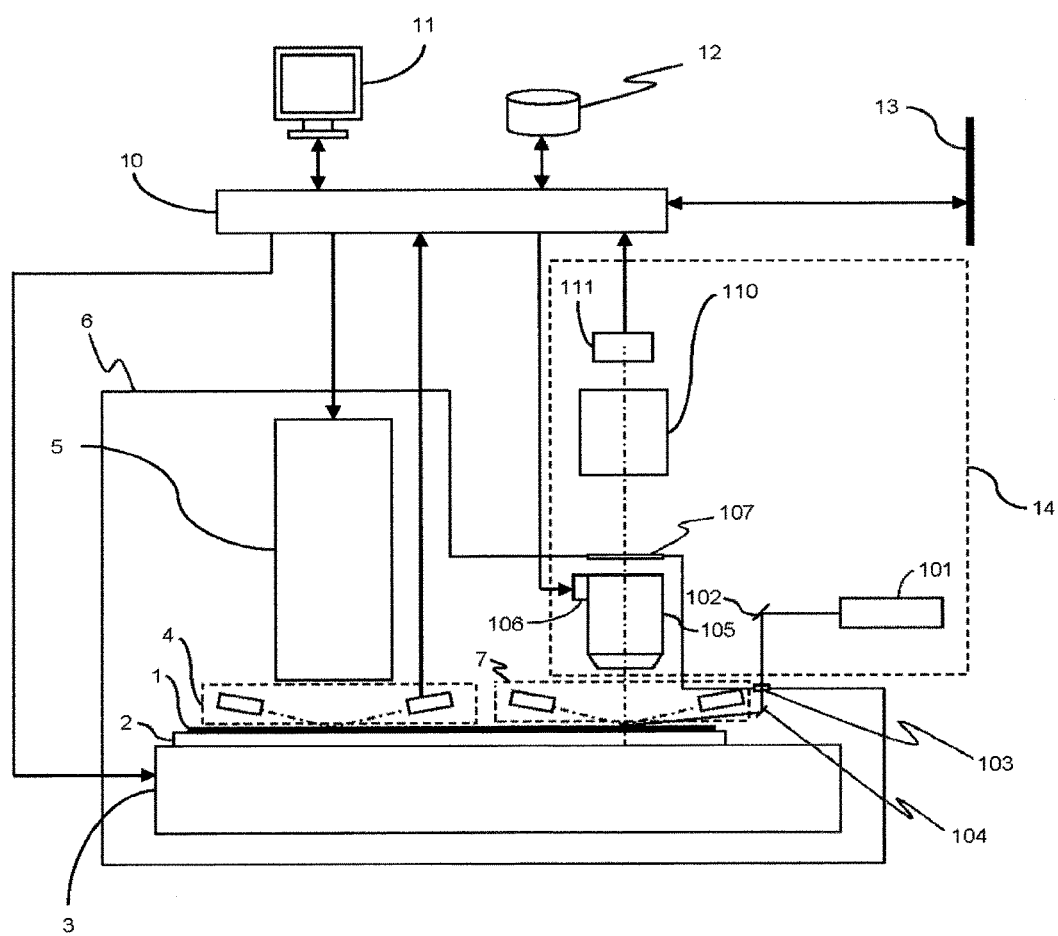
FIG. 18 is a diagram showing an example of a configuration of a defect observation device in a second embodiment of the present invention.

Next, description will be given of a second embodiment of the defect inspection device according to the present invention by referring to FIG. 18. The second embodiment differs from the first embodiment in that the half-silvered mirror 108 and the bright-field lighting unit 109 are not arranged. Hence, the configuration is advantageously simplified as shown in FIG. 18. In the configuration shown in FIG. 18, the components assigned with the same reference numerals as those of the configuration of FIG. 1 have functions similar to those described by referring to FIG. 1.

In this situation, the focusing of the optical microscope 14 is carried out by use of the Z sensor 7 or through image processing based on dark-field images obtained by the optical microscope 14 as described above.

Figure 16:
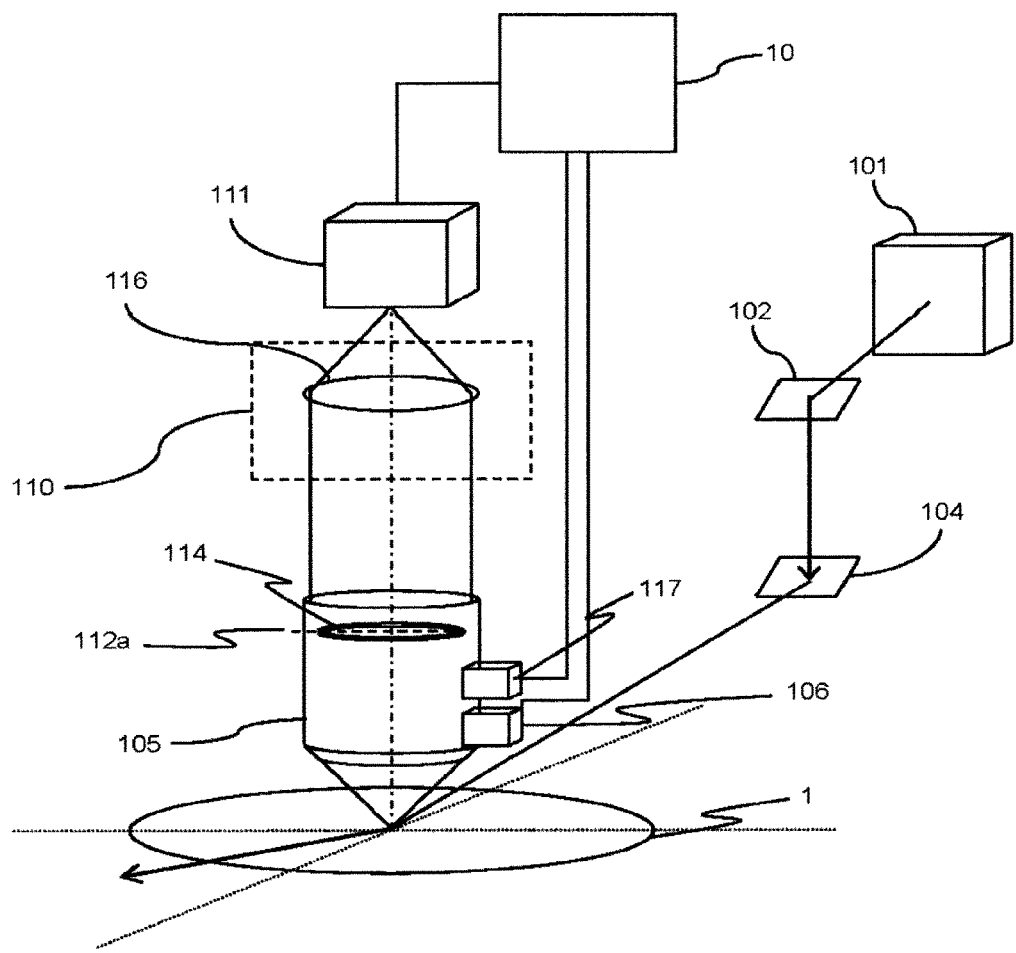
FIG. 16 is a diagram showing in detail a second configuration example of the optical microscope in the first embodiment of the present invention.

In this case, as in the optical microscope 14 shown in FIG. 16, the distribution polarization element 114 may be fixed onto the pupil plane 112a of the objective 105 in the configuration.

Third Embodiment

Figure 19:
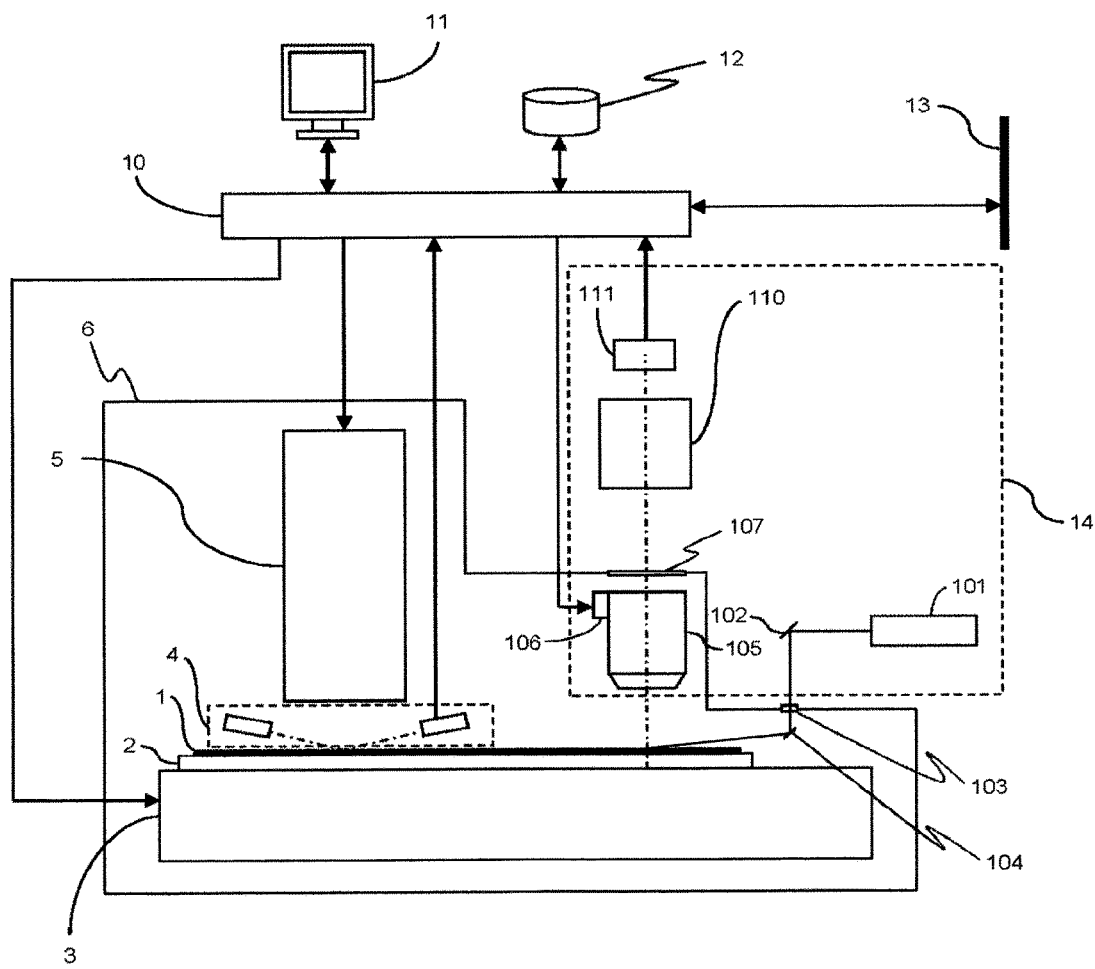
FIG. 19 is a diagram showing an example of a configuration of a defect observation device in a third embodiment of the present invention.

Next, description will be given of a third embodiment of the defect inspection device according to the present invention by referring to FIG. 19. The third embodiment differs from the first embodiment in that the Z sensor 7, the half-silvered mirror 108, and the bright-field lighting unit 109 are not arranged for the optical microscope 14. Hence, advantageously, the configuration is simplified as shown in FIG. 19 and there is secured a space in which an objective having a larger numeral aperture is installed as the objective 105. In the configuration shown in FIG. 19, the components assigned with the same reference numerals as those of the configuration of FIG. 1 have functions similar to those described by referring to FIG. 1.

In this configuration, the focusing of the optical microscope 14 is carried out by use of the Z sensor 7 or through image processing based on dark-field images obtained by the optical microscope 14 as described above.

In this occasion, as in the optical microscope 14 shown in FIG. 16, the distribution polarization element 114 may be fixed onto the pupil plane 112a of the objective 105 in the configuration.

Fourth Embodiment

Figure 20:
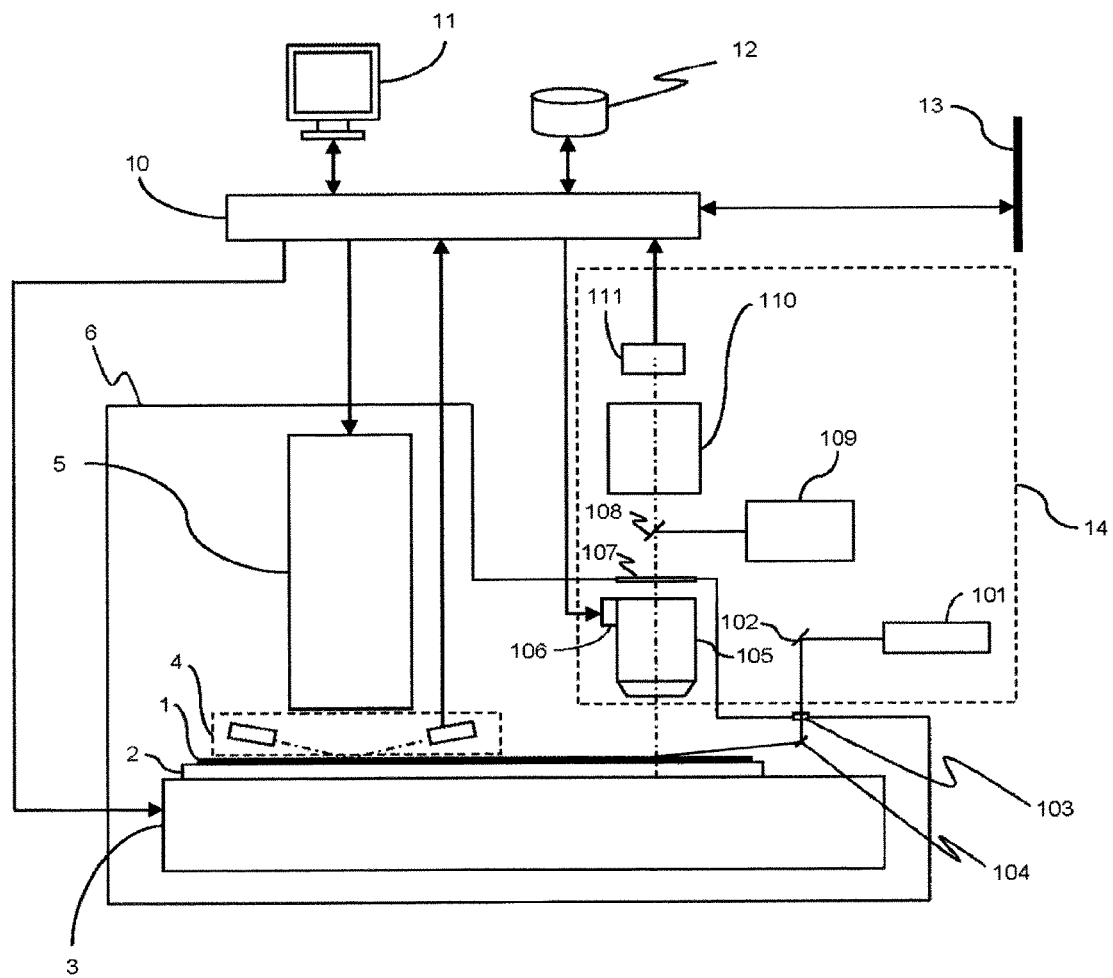
FIG. 20 is a diagram showing an example of a configuration of a defect observation device in a fourth embodiment of the present invention.

Next, description will be given of a fourth embodiment of the defect inspection device according to the present invention by referring to FIG. 20. The fourth embodiment differs from the first embodiment in that the Z sensor 7 is not arranged for the optical microscope 14. Hence, advantageously, the configuration is simplified as shown in FIG. 20, and there is secured a space in which an objective having a larger numeral aperture is installed as the objective 105. In the configuration shown in FIG. 20, the components assigned with the same reference numerals as those of the configuration of FIG. 1 have functions similar to those described by referring to FIG. 1.

In this case, the focusing of the optical microscope 14 is carried out through image processing based on bright-field images or dark-field images obtained by the optical microscope 14 as described above.

In the configuration, as in the optical microscope 14 shown in FIG. 16, the distribution polarization element 114 may be fixed onto the pupil plane 112a of the objective 105 in the configuration.

Next, by referring to FIGS. 21 to 35, description will be give of various distribution filters 2222 which can be installed in place of the filter unit 114 used in the respective embodiments above.

Here, as for components of various distribution filters 2222 described below; the arrangement of the phase shifter 391, the inclinations of the slow axis and the fast axis of the wave plates 331 and 332, the optical rotatory direction by the polarization direction controller 665, and the transmission polarization axis directions of the light block zone and the polarization element in the spatial filter are determined based on the scattered light intensity distribution obtained through the scattered light simulation or through the actual measurement beforehand described by referring to FIG. 9.

Next, description will be given of a method of determining the arrangement of the phase shifter, the inclinations 338 and 339 of the slow axis and the fast axis of the wave plates, and the optical rotatory direction 780 by the polarization direction controller.

Figure 21:
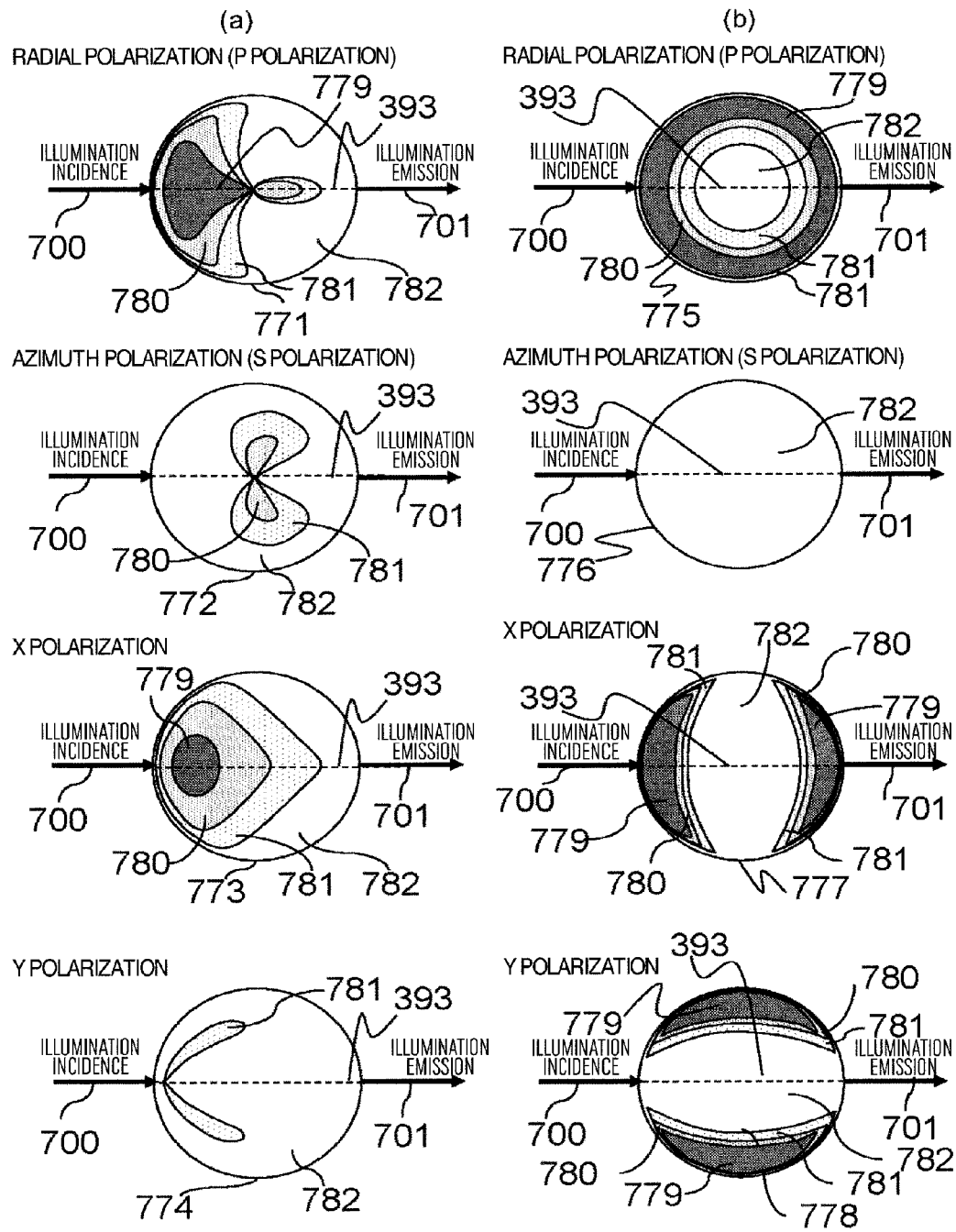
FIG. 21 is a diagram showing an example of intensity distribution for each polarization of the scattered light intensity from the substrate surface and intensity distribution for each polarization of the scattered light intensity from foreign matter obtained by use of scattered light simulation.

In FIG. 21, (a) and (b) show calculation results of scattered light simulation, including the scattered light intensity distribution fN(r,θ) of the scattered light from concavity and convexity on the substrate surface, the distribution pNp(r,θ) of the radial polarization (p-polarized light) component of the scattered light, the distribution pNs(r,θ) of the azimuth polarization (s-polarized light) component thereof, the distribution pNx(r,θ) of the x polarized light thereof, and the distribution pNy(r,θ) of the y polarized light thereof as well as the scattered light intensity distribution fs(r,θ) of the scattered light from defects or foreign matter, the distribution psp(r,θ) of the radial polarization (p-polarized light) component of the scattered light, the distribution pss(r,θ) of the azimuth polarization (s-polarized light) component thereof, the distribution psx(r,θ) of the x-polarized light thereof, and the distribution psy(r,θ) of the y-polarized light thereof. These distributions are obtained through an operation in which by the scattered light simulation, there are obtained Stokes vectors of the scattered light from fine concavity and convexity on the substrate surface and Stokes vectors of the scattered light from foreign matter to be detected with high sensitivity and then the distributions are obtained by use of the Stokes vectors thus obtained. Incidentally, the polarization to be obtained is not limited to these polarization, but there may be employed linearly polarized light in which the angle of polarization is inclined in a range from Π to −Π or elliptically (circularly) polarized light.

FIG. 21(a) shows the intensity distribution 771 of the radial polarization, the intensity distribution 772 of the azimuth polarization, the intensity distribution 773 of the x polarization, and the intensity distribution 774 of the y polarization of the scattered light (light wavelength 405 nm) from fine concavity and convexity on the substrate surface. Further, FIG. 21(b) shows the intensity distribution 775 of the radial polarization, the intensity distribution 776 of the azimuth polarization, the intensity distribution 777 of the x polarization, and the intensity distribution 778 of the y polarization of the scattered light due to spherical foreign matter having a diameter of 18 nm. Incidentally, the axis 393 indicates an axis on the pupil plane 112 corresponding to the illumination incidence axis.

In each distribution of FIG. 21, a region 779 is a region with high scattered light intensity, a region 780 is a region with slightly high scattered light intensity, a region 781 is a region with slightly low scattered light intensity, and a region 782 is a region with low scattered light intensity; however, these areas indicate a relative relationship with respect to intensity in the distributions, that is, even the same regions in the respective distributions do not necessarily indicate the same intensity (for example, the intensity distribution region 779 of the radial polarization and the intensity distribution region 779 of the x polarization do not necessarily indicate the same intensity).

According to the scattered light intensity distribution of each polarization shown in FIG. 21(a), it is recognizable that the scattered light from fine concavity and convexity on the substrate surface is strong on the illumination incidence 700 side (back scattering), and the radial polarization is strong in the polarization of the back scattering. Also, according to the scattered light intensity distribution of each polarization shown in FIG. 21(b), it is recognizable that the scattered light from fine foreign matter is substantially isotropic, and the radial polarization is strong. Hence, based on these results, by setting and by installing the polarization filter according to necessity, it is possible to increase the ratio of the scattered light from the substrate surface to that from the foreign matter, to thereby enable the high S/N defect detection.

Figure 22:
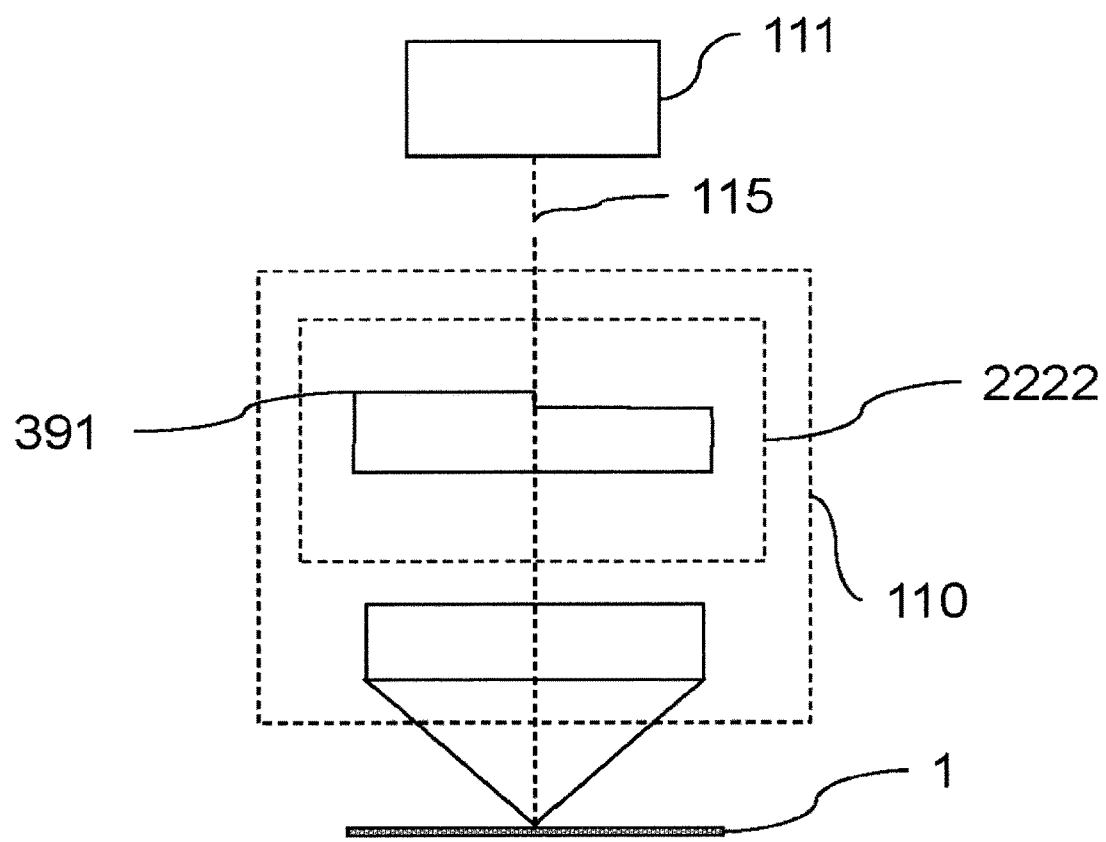
FIG. 22 is a diagram showing an example in which a phase shifter is employed in the vicinity of the optical microscope pupil plane 112 in the first embodiment of the present invention.

FIG. 22 is a diagram showing an example for radial polarization when a phase shifter 391 is employed in the proximity of the pupil plane 112 of the optical microscope. Here, as for the polarization direction of the scattered light from the foreign matter, since the vibration direction and the intensity are substantially equal with respect to the axis 393 on the pupil plane 112 corresponding to the illumination incidence axis, part of light cancels with each other through interference of light having vibration directions symmetric with respect to the axis 393 on the pupil plane 112 corresponding to the illumination incidence axis; by using the phase shifter on the pupil plane 112 and in the vicinity of the pupil plane 112, it is possible to mutually strengthen the intensity of the scattered light from the foreign matter. In addition, the phase shifter may be used to suppress the intensity of the scattered light from the substrate surface or to mutually strengthen the intensity of the scattered light from the foreign matter while suppressing the intensity of the scattered light from the substrate surface.

Figure 23:
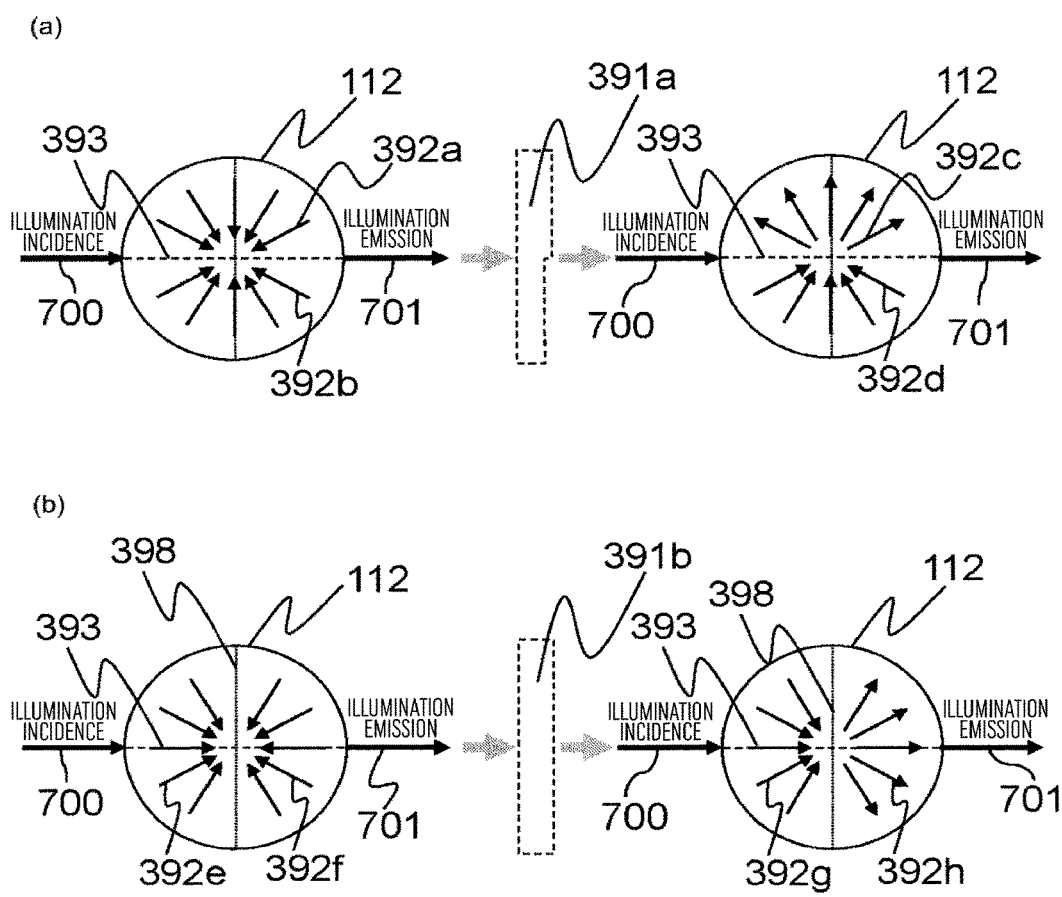
FIG. 23 is a diagram to explain a change in the radial polarization when a phase shifter is employed in the vicinity of the pupil plane 112.

Here, by referring to FIG. 23, description will be more concretely given of the advantage of the phase shifter according to an example of light of radial polarization.

According to the result of the scattered light simulation, the scattered light from the fine foreign matter is similar to the light of radial polarization as shown in the radial polarization light distribution 775 of FIG. 21(a); the vibration directions oppose to each other in the directions symmetric with respect to the optical axis; hence, the intensity is lowered due to superimposition. To suppress the lowering of intensity, the phase shifter is employed for the radial polarization.

FIG. 23(a) shows an application example of radial polarization wherein a phase shifter 391a, which produces a phase difference of Π by using, as a boundary, a plane perpendicular to the substrate including the axis 393 on the pupil plane 112 corresponding to the illumination incidence axis or a plane on the pupil 112 corresponding thereto, is arranged in the proximity of the pupil plane 112 of the optical microscope. FIG. 23(b) shows an application example of radial polarization wherein a phase shifter 391b, which produces a phase difference of Π in areas over and under a boundary in FIG. 23, the boundary being the axis 393 on the pupil plane 112 corresponding to the illumination incidence axis, is arranged in the proximity of the pupil plane 112 of the optical microscope. In FIG. 23(a), it can be considered that the y-directional components of radial light 392a and radial light 392b cancel each other; hence, when the radial light 392a interferes with the radial light 392b, the peak of the y-directional scattered light intensity is lowered. For the scattered light of the radial polarization, when a phase shifter to produce a phase difference of Π in areas over and under a boundary in FIG. 23, which is the axis 393 on the pupil plane 112 corresponding to the illumination incidence axis, is arranged in the proximity of the pupil plane 112 of the optical microscope; there appear states 392c and 392d in which the y-directional components of 392c and 392d strengthen each other; hence, it is possible to heighten the peak.

In FIG. 23(b), it can be considered that the x-directional components of radial polarization light 392e and radial polarization light 392f cancel each other; hence, when the radial light 392e interferes with the radial light 392f, the peak of the x-directional scattered light intensity is lowered. In this situation, when a phase shifter to produce a phase difference of Π in areas on the left and right sides with respect to a boundary in FIG. 23, which is an axis 398 perpendicular to the axis 393 on the pupil plane 112 corresponding to the illumination incidence axis, is arranged in the proximity of the pupil plane 112 of the optical microscope; there appear states 392g and 392h in which the x-directional components of 392g and 392h strengthen each other; hence, when they interfere with each other, it is possible to heighten the peak.

Next, description will be given of an example of the distribution polarization element having an advantage to suppress the scattered light from the substrate surface. As shown in FIG. 21, the scattered light from foreign matter varies in the polarization direction from the scattered light from the substrate surface. By using the polarization difference and by installing, on the pupil plane 112 or in the vicinity thereof, a distribution polarization element with zones for each of which the transmission polarization direction is appropriately selected, by use of the scattered light simulation or the actually measured values, to suppress the scattered light from the substrate surface and to minimize the reduction in the scattered light from foreign matter, it is possible to increase the ratio of the scattered light from the substrate surface to that from the foreign matter, and it is hence possible to conduct the high S/N defect detection.

Figure 24:
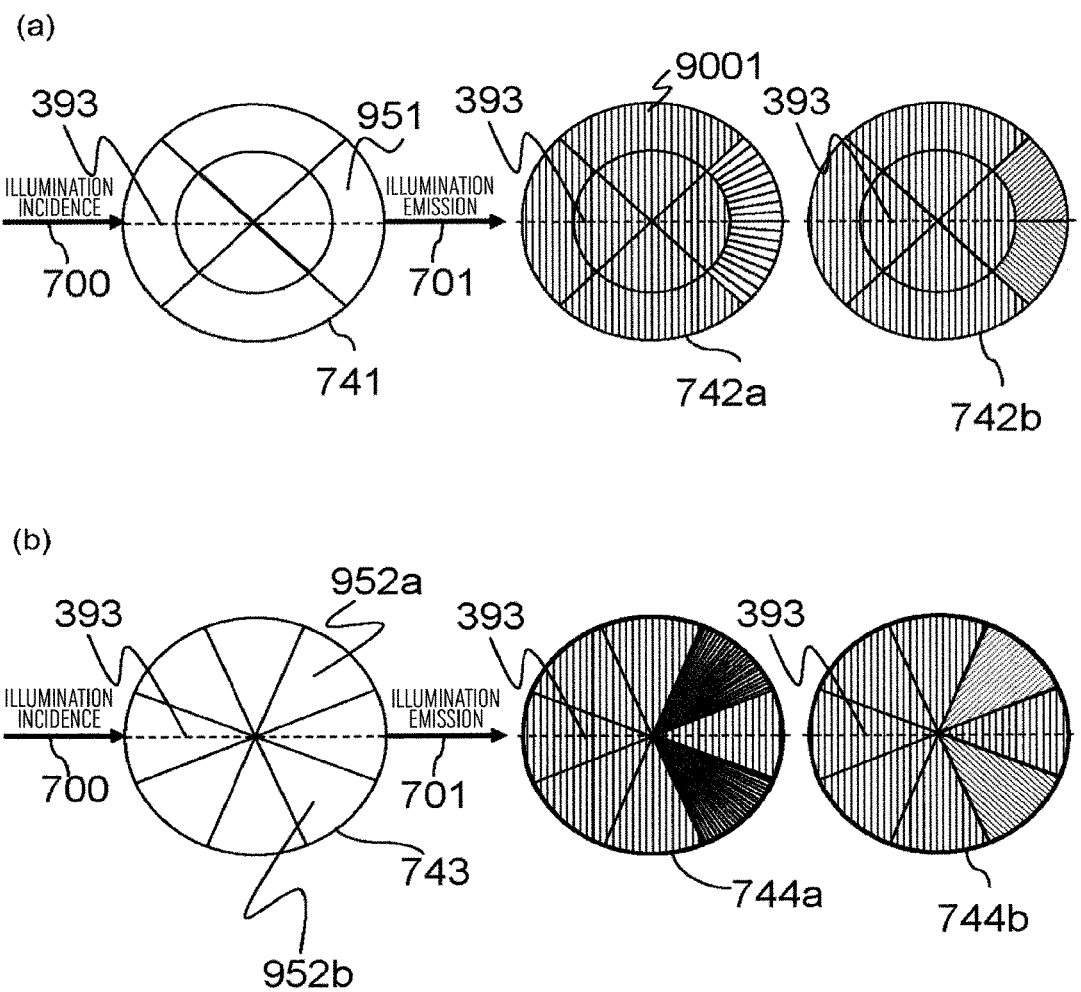
FIG. 24 is a diagram showing an example of division of the pupil plane 112 and an example of a distribution polarization element in which the pupil plane 112 is divided into eight regions and the ratio between the foreign matter scattered light and the substrate surface scattered light is obtained for each region by scattered light simulation to select a polarization direction for which the ratio between the foreign matter scattered light and the substrate surface scattered light is large.

As a concrete example, FIG. 24 shows distribution polarization elements 742a, 742b, 744a, and 744b for which the transmission polarization direction 9001 (slashes in FIG. 24) is selected, by dividing the space on the pupil plane 112 or in the vicinity thereof and by using the results of the scattered light simulation shown in FIG. 21, for each divided area, to thereby suppress the scattered light from the substrate surface and to minimize the reduction in the scattered light from foreign matter. In this regard, the polarization directions used in the discussion here include directions of the radial polarization, the azimuth polarization, the x polarization, and the y polarization; however, the present embodiment is not restricted by these directions.

FIG. 24(a) shows examples of distribution polarization elements 742a and 742b for which the transmission polarization direction 9001 is selected, by dividing the space 741 on the pupil 112 or in the vicinity thereof into two partitions in the radial direction and in four partitions in the circumferential direction, to increase, based on the results of the scattered light simulation shown in FIG. 21, the ratio of the scattered light from the substrate surface to that from the fine foreign matter. For the distribution polarization element 742a, the transmission polarization direction 9001 is selected such that the radial polarization light transmits in a zone 951 on the outer circumferential side of the illumination emission side and they polarization light transmits in the remaining zone; for the distribution polarization element 742b, the transmission polarization direction 9001 is selected such that the linear polarization light inclined ±Π/4 transmits in a zone 951 on the outer circumferential side of the illumination emission side and the y polarization light transmits in the remaining zone.

Further, FIG. 24(b) shows examples of distribution polarization elements 744a and 744b for which the transmission polarization direction 9001 is selected by dividing the space 743 on the pupil 112 or in the vicinity thereof into eight partitions in the circumferential direction, to increase, based on the results of the scattered light simulation shown in FIG. 21, the ratio of the scattered light from the substrate surface to that from the fine foreign matter. For the distribution polarization element 744a, the transmission polarization direction 9001 is selected such that the radial polarization light transmits in divided zones 952a and 952b and the y polarization light transmits in the remaining zone; for the distribution polarization element 744b, the transmission polarization direction 9001 is selected such that the linear polarization light inclined ±Π/4 transmits in divided zones 952a and 952b and the y polarization light transmits in the remaining zone.

In each of the distribution polarization elements 742a, 742b, 744a and 744b described above, the scattered light is suppressed, based on the scattered light simulation results, in the zones in which the scattered light from the substrate surface is strong; hence, it is possible to conduct the high S/N defect detection. Incidentally, the distribution polarization elements of FIG. 24 and FIG. 7 described above may be used in combination with the phase shifter 391. By using the phase shifter, it is possible to suppress, at occurrence of interference among the scattered light having passed the distribution polarization element, the reduction in the intensity taking place due to the superimposition. Moreover, although description has been given of examples of division into four and eight partitions, the present embodiment is not restricted by the division; it is only required that the area is appropriately divided, according to the scattered light distribution, into an appropriate number of partitions to use an optimal distribution polarization element for each partition; also, in addition to the division in the circumferential direction, the area may be appropriately divided in the longitudinal direction, in the vertical direction, in the lattice form, and the like. Further, the present embodiment is not restricted by the use of two kinds of distribution polarization elements; three or more kinds thereof may be used in the configuration.

Next, description will be given of a wave plate which controls the polarization direction of scattered light from the substrate surface and that of scattered light from foreign matter to thereby suppress the scattered light from the substrate surface and to suppress the reduction in the intensity of the scattered light from foreign matter. By using the wave plate, it is possible to control the polarization direction of the scattered light to align the polarization direction, which makes it also possible to simplify the distribution polarization element.

Figure 25:
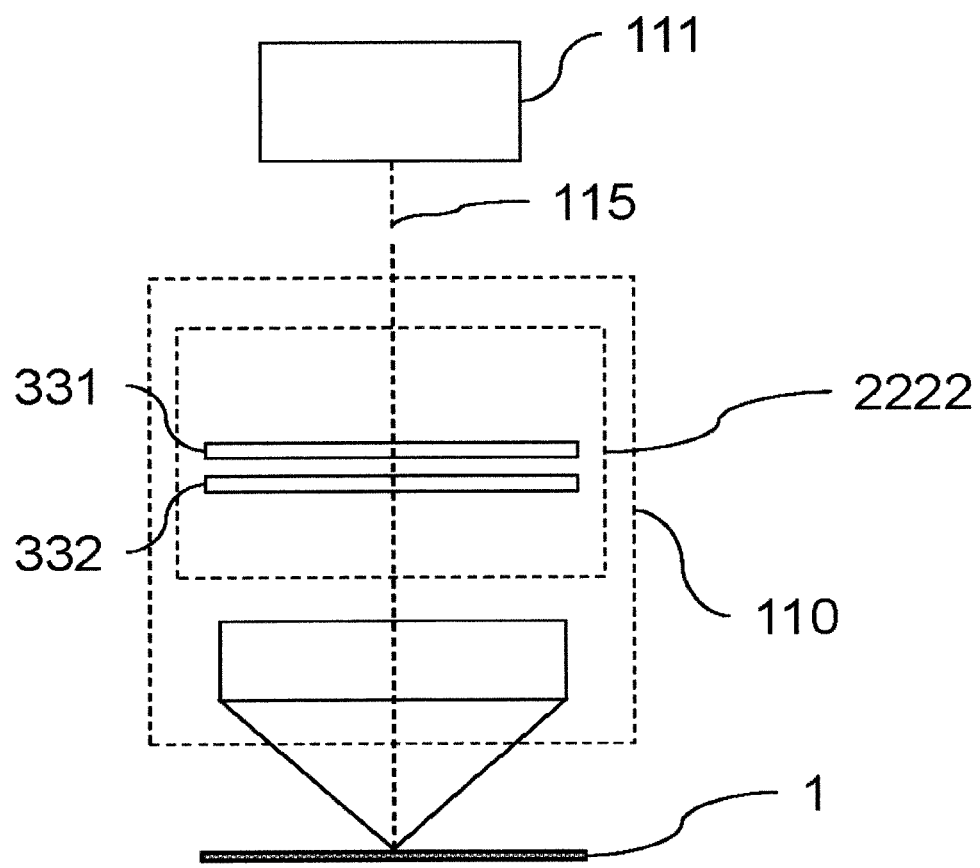
FIG. 25 is a diagram showing an example in which a wave plate is employed in the vicinity of the optical microscope pupil plane 112 in the first embodiment of the present invention.

FIG. 25 shows an example of the use of the wave plate in which a distribution 1/2 wave plate 331 and a distribution 1/4 wave plate 332 are employed in the vicinity of the pupil plane 112 of the optical microscope. Here, as for the distribution 1/2 wave plate 331 and the distribution 1/4 wave plate 332, the present embodiment is not restricted by the combination thereof, that is, either one may be employed or the arrangement thereof may be changed according to necessity. Further, it is also possible to use a combination of these wave plates and the phase shifter 391.

Next, description will be given, in association with an example of radial polarization, of an advantage when a distribution polarization element is employed.

Figure 26:
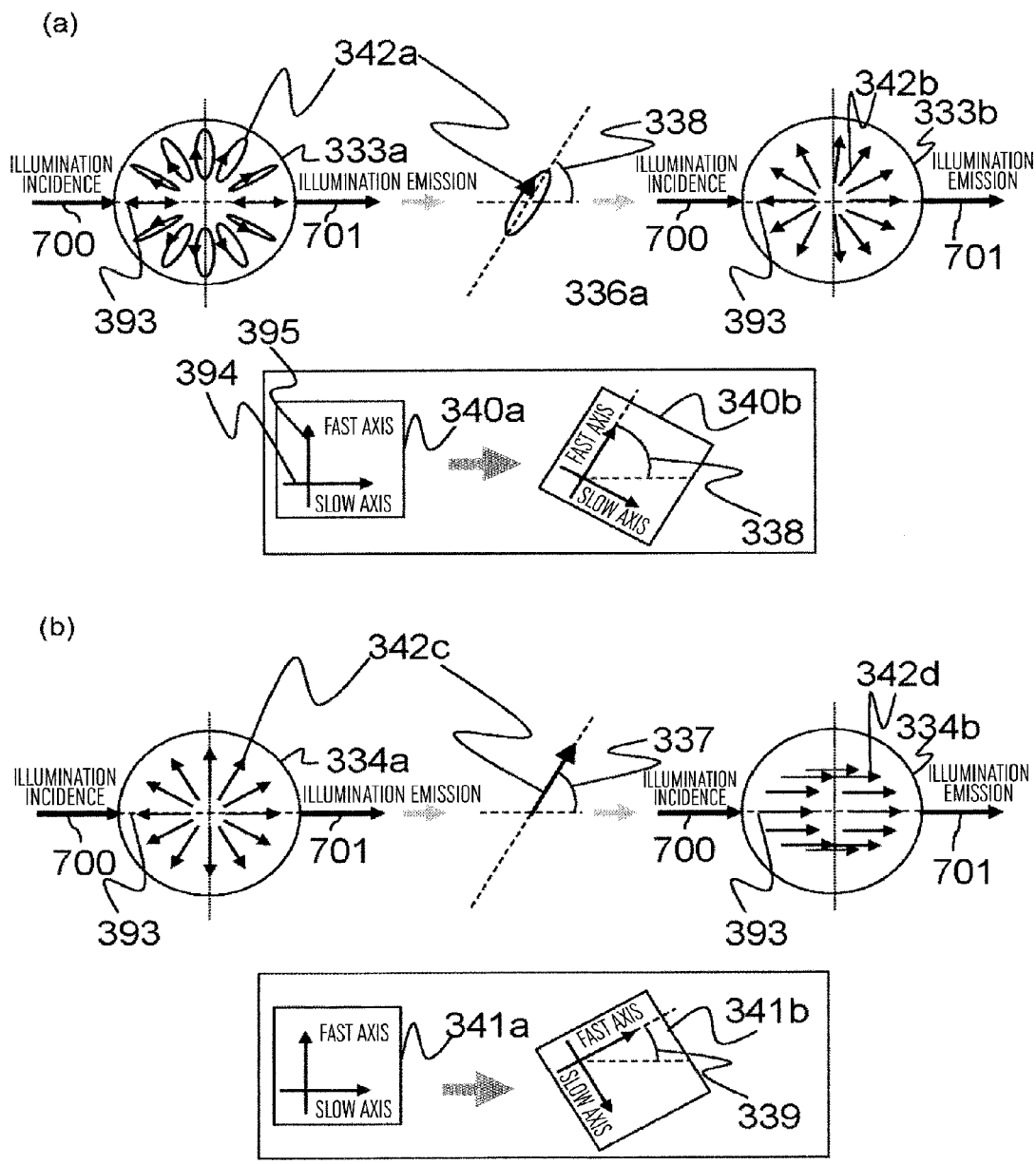
FIG. 26 is a diagram to explain a change in the polarization when a wave plate is employed in the vicinity of the pupil plane 112.

FIG. 26 is a diagram to explain a change in the polarization when a wave plate is employed in the vicinity of the pupil plane 112. By controlling electric field vectors by the wave plate, it is possible to suppress the scattered light from the substrate and to strengthen the scattered light from foreign matter to be detected, to thereby increase the ratio of the scattered light from foreign matter to the scattered light from the substrate surface.

As a concrete example, FIG. 26(a) shows an example of application of the 1/4 wave plate 332 to elliptic polarization of the polarized light 333a on an arbitrary pupil plane 112. Elliptic polarization light 342a can be changed to linear polarization light 342b by arranging a 1/4 wave plate 340a in which in order that its fast axis 395 matches the major axis of elliptic polarization light 342a inclined by an angle 338 relative to the x axis and its slow axis 394 matches the minor of the elliptic polarization light 342a, the 1/4 wave plate is arranged 335a to be inclined by an angle 338. By selectively transmitting, by use of the distribution polarization element, the linear polarization light obtained by converting the elliptic polarization light, it is possible to suppress the reduction in the quantity of the scattered light from foreign matter due to the distribution polarization element.

FIG. 26(b) shows an example of application of the 2/1 wave plate 331 to radial polarization light 334a on the pupil plane 112. Scattered light 775 from the fine foreign matter is similar to the radial polarization light; hence, in the directions symmetric with respect to the axis 393 on the pupil plane 112 corresponding to the illumination incidence axis, it is likely that the vibration directions of electric field vectors oppose each other and the intensity is reduced by the superimposition. FIG. 26(b) is an example in which a 1/2 wave plate 332 is employed to suppress the reduction in the intensity; for an electric field vector 342c inclined by an angle 337 relative to the axis 393 on the pupil plane 112 corresponding to the illumination incidence axis, by arranging the 1/2 wave plate 332 in the state 341a as a 1/2 wave plate 341b in which the fast axis thereof is inclined by an angle of 339, which is half the angle 337, relative to the x axis; the electric field vector 342c can be changed to an electric field vector 342d parallel to the axis 393 on the pupil plane 112 corresponding to the illumination incidence axis. In this way, by arranging the distribution wave plate 332a on the pupil plane 112 or in the vicinity thereof, the vibration directions of the electric field vectors become parallel to each other in the directions symmetric with respect to the axis 393 on the pupil plane 112 corresponding to the illumination incidence axis; hence, it is possible to strengthen the peak intensity of the scattered light through the superimposition.

Figure 27:
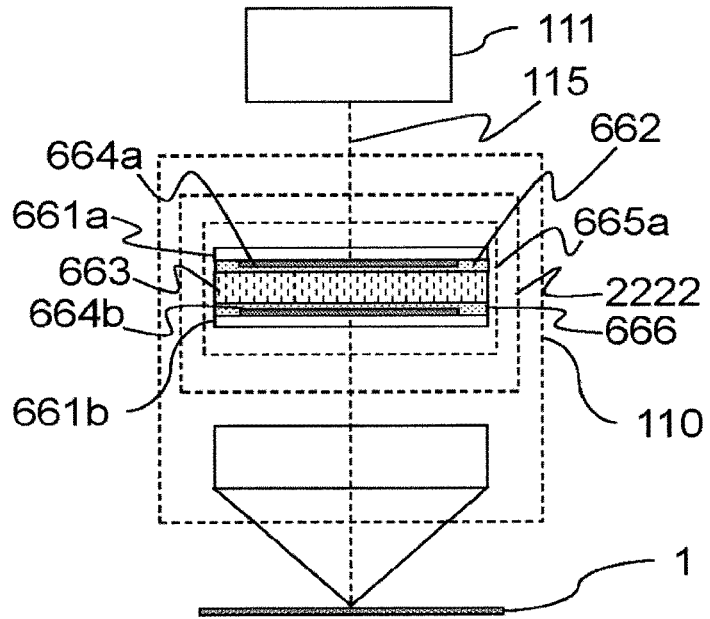
FIG. 27 is a diagram showing an example in which a polarization direction controller using liquid crystal is employed in the vicinity of the optical microscope pupil plane 112 in the first embodiment of the present invention.
Figure 27:
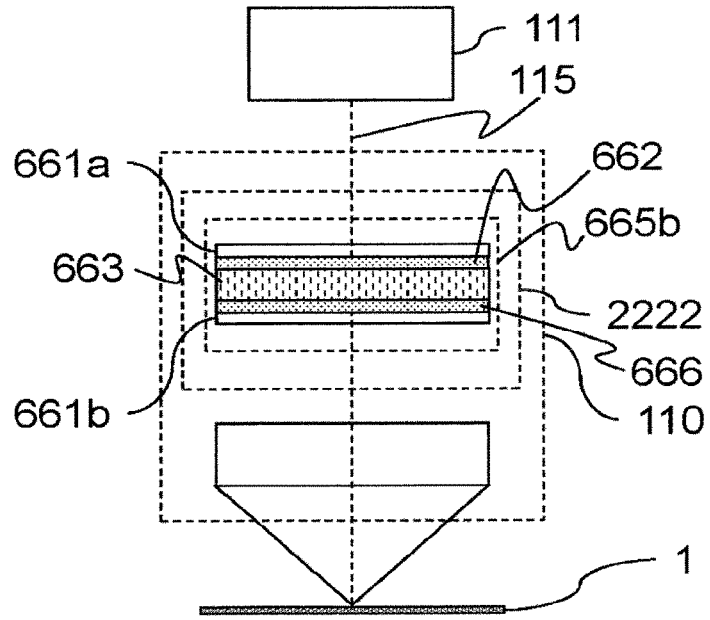

Next, description will be given of an example of arrangement of the polarization direction controller 665 in which liquid crystal is used in place of the 1/2 wave plate 331 and the 1/4 wave plate 332 of FIG. 25 by referring to FIGS. 27 and 28. When liquid crystal is used, it is possible, by controlling the voltage to be applied thereto and by controlling the direction of rubbing on the alignment film, to precisely control the polarization direction, which is not possible by the 1/2 wave plate 331 and the 1/4 wave plate 332 using crystal of quartz.

Figure 28:
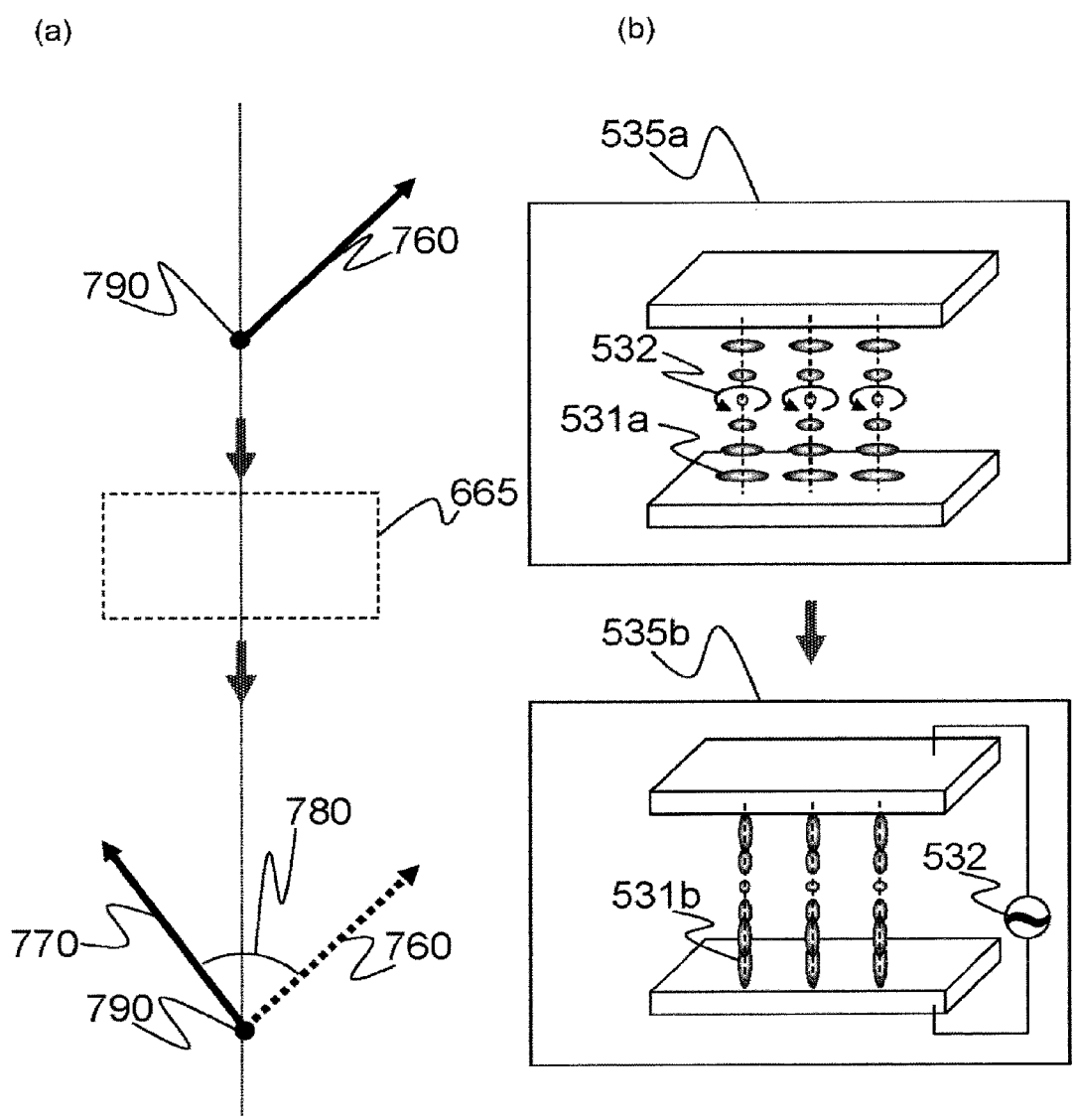
FIG. 28 is a diagram to explain a change in the polarization direction by the polarization direction controller.

FIG. 28 is a diagram to explain a change in electric field vectors according to polarization direction control; an electric field vector 760 at an arbitrary point 790 and at an arbitrary point of time is changed to an electric field vector 770 by using the polarization direction controller 665. Here, it is assumed that the angular difference 780 between the electric field vector 760 and the electric field vector 770 is an optical rotatory angle 780.

FIG. 27(a) shows an example of the optical microscope including a polarization direction controller 665a configured by appropriately using liquid crystal 663 intercalated between outer-most layers 661a and 661b, alignment films 662 and 666, and electrodes 664a and 664b in which alignment of molecules of the liquid crystal 663 is controlled by applying a voltage between the electrodes 664a and 664b, to thereby control the polarization direction.

Here, the liquid crystal is crystal which is in a state between liquid and crystal and which has both of fluidity of liquid and anisotropy of crystal; the liquid crystal includes liquid crystal with optical rotatory power, i.e., having chirality and liquid crystal without optical rotatory power, i.e., not having chirality.

In the liquid crystal having chirality, as exemplified in FIG. 28(b), liquid-crystal molecules 531a in contact with the substrate rotates and aligns in the perpendicular direction as indicated by 532. The direction of rotation is determined by the chirality of the liquid crystal. By transmitting light through the liquid crystal 535a, the polarization direction of the light rotates according to the alignment 532 of molecules of the liquid crystal, and it is hence possible to change the polarization state.

When a voltage is applied to the liquid crystal having chirality, the horizontally arranged molecules of the liquid crystal are perpendicularly arranged as indicated by 531b; and as molecules of the liquid crystal are further perpendicularly arranged, the optical rotatory power is lost, that is, liquid crystal 535b has no optical rotatory power. The polarization direction can be changed by controlling the angle of the perpendicular arrangement of the molecules of the liquid crystal according to the magnitude of the applied voltage.

Moreover, in a situation wherein liquid-crystal molecules are in an intermediate state between the state in which the molecules are parallel to the alignment film and the state in which the molecules are perpendicular to the alignment film, if it is likely that the scattered light having passed the liquid crystal is not linear polarization light but elliptic polarization light, the light which has become the elliptic polarization light due to the liquid crystal may be changed to the linear polarization light, by combining the 1/4 wave plate. Also, if the optical rotatory power is not required, for example, in the bright-field observation, the on or off of the optical rotatory power can be easily selected by applying or not applying a voltage.

FIG. 27(b) is a diagram showing an example of the optical microscope employing a polarization direction controller 665b in which according to the rubbing direction or directions of either one or both of alignment films 662 and 666, alignment of liquid-crystal molecules of liquid crystal 663 is controlled to thereby control the polarization direction. By selecting the rubbing direction, it is possible to create a distribution wave plate capable of precisely implementing a desired polarization state. Here, the rubbing direction is the direction, direction of the rubbing process to rub the alignment film using cloth wound on a roller; the liquid-crystal molecules have a characteristic to align in parallel with the rubbing direction.

Figure 29:
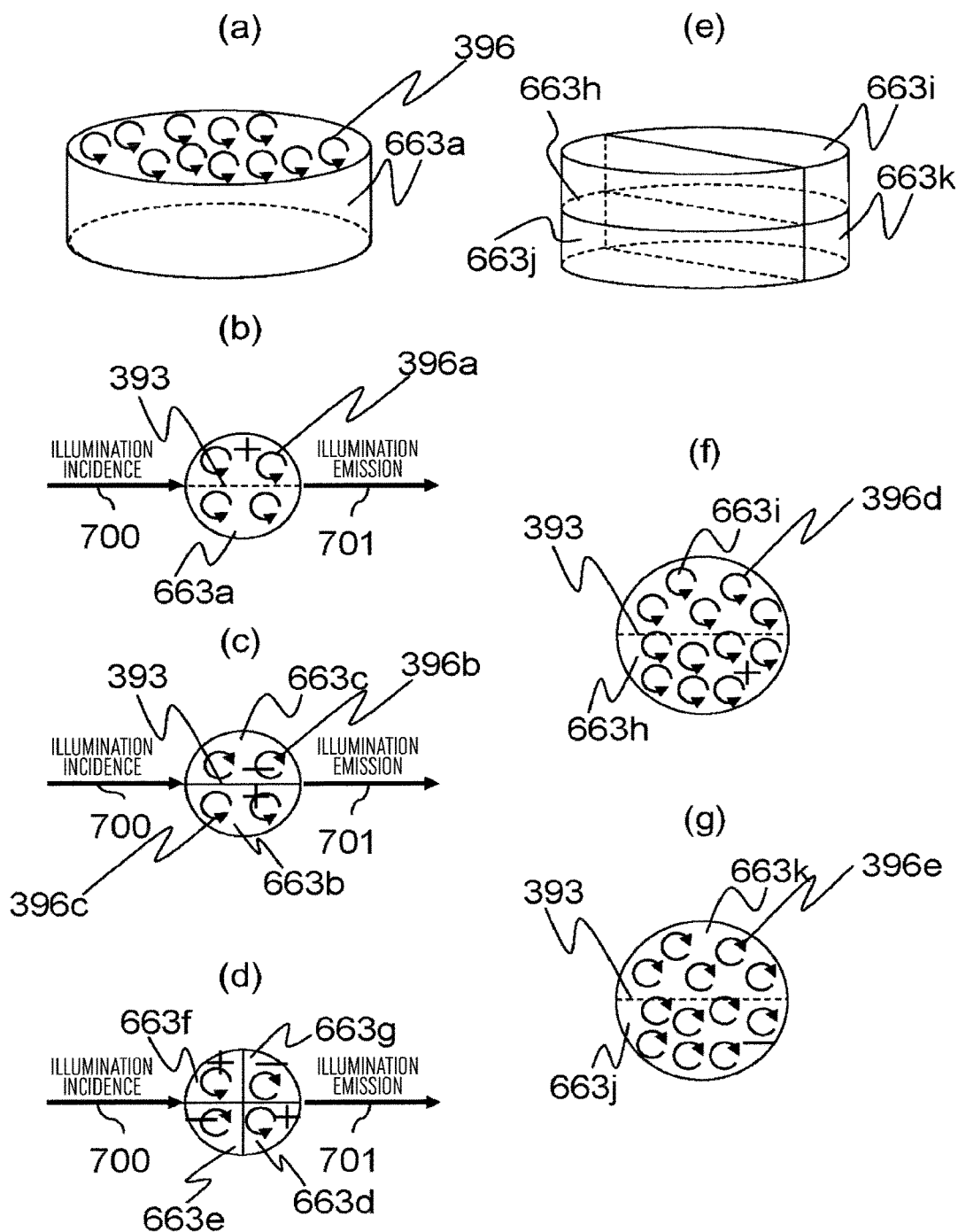
FIG. 29 is a diagram showing an example to explain a polarization direction controller using liquid crystal.

Next, FIG. 29 shows liquid crystal 663 of a polarization direction controller employing liquid crystal having chirality in which the optical rotatory angle is controllable by use of electrodes. There are employed a plurality of electrodes which apply a voltage to the liquid crystal, to thereby control the voltage to be applied to each place of the liquid crystal according to desired polarization. In FIG. 29, (a) and (b) show an example employing undivided liquid crystal 663 which has the optical rotatory power 396 and which is not divided. When the liquid crystal 663 is not divided, thickness of liquid crystal 663 is determined to obtain an optical rotatory angle in a range from 2Π to 0 or a range from 0 to −2Π.

As for an example of voltages to be applied to the liquid crystal, scattered light 775 from fine foreign matter is similar to the radial polarization light; hence, in the directions symmetric with respect to the axis 393 on the pupil plane 112 corresponding to the illumination incidence axis, the vibration directions of electric field vectors oppose to each other and the reduction in the intensity may take place due to the superimposition; therefore, in order to obtain a polarization direction to suppress the peak intensity reduction of the scattered light from foreign matter by aligning directions of electric field vectors, different voltages are applied to the respective electrodes. Or, the voltages of the respective electrodes are controlled to obtain a polarization direction to weaken scattered light from the sample surface. As a result, it is possible to increase the ratio of the peak intensity of the scattered light from the sample surface to that of the scattered light from the foreign matter.

In addition, it is also possible that by dividing the liquid crystal 663 into several partitions such that a voltage is applied to each of the partitions of the liquid crystal to control the direction of the liquid-crystal molecules of the liquid crystal, to thereby control the optical rotatory direction. FIG. 29(c) shows an example in which the liquid crystal is divided into two partitions with respect to an angle. It is only necessary in FIG. 29(c) that the controllable optical rotatory angles of the two partitions 663b and 663c of the liquid crystal are respectively in a range from Π to 0 and a range from 0 to FIG. 29(d) shows an example in which the liquid crystal 633 is divided into four partitions with respect to an angle. According to the number of partitions, the maximum controllable optical rotatory angle and the combination of the liquid crystal 633 are determined. Through the division, it is possible to control each divided area; hence, the optical rotatory angle can be more precisely controlled as a whole. Incidentally, the embodiment is not restricted by the number of partitions and the dividing method; they may be set according to necessity.

Further, the liquid crystal 633 is not limited to one layer, but a plurality of layers may be used. When a plurality of layers are employed, a voltage may be applied to each layer or may be applied to the plural layers at the same time. In FIG. 29; (e), (f), and (g) show an example in which the liquid crystal is divided into two partitions with respect to an angle and which includes two layers of liquid crystal. FIG. 29 (e) shows the dividing method. FIG. 29 (e) shows the upper-layer liquid crystal and FIG. 29 (f) shows the lower-layer liquid crystal. In this example, for the upper-layer liquid crystal 663i and 663h, liquid crystal having the plus-directional optical rotatory power 396d is employed; for the lower-layer liquid crystal 663k and 663j, liquid crystal having the minus-directional optical rotatory power 396e is employed. It is possible that both of the upper and lower layers are divided into two partitions with respect to the axis 393 on the pupil plane 112 corresponding to the illumination incidence axis and different voltages are respectively applied to the liquid crystal 663i, 663h, 663k, and 663j. For example, when it is desired to obtain the plus-directional optical rotatory power on the upper side of FIG. 29 (c) with respect to the axis 393 on the pupil plane 112 corresponding to the illumination incidence axis and the minus-directional optical rotatory power on the lower side of FIG. 29 (c) with respect to the axis 393 on the pupil plane 112 corresponding to the illumination incidence axis, it is only required that a voltage is applied to the liquid crystal 663i and 663j and no voltage is applied to the liquid crystal 663h and 663k. By piling up a plurality of layers of liquid crystal, the optical rotatory angle can be more precisely controlled.

Here, the liquid crystal 663 of the polarization controller of FIG. 27(a) is crystal having the optical rotatory power; hence, as for the alignment films 662 and 666 of the polarization controller of FIG. 27(a), an alignment film without rubbing is used for both thereof or for either one thereof.

Figure 30:
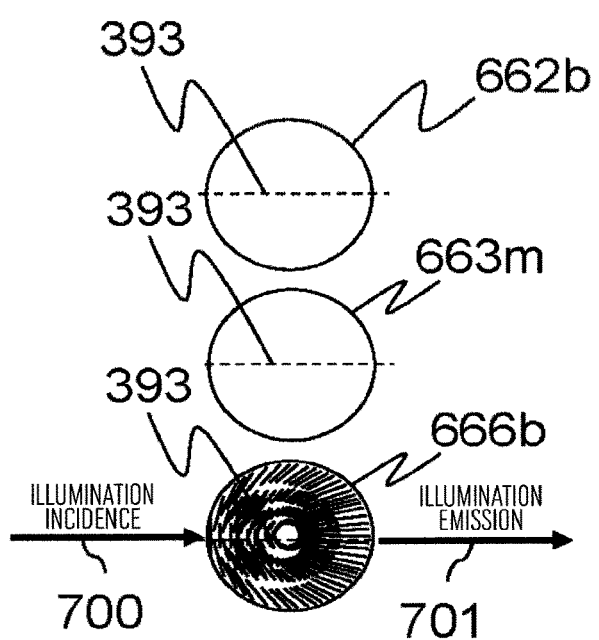
FIG. 30 is a diagram showing an example of a polarization direction controller which has optical rotatory power when not applied with a voltage and which loses the rotatory power when applied with a voltage.

FIG. 30 shows an example in which the radial polarization light is changed to the x polarization light by use of a polarization controller including liquid crystal which does not have the optical rotatory power 396 and which has width adjusted to obtain the function of the 1/4 wave plate. The scattered light from fine foreign matter is similar to the radial polarization light; hence, in the directions symmetric with respect to the axis 393 on the pupil plane 112 corresponding to the illumination incidence axis, the vibration directions of electric fields oppose each other and the intensity is reduced by the superimposition; to suppress the intensity reduction, there is employed the liquid crystal not having the optical rotatory power 396.

In this polarization controller, when no voltage is applied to the liquid crystal 663m, the optical rotatory direction can be changed from the radial polarization to the x polarization; on the other hand, although the optical rotatory direction can be changed when a voltage is applied thereto, if the voltage exceeds a threshold value, the optical rotatory power is lost. Here, the rubbing is conducted on the lower alignment film 666b to obtain the desired optical rotatory angle, and the rubbing is not conducted on the upper alignment film 666b for the operation.

Next, description will be given, by using FIG. 31 as an example, of a polarization controller employing liquid crystal to which no voltage is applied and for which the rubbing direction on the alignment film is selected for a desired optical rotatory angle. In the liquid crystal not having the chirality, the molecules of the liquid crystal align in the rubbing direction of the lower alignment film 666. FIG. 31(a) shows alignment of the liquid-crystal molecules when the rubbing direction of the lower alignment film differs from that of the upper alignment film by Π/2. The liquid-crystal molecules align along the alignment film, and an optical rotatory angle of Π/2 is obtained for the alignment film arrangement of FIG. 31(a).

Hence, as for the polarization controller which operates by selecting the rubbing direction of the lower alignment film 662 and that of the upper alignment film 666, it is possible to implement a more precise polarization controller to control polarization more precisely when compared with the controller employing the distribution 1/2 wave plate.

Figure 31:
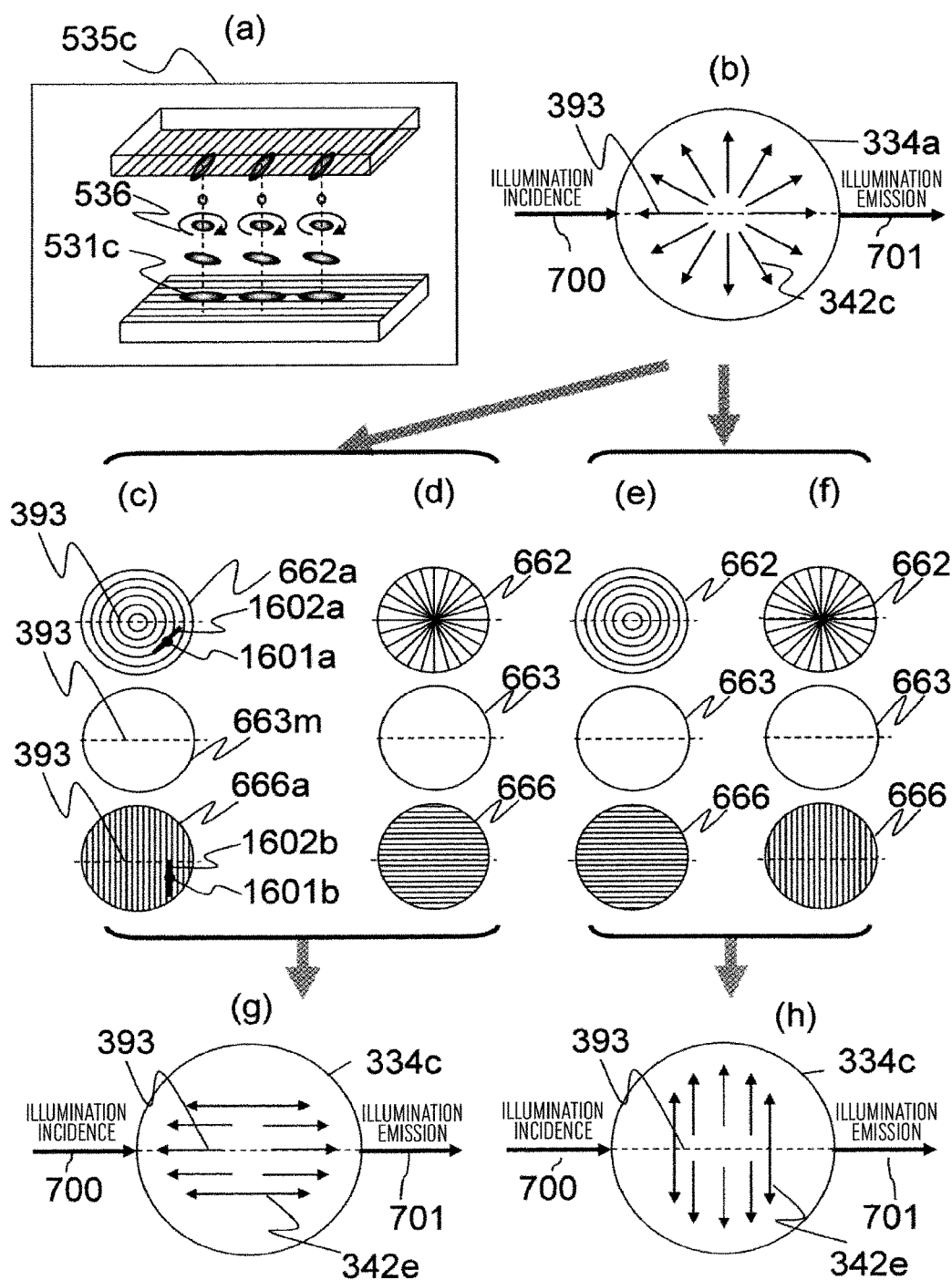
FIG. 31 is a diagram showing an example of a polarization direction controller using liquid crystal in which the polarization direction can be controlled based on the rubbing of the alignment film.

FIG. 31 is a diagram showing an example of the polarization direction controller in which the rubbing directions of the alignment films 662a and 666c are adjusted for the desired polarization directions. In FIG. 31, (c) and (d) as well as (e) and (f) respectively show the alignment film rubbing directions when the radial polarization light shown in FIG. 31(b) is changed into the x polarization light (FIG. 31(g)) and into the y polarization light (FIG. 31(h)). Description will be given of control of the polarization direction according to the rubbing direction by referring to FIG. 31(c). There is shown an example of the polarization controller employing liquid crystal not having the optical rotatory power to suppress an event in which since the scattered light from fine foreign matter is similar to the radial polarization light, the vibration directions of electric field vectors oppose each other in the directions symmetric with respect to the axis 393 on the pupil plane 112 corresponding to the illumination incidence axis and the intensity is reduced by the superimposition.

The rubbing directions of the alignment films 662a and 662b are determined such that the difference between the inclinations of the rubbing directions of the alignment films 662a and 662b at arbitrary points on the pupil plane 112 or in the neighborhood thereof is equal to the desired optical rotatory angle.

An electric field vector 342c at a point 1601a and at an arbitrary point of time is changed to an electric field vector 342e by use of the polarization direction controller 665b. At the point 1601, the rubbing direction angular difference between the alignment films 662a and 662b is Π/4. Hence, the electric field vector 342c changes in the polarization direction by Π/4, and there is obtained the linear polarization light 342e of the x polarization.

Next, description will be given of a polarization controller employing a magnetooptical effect.

Figure 32:
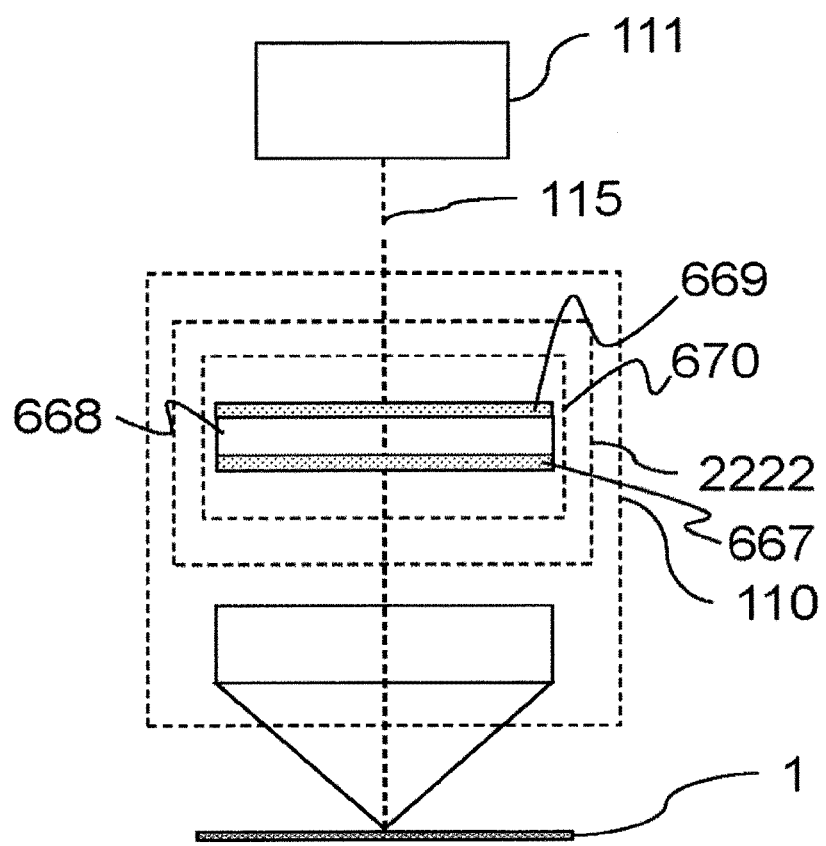
FIG. 32 is a diagram showing an example in which a polarization direction controller using a transparent magnetic substance is arranged in the vicinity of the optical microscope pupil plane 112 in the first embodiment of the present invention.

FIG. 32 shows an example of arrangement of a polarization direction controller in which a transparent magnetic substance using a magnetooptical effect is employed in place of the 1/2 wave plate 331 and the 1/4 wave plate 332 of FIG. 25. In this example, by controlling the polarization direction of the transparent magnetic substance 668 intercalated between transparent substrates 667 and 669, the polarization direction is controlled by use of the Faraday rotation.

Figure 33:
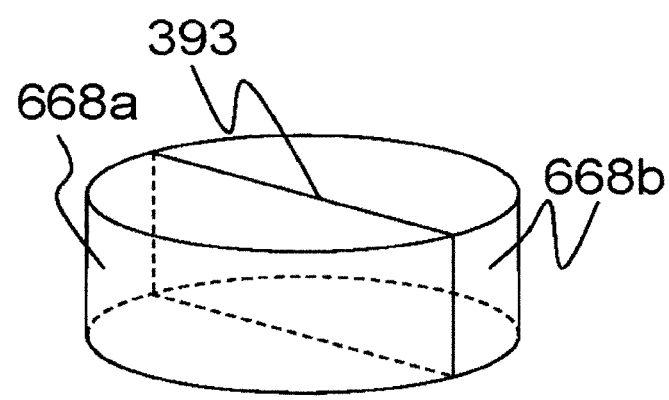
FIG. 33 is a diagram showing an example of a polarization direction controller using a transparent magnetic substance.
Figure 33:
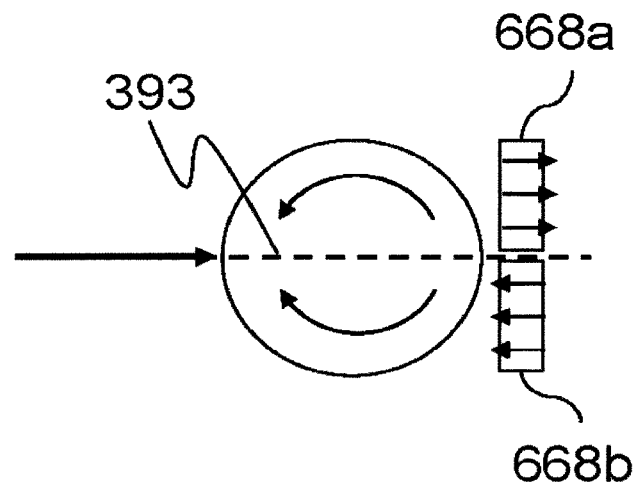

Further, FIG. 33 shows an example of use of a transparent magnetic substance symmetrically divided with respect to the axis 393 on the pupil plane 112 corresponding to the illumination incidence axis. Through an operation in which the transparent magnetic substances 668a and 668b symmetrically arranged with respect to the axis 393 on the pupil plane 112 corresponding to the illumination incidence axis are magnetized in the symmetric directions, there can be obtained an optical rotatory angle 780 symmetric with respect to the axis 393 on the pupil plane 112 corresponding to the illumination incidence axis. In the directions symmetric with respect to the axis 393 on the pupil plane 112 corresponding to the illumination incidence axis, the vibration directions of electric field vectors oppose each other, and when the scattered light is superimposed, the intensity of the y polarization light of the scattered light from the defect is reduced; however, the reduction in the peak intensity of the scattered light can be suppressed by selecting, by use of the polarization direction controller employing the magnetooptical effect, the direction of magnetization to align the directions of magnetic field vectors in one direction. Incidentally, the direction of magnetization is not necessarily parallel to the pupil plane 112. Also, the number of divisions of the transparent magnetic substance may be one or more. Further, the number of layers of the transparent magnetic substance is not limited to one; a plurality of layers may be piled up.

In addition, the direction of magnetization is controlled by applying an external magnetic field, by applying stress onto the crystal using a piezoelectric actuator or the like, by applying an electric field, or by applying an external magnetic field and by applying stress onto the crystal using a piezoelectric actuator or the like. Incidentally, when the optical rotatory power is not required in the bright-field observation or the like, the optical rotatory power can be easily removed by not applying the stress, by not applying the electric field, or by not applying the external magnetic field.

Here, as the spatial filter described above, there may be employed a distribution filter implemented by combining a polarization element with a light block plate in which the ratio between the foreign matter scattered light quantity and the substrate surface scattered light quantity is derived through scattered light simulation or actual measurement such that an area with the ratio more than a threshold value transmits light and an area with the ratio between the foreign matter scattered light and the substrate surface scattered light less than a threshold value blocks light. By removing the area having a small ratio between the foreign matter scattered light and the substrate surface scattered light, it is possible to increase the ratio between the foreign matter scattered light quantity and the substrate surface scattered light quantity in the overall pupil plane 112.

Figure 34:
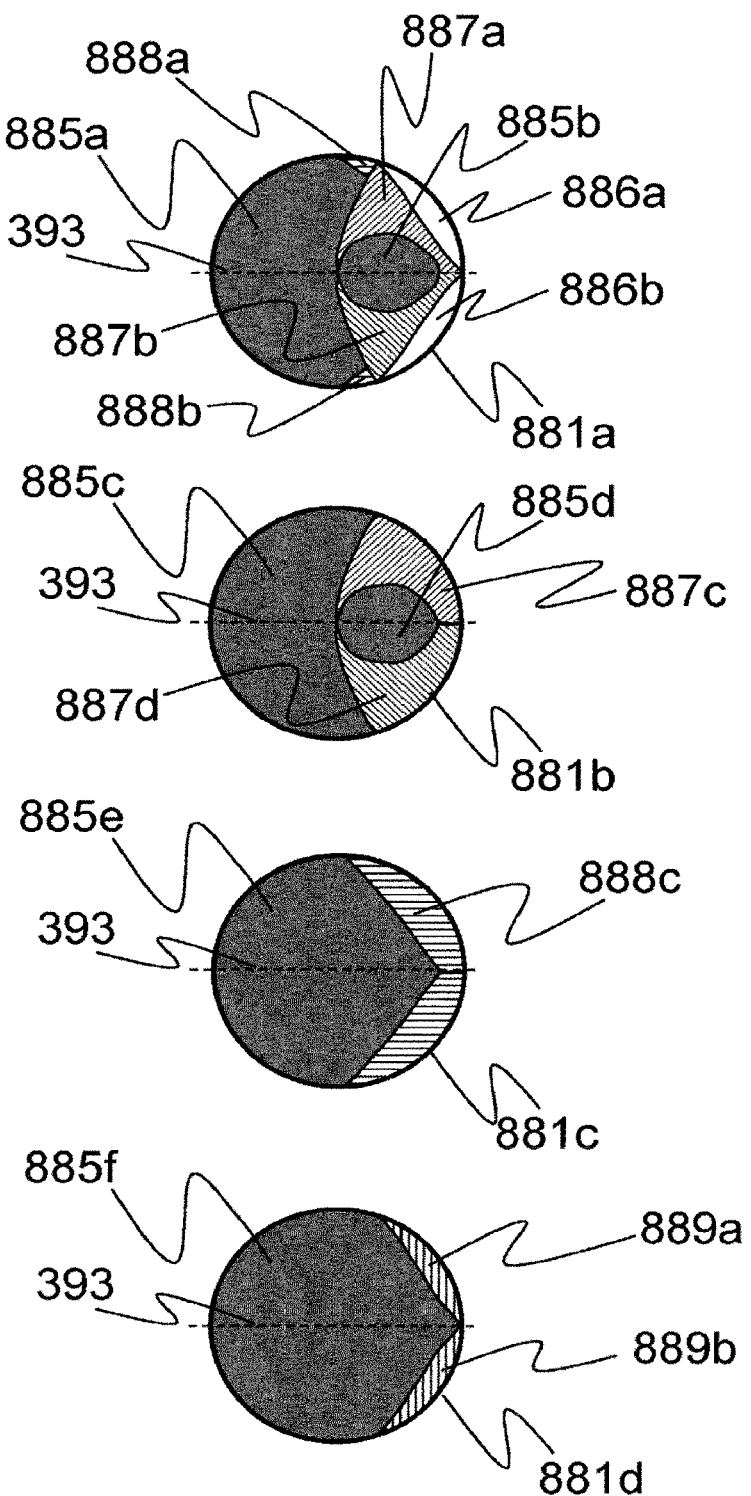
FIG. 34 is a diagram showing an example of a distribution filter including a combination of a polarization element and a mask in which the ratio between the foreign matter scattered light and the substrate surface scattered light is derived from scattered light simulation so as to transmit light in a region with the ratio more than a threshold value and to block light in a region with the ratio between the foreign matter scattered light and the substrate scattered light less than a threshold value.

FIG. 34 shows an example of the distribution filter including a combination of a polarization element and a light block plate.

Here, discussion has been given on a combination of a polarization element and a light block plate in which the ratio between the foreign matter scattered light quantity and the substrate surface scattered light quantity is derived for each of radial polarization light, azimuth polarization light, x polarization light, and y polarization light such that an area with an arbitrary ratio more than a threshold value transmits light and an area with the ratio between the foreign matter scattered light and the substrate surface scattered light less than an arbitrary threshold value blocks light. Also, in a situation in which the ratio between the foreign matter scattered light quantity and the substrate surface scattered light quantity is more than an arbitrary threshold value for both of the x polarization light and the y polarization light, the polarization element and the light block plate are not employed.

A distribution spatial filter 881a obtained according to the results of the scattered light simulation used to draw FIG. 21 includes a combination of areas 886a and 886b with no polarization element and no light block plate, light block plates 885a and 885b, a polarization element 887a having a transmission polarization axis inclined 2/Π relative to the x polarization light, a polarization element 887b having a transmission polarization axis inclined 2/Π relative to the x polarization light, and polarization elements 888a and 888b including transmission polarization elements to transmit x polarization light.

Moreover, a distribution filter 881b as another distribution spatial filter is an example of the distribution filter obtained as a result of discussion on the combination of a polarization element and a light block plate in which the ratio between the foreign matter scattered light quantity and the substrate surface scattered light quantity is derived for radial polarization light based on the results of the scattered light simulation used to draw FIG. 21 such that an area with an arbitrary ratio more than a threshold value transmits light and an area with the ratio between the foreign matter scattered light and the substrate surface scattered light less than an arbitrary threshold value blocks light; and the filter includes a combination of light block plates 885c and 885d, a polarization element 887c having a transmission polarization axis inclined 2/Π relative to the x polarization light, and a polarization element 887d having a transmission polarization axis inclined 2/Π relative to the x polarization light. Here, when a polarization element having a transmission polarization axis which radially extends (in the radial direction) is employed for the polarization elements 887a and 887c having a transmission polarization axis inclined Π/2 relative to the x polarization light and the polarization elements 887b and 887d having a transmission polarization axis inclined Π/2 relative to the x polarization light, the ratio of the scattered light quantity from the defect to that from the sample surface is improved.

A distribution filter 881c is an example of the distribution filter obtained as a result of discussion on the combination of a polarization element and a light block plate in which the ratio between the foreign matter scattered light quantity and the substrate surface scattered light quantity is derived for x polarization light based on the results of the scattered light simulation used to draw FIG. 21 such that an area with an arbitrary ratio more than a threshold value transmits light and an area with the ratio between the foreign matter scattered light and the substrate surface scattered light less than an arbitrary threshold value blocks light; and the filter includes a combination of a light block plate 885e and a polarization element 888c having a transmission polarization element to transmit x polarization light.

A distribution filter 881d is an example of the distribution filter obtained as a result of discussion on the combination of a polarization element and a light block plate in which the ratio between the foreign matter scattered light quantity and the substrate surface scattered light quantity is derived for y polarization light based on the results of the scattered light simulation used to draw FIG. 21 such that an area with an arbitrary ratio more than a threshold value transmits light and an area with the ratio between the foreign matter scattered light and the substrate surface scattered light less than an arbitrary threshold value blocks light; and the filter includes a combination of a light block plate 885f and polarization elements 889a and 889b having a transmission polarization element to transmit y polarization light. Incidentally, this embodiment is not restricted by these combinations of the polarization element and the light block plate, but any appropriate combination may be selected according to the scattered light distribution.

As a result of discussion on the combination of a polarization element and a light block plate in which the ratio between the foreign matter scattered light quantity and the substrate surface scattered light quantity is derived for azimuth polarization light based on the results of the scattered light simulation used to draw FIG. 21 such that an area with an arbitrary ratio more than a threshold value transmits light and an area with the ratio between the foreign matter scattered light and the substrate surface scattered light less than an arbitrary threshold value blocks light, there have not been any coordinates on the pupil plane 112 where the threshold value is exceeded.

Next, description will be given of a distribution filter including a combination of a polarization element and a light block plate in which the pupil plane 112 or the pupil plane 112 is divided into arbitrary areas. By dividing the pupil plane 112 or the pupil plane 112 into arbitrary areas, there is obtained more feasibility when compared with the distribution filter of FIG. 34.

Figure 35:
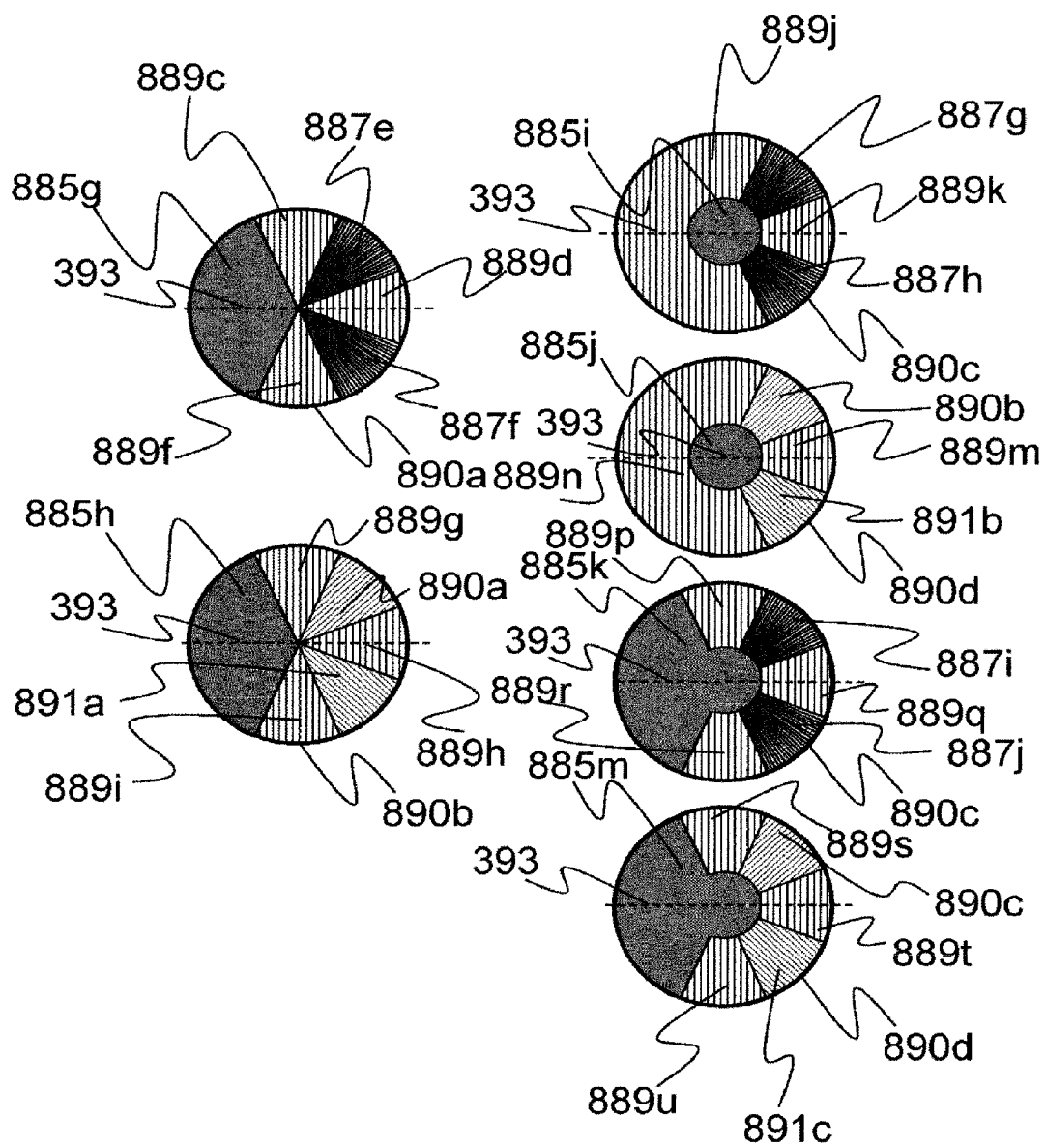
FIG. 35 is a diagram showing an example of foreign matter scattered light and a substrate distribution polarization element in which the pupil plane 112 is divided into regions and the ratio between the foreign matter distributed light and the substrate surface distributed light is derived for each region through scattered light simulation such that there is selected a polarization direction in which the ratio between the foreign matter scattered light and the substrate scattered light is large, and light is transmitted in a region with the ratio more than a threshold value.

FIG. 35 shows an example of a distribution filter including a combination of a polarization element and a light block plate in which the ratio between the foreign matter scattered light quantity and the substrate surface scattered light quantity is derived for radial polarization light, azimuth polarization light, x polarization light, and y polarization light for each of the arbitrary areas on the pupil plane 112 or the pupil plane 112 through scattered light simulation or actual measurement such that an area with the ratio more than a threshold value transmits light and an area with the ratio between the foreign matter scattered light and the substrate surface scattered light less than a threshold value blocks light.

Here, discussion has been given on a combination of a polarization element and a light block plate in which the ratio between the foreign matter scattered light quantity and the substrate surface scattered light quantity is derived for each of radial polarization light, azimuth polarization light, x polarization light, and y polarization light such that an area with an arbitrary ratio more than a threshold value transmits light and an area with the ratio between the foreign matter scattered light and the substrate surface scattered light less than an arbitrary threshold value blocks light. Further, in a situation in which the ratio between the foreign matter scattered light quantity and the substrate surface scattered light quantity is more than an arbitrary threshold value for both of the x polarization light and the y polarization light, the polarization element and the light block plate are not employed.

Distribution filters 890a and 890b are examples in which the pupil plane 112 is divided into eight areas in the radial direction such that the filters are implemented by appropriately combining a polarization element and a light block plate of radial polarization light, azimuth polarization light, x polarization light, or y polarization light for each of the eight divided areas. Moreover, distribution filters 890c to 890f are examples in which the pupil plane 112 is divided into eight areas in the radial direction and into two areas in the circumferential direction such that the filters are implemented by appropriately combining a polarization element and a light block plate of radial polarization light, azimuth polarization light, x polarization light, or y polarization light for each of the 16 divided areas.

In this regard, in the distribution filters, it is possible to control the polarization direction by a wave plate and to select polarization by a polarization plate. By combining the wave plate with the polarization element, it is possible to simplify the transmission polarization axis direction of the polarization element employed to increase the ratio between the scattered light quantity from foreign matter and the scattered light quantity from the substrate surface. For example, in areas 887e and 887f of the distribution filter 890a to transmit light of radial polarization, by placing a distribution 1/2 wave plate to convert the vibration direction of the electric field from the radial polarization into the y polarization, there may be used a distribution filter including a combination of a 1/2 wave plate, a polarization element for y polarization, and a light block plate.

Also, it is possible to employ, in place of the 1/2 wave plate of the distribution filter, a polarization direction controller using liquid crystal or a polarization direction controller including a transparent substance using the magnetooptical effect described above. In this situation, the polarization direction can be controlled more precisely when compared with the 1/2 wave plate. In addition, the on or off of the optical rotatory power can be easily selected. Further, it is also possible that a phase shifter is combined with the distribution filter including the combination of a wave plate, a polarization element, and a light block plate. By combining the phase shifter with the distribution filter, when the scattered light having passed the distribution filter interferes with each other, it is possible that the reduction in the intensity due to the superimposition is suppressed and the peak intensity is strengthened by the superimposition. Or, photonic crystal having a function of a phase shifter, a polarization element, a light block plate, a wave plate, or a combination thereof may be employed as the distribution filter. By using the photonic crystal, it is possible to implement a distribution filter having precise polarization selectivity and a precise polarization direction control function.

Due to reduction in size of the foreign matter to be detected, due to utilization of the spatial filter 114, or due to both thereof, the intensity of the scattered light from the foreign matter is lowered; hence, a highly sensitive sensor 111 may be employed to multiply very low intensity of the scattered light from fine foreign matter or to suppress noise caused by the sensor 111. By using the highly sensitive sensor 111, it is possible to increase the ratio of the scattered light from the defect to the noise caused by the sensor. For example, for the highly sensitive sensor 111, it is only necessary to appropriately employ a Cooled CCD camera, an Intensified CCD camera (ICCD camera), a Silicon Intensified CCD camera (SIT camera), an Electron Bombardment CCD camera (EB-CCD camera), or an Electron Multiplier CCD camera (EM-CCD camera).

The various distribution filters described above may be employed as a single unit or in combination with each other according to necessity, and are applicable to the inspection devices of the respective embodiments described above as well as to the inspection devices of respective embodiments, which will be described later.

Fifth Embodiment

Figure 36:
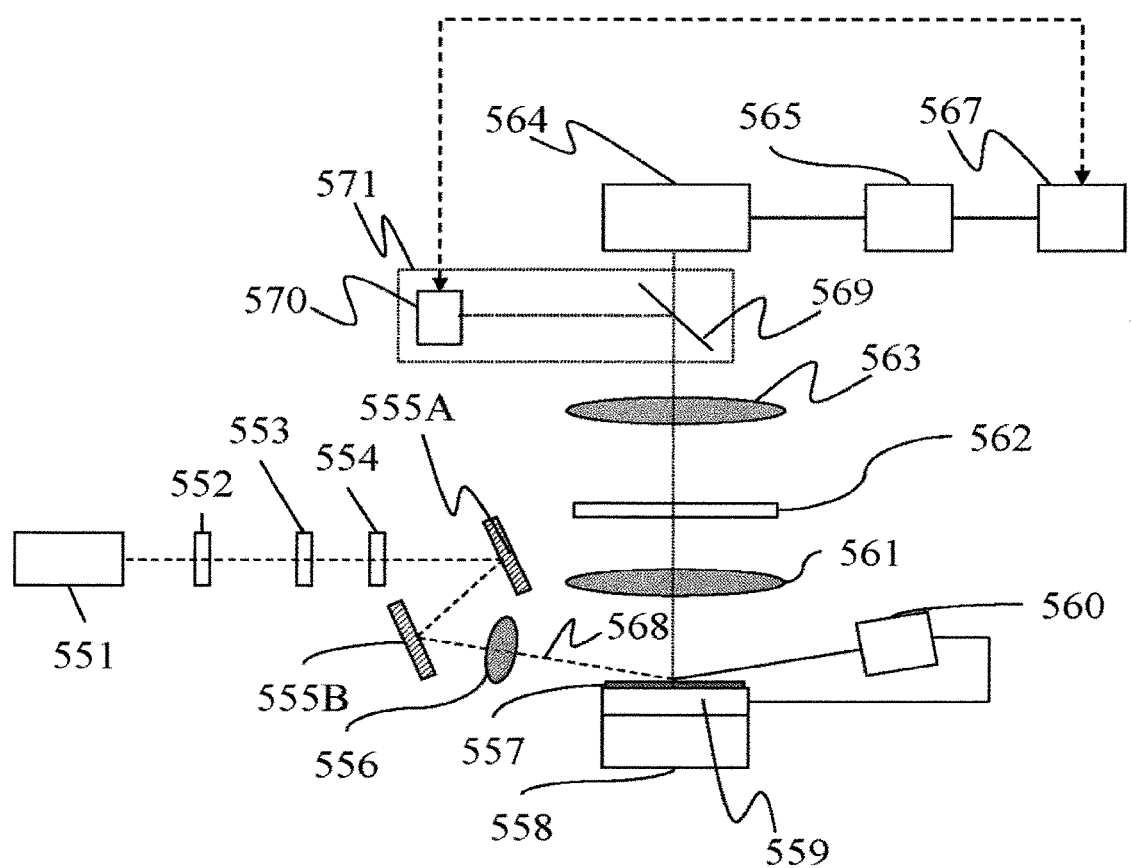
FIG. 36 is a diagram showing a configuration example of a defect detection device of a defect observation device in the fifth embodiment of the present invention.

Description will be given of a defect observation device in a fifth embodiment according to the present invention by referring to FIG. 36. As for FIG. 36, the electron microscope 5 and the like are omitted and only a defect detection device will be described. An inspection device to inspect a surface of or a defect on an inspection target sample 557 includes, according to necessity, a illumination optical system including a laser 551, an expander 552, an attenuator 553, a polarization control element 554, mirrors 555A and 555B, and a lens 556; a stage including a Z stage 558 and an XY stage 559; a sample height measurement unit 560; a detection optical system including, according to necessity, an objective 561, a spatial filter 562, an imaging lens 563, and a sensor 564; a signal processing unit 565, and a monitor 567. In addition, the inspection device includes, according to necessity, a detection system monitoring unit 571 which includes a half-silvered mirror 569 and a sensor 570 and which measures a state of the detection optical system; further, although not shown, a illumination system monitoring unit to measure a state of the illumination optical system and a control unit 800 to control respective associated units, which will be described later.

First, description will be given of the configuration of the illumination optical system. The laser 551 emits illumination light 568 in a direction inclined with respect to the direction of the normal of the inspection target sample, to form a desired beam of a spot, a linear form, or the like on a surface of the inspection target sample 557. The expander 552 expands the illumination light 568 to a parallel flux of light according to a fixed magnification factor. The attenuator 553 is an attenuator to control the quantity and intensity of illumination light 568 having passed the expander 552. The polarization control element 554 is an element which changes the direction of molecules of liquid crystal by rotating a polarization plate or a wave plate or by conducting voltage on and off control to change the polarization direction of light incident to the element, to thereby control the polarization state. The mirrors 555A and 555B are a group of reflection mirrors employed, when the illumination light 568 after the polarization control (control of the electric field phase and amplitude) is emitted onto the inspection target sample 557, to adjust the lighting angle. Here, although two mirrors are used in this example, it is also possible that no mirror is employed in the configuration; or, one mirror or three or more mirrors may be used in the configuration. The lens 556 is a lens to focus the illumination light 568 onto a radiation position immediately before the light is emitted onto the inspection target sample 557.

Next, description will be given of the configuration of the detection optical system. The objective 561 is an objective lens which focuses, in the direction of the normal (from above) of the inspection target sample 557, light scattered or light diffracted by foreign matter, a defect, or a pattern on the inspection target sample 557 due to radiation of the illumination light 568 from the laser 551. In this situation, when the inspection target sample 557 such as a semiconductor device to be inspected by this dark-field defect inspection device includes a repetitive pattern, diffracted light caused by the repetitive pattern is focused with a regular interval onto the emission pupil of the objective 561. The spatial filter 562 is a filter to block light of the repetitive pattern in the vicinity of the pupil plane 112 or a filter to control and to select the polarization direction for all of, part of, or light of a particular polarization of the light reflected by the inspection target sample. The imaging lens 563 is a lens to focus light which is scattered or diffracted by other than the repetitive pattern (for example, a position of occurrence of failure) and which has passed the spatial filter 562, to thereby form an image on the sensor 564. The sensor 564 is an optical sensor to transmit the image focused and produced by the imaging lens 563 as electronic information to the signal processing unit 565. The kinds of the optical sensors are CCD and CMOS in general; however, here, any kind thereof is available.

The signal processing unit 555 includes a circuit to convert image data received from the sensor 564 into a state which can be displayed on the monitor 567.

The XY stage 559 is a stage to place thereon the inspection target sample 557; by moving the XY stage 559 in the direction of a plane, the inspection target sample 557 is scanned. Further, the Z stage 558 is a stage to perpendicularly (in the z direction) move an inspection reference plane (a plane on which the inspection target sample 557 is placed) of the XY stage 559.

The sample height measurement unit 560 is a measuring unit to measure the inspection reference plane of the XY stage 559 and the height of the inspection target sample 557. By use of the Z stage 558 and the sample height measurement unit 560, it is possible to provide an automatic focus function to automatically conduct the focusing operation.

Next, description will be given of overall operation of this inspection device.

First, the illumination light 568 from the laser 551 is emitted onto a surface of the inspection target sample 557 in a direction inclined with respect to the direction of the normal of the inspection target sample, to form a desired beam on the inspection target sample 557. Light scattered or light diffracted by foreign matter, a defect, or a pattern on the inspection target sample 557 due to the beam is focused by the object 561 over the inspection target sample. When the inspection target sample 557 includes a repetitive pattern, diffracted light caused by the repetitive pattern is focused with a regular interval onto the emission pupil of the objective, and is hence blocked by the spatial filter 562 placed on the pupil plane 112. On the other hand, light scattered or diffracted by other than the repetitive pattern passes the spatial filter 562 and is fed to the imaging lens 563, to thereby form an image on the sensor 564.

The inspection target sample 557 is placed on the XY stage 559 and is scanned by use of the XY stage 559, to thereby obtain a two-dimensional image of the scattered light from the inspection target sample 557. In the operation, the distance between the inspection target sample 557 and the objective 561 is measured by the sample height measurement unit 560 and is then adjusted by the Z stage 558.

The two-dimensional image obtained by the sensor 564 is classified by the signal processing unit 565 according to the foreign matter kind and the defect kind such that the size of the foreign matter or the defect is obtained, and the result is displayed on the monitor 567.

Figure 37:
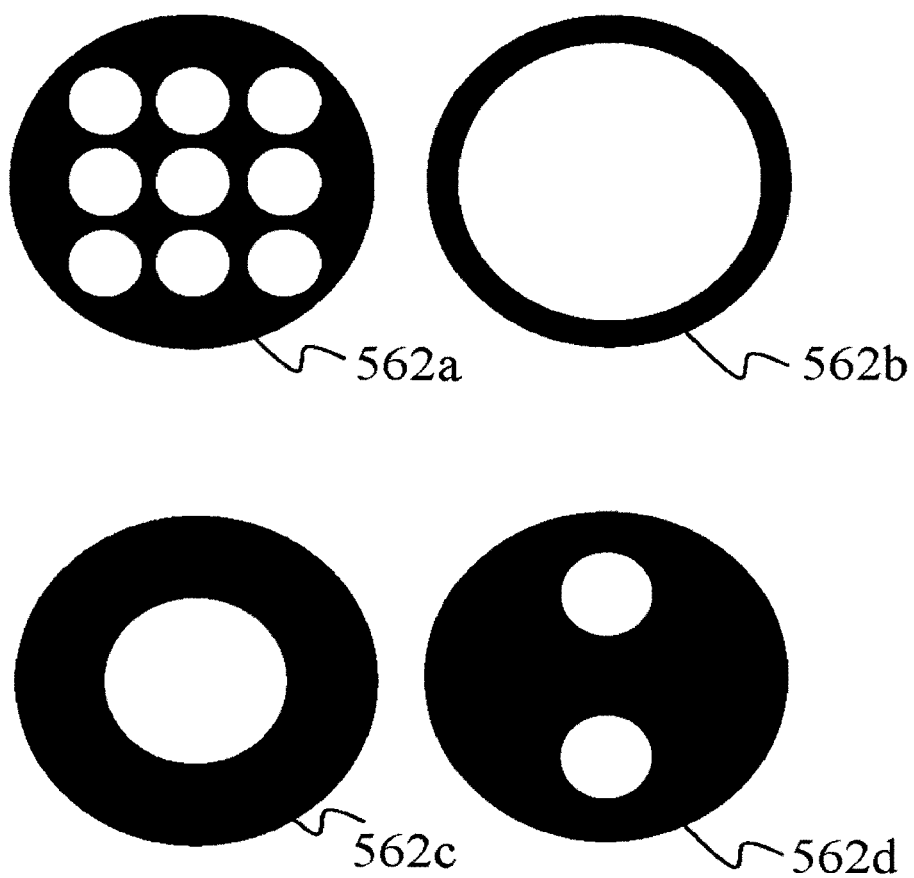
FIG. 37 is a diagram showing an example of the spatial filter to be disposed in the vicinity of the pupil plane 112 to exclude scattered light caused by the pattern.

Here, FIG. 37 shows an example of the contour of the spatial filter 562 arranged in the proximity of the pupil plane 112 to remove the scattered light caused by the pattern. As for the example of each spatial filter shown in FIG. 37, the filter is arranged on the pupil plane 112 or in the proximity thereof and a dark area indicates a light block zone and an open area indicates a light flux transmission zone. This diagram shows an example in which nine small openings are disposed in the central area (562*a*), an example in which a large opening is disposed in the central area (562*b*), an example in which a middle-sized opening is disposed in the central area (562*c*), and an example in which two small openings are disposed in the central area (562*d*); however, the embodiment is not restricted by these examples; the openings may be disposed in the form of perpendicular or longitudinal stripes, and the number and the size of openings may be set according to necessity. Incidentally, the image on the pupil plane 112 represents angular components of diffracted or scattered light of the inspection target sample; hence, by determining positions and sizes of openings to be disposed, it is possible to select the diffracted or scattered light of the inspection target sample. In addition, it is also possible that various distribution filters 2222 are used in combination with the spatial filter 562 according to necessity, and these distribution filters 2222 may be employed in place of the spatial filter 562.

Figure 38:
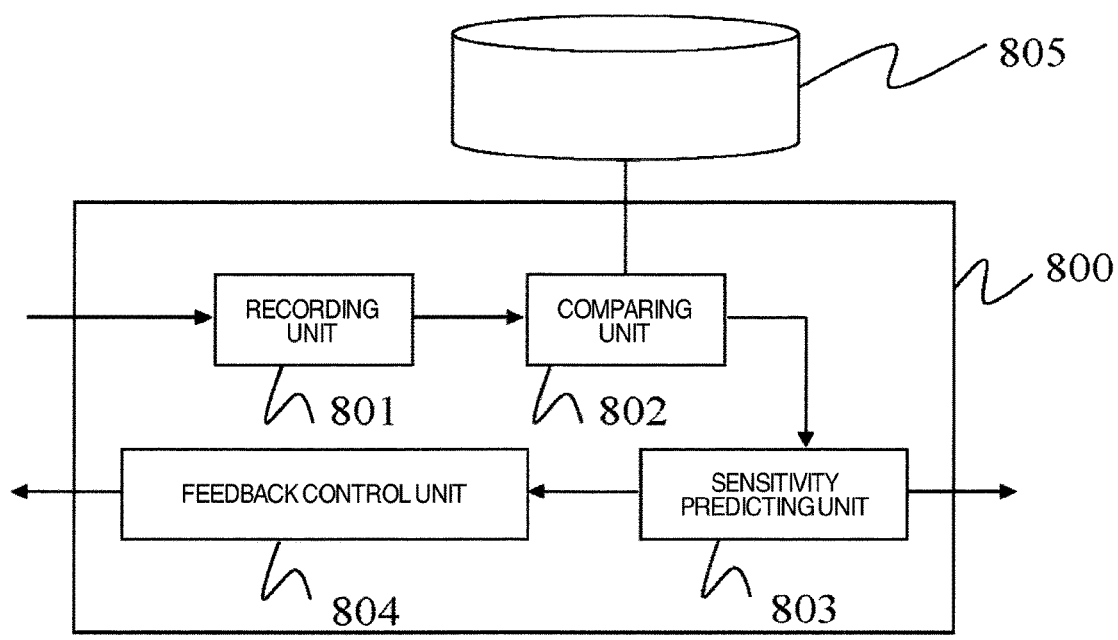
FIG. 38 is a block diagram showing an inner configuration of a controller according to the fifth embodiment of the present invention.

Next, description will be given of the control unit 800 according to the fifth embodiment of the present invention by referring to FIG. 38. FIG. 38 is a block diagram showing an internal configuration of the control unit 800; the control unit 800 includes, according to necessity, a recording unit 801, a comparing unit 802, a sensitivity predicting unit 803, and a feedback control unit 804.

The recording unit 801 receives inputs of data items from the illumination system monitoring unit and the detection system monitoring unit 571 which have conducted monitoring operations, and records these data items. The comparing unit 802 receives inputs of data recorded in the recording unit 801 and compares the data with an ideal value in a database 805. Incidentally, before the processing in the comparing unit 802, characteristics of the light source and elements in the monitoring operation are beforehand calculated. The sensitivity predicting unit 803 estimates and predicts the present device sensitivity based on the difference between the record data and the ideal value. If the difference between the record data and the ideal value is in an allowable range, respective associated units of the illumination optical system and the detection optical system are controlled to start inspection. If the difference is beyond the allowable range, the feedback control unit 804 performs a feedback control operation for the respective associated units of the device according to the predicted sensitivity predicted by the sensitivity predicting unit 803.

In this regard, the database 805 is a database of ideal values to be used by the comparing unit 802; to this database 805, ideal values are beforehand inputted through logical calculations, optical simulation, and the like. In the operation, the inspection target sample is modeled in an optical simulator to derive the intensity of scattered light and the like from the inspection target sample taking place depending on conditions of the illumination optical system, to calculate intensity of light detected by a detector. The parameters of ideal values in the database 805 include information pieces of the intensity distribution, the polarization state distribution, the focal distance of the imaging lens 563, and the sensitivity of the sensor 564 of the illumination optical system. It is required to beforehand obtain characteristics of these parameters.

Figure 39:
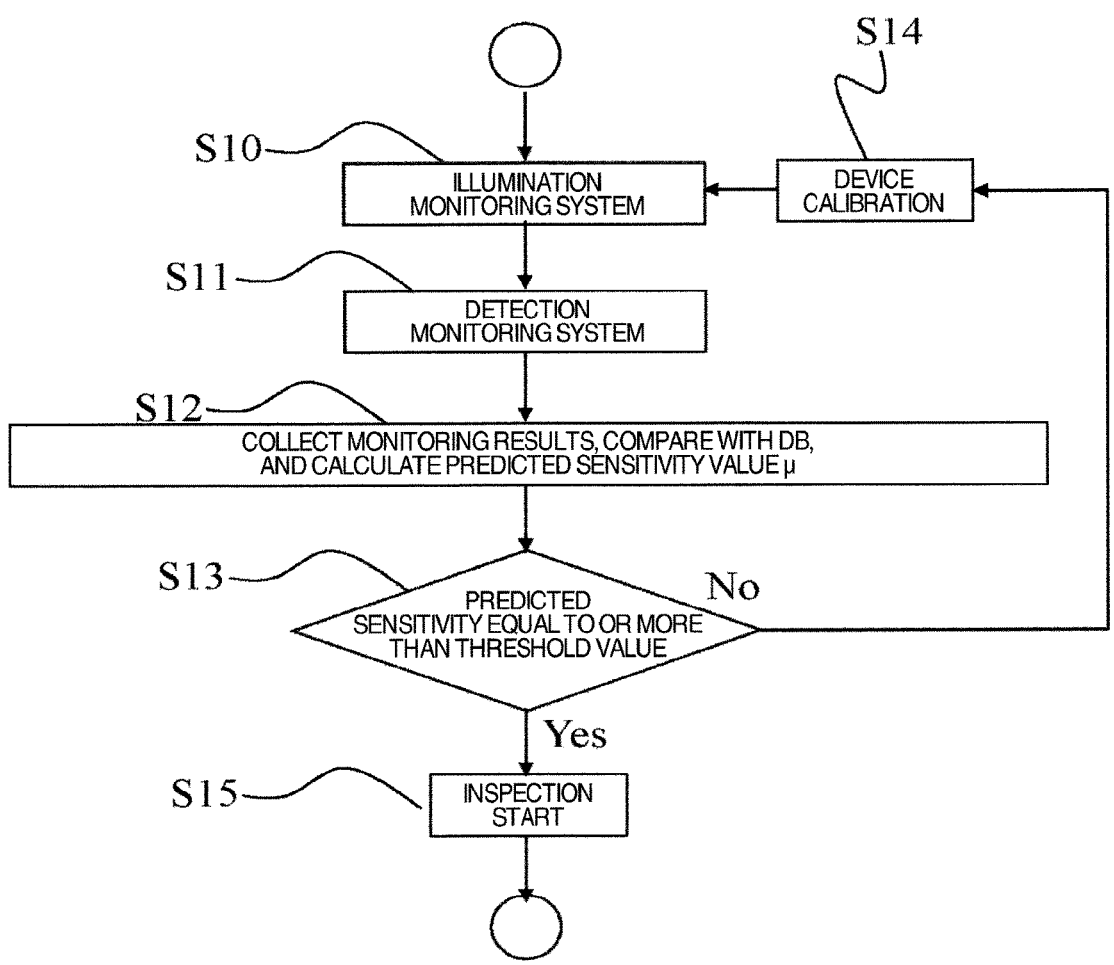
FIG. 39 is a flowchart showing a monitoring processing procedure in the defect observation device according to the fifth embodiment of the present invention.

Next, by referring to the flowchart of FIG. 39, description will be concretely given of a monitoring processing procedure in the dark-field defect detection device according to the fifth embodiment of the present invention.

First, the lighting-system monitoring unit monitors the state of the illumination system (step S10). Further, the detection-system monitoring unit 571 measures the state of the detection system (step S11). Measurement results obtained in steps S10 and S11 are sent to the comparing unit 802. The comparing unit 802 compares these measurement results with ideal values in the database 805 to further predict the detection sensitivity based on "difference" between the ideal values and these measurement results (step S12). The comparing unit 802 then judges if the predicted detection sensitivity is larger or smaller than a threshold value arbitrarily set (step S13).

If the predicted sensitivity is equal to or less than the threshold value, the optical system is calibrated (step S14), and then control returns again to step S10. In this connection, if all positions requiring calibration can be automatically controlled, it is also possible to automatically carry out all operations of calibration. In this operation, it is only required that the calibration positions are beforehand determined through a logical calculation or optical-system simulation. On the other hand, if the predicted sensitivity is equal to or more than the threshold value, inspection is started for the illumination system and the detection system (step S15).

As above, the invention devised by the present inventor has been specifically described based on embodiments; however, the present invention is not restricted by the embodiments above, and it is to be appreciated that various changes are possible without departing from the gist of the present invent.

REFERENCE SIGNS LIST

1 . . . Sample 2 . . . Sample holder 3 . . . Stage 4 . . . Optical height detection device 5 . . . Electron microscope 6 . . . Vacuum chamber 7 . . . Optical height detection device 10 . . . Control system 11 . . . User interface 14 . . . Optical microscope 101 . . . Dark-field lighting unit 102 . . . Light introduction mirror 104 . . . Mirror 105 . . . Objective 106 . . . Height control unit 108 . . . Half-silvered mirror 109 . . . Bright-field illumination 110 . . . Imaging optical system 111 . . . Solid-state imaging element 113 . . . Lens group 114 . . . Distribution polarization element 116 . . . Imaging lens 117 . . . Objective rotation unit 118 . . . Liquid-crystal controller 111 . . . Polarization plate 501 . . . Illumination light source 502 . . . Optical filter 503 . . . Wave plate

507 . . . Lens group 751 . . . Light source 702 . . . Focusing lens 703 . . . Slit 704 . . . Projection lens 705 . . . Light reception lens 706 . . . Detector 401 . . . Filter changeover unit 402 . . . Holder 405 . . . Distribution polarization element holder 2222 . . . Distribution filter 391 . . . Phase shifter 742, 744 . . . Area-division-type distribution polarization element 331 . . . Distribution 1/2 wave plate 332 . . . Distribution 1/4 wave plate 665 . . . Polarization direction controller employing liquid crystal 670 . . . Polarization direction controller employing transparent magnetic substance

The invention claimed is:

1. An inspection device, comprising:
   an illumination optical system configured to emit light onto a surface of a sample;
   a detection optical system configured to detect scattered light from the sample caused by the illumination optical system;
   a first filter disposed near a pupil plane of the detection optical system, the first filter having a plurality of regions of different transmission characteristics regarding the scattered light;
   a second filter disposed near the pupil plane of the detection optical system, the second filter having a plurality of regions with different polarization characteristics regarding the scattered light; and
   a sensor configured to detect scattered light filtered by the first and second filters.

2. The inspection device of claim 1, wherein the first and second filters comprise characteristics wherein a ratio between an amount of scattered light caused by a foreign matter or a defect present on the sample and an amount of scattered light from the surface of the sample is greater than a prescribed threshold value.

3. The inspection device of claim 2, wherein the first and second filters comprise characteristics wherein a component of light with a ratio between an amount of scattered light caused by a foreign matter or a defect present on the sample and an amount of scattered light from the surface of the sample being less than a prescribed threshold value is blocked.

4. The inspection device of claim 1, wherein the plurality regions with different polarization characteristics of the second filter have different polarization axes.

5. An inspection device, comprising:
   an illumination optical system configured to emit light onto a surface of a sample;
   a detection optical system configured to detect scattered light from the sample caused by the illumination optical system;
   a first filter disposed at a pupil plane of the detection optical system,
   the first filter having a plurality of regions of different transmission characteristics regarding the scattered light;
   a second filter disposed near the pupil plane of the detection optical system,
   the second filter having a plurality of regions with different polarization characteristics regarding the scattered light; and
   a sensor configured to detect scattered light filtered by the first and second filters.

6. An inspection device, comprising:
   an illumination optical system configured to emit light onto a surface of a sample;
   a detection optical system configured to detect scattered light from the sample caused by the illumination optical system;
   a first filter disposed near a pupil plane of the detection optical system,
   the first filter having a plurality of regions of different transmission characteristics regarding the scattered light;
   a second filter disposed at the pupil plane of the detection optical system,
   the second filter having a plurality of regions with different polarization characteristics regarding the scattered light; and
   a sensor configured to detect scattered light filtered by the first and second filters.

* * * * *